US009994883B2

(12) United States Patent
Goossens et al.

(10) Patent No.: US 9,994,883 B2
(45) Date of Patent: Jun. 12, 2018

(54) TRITERPENOID SAPOGENIN PRODUCTION IN PLANT AND MICROBIAL CULTURES

(71) Applicants: VIB VZW, Ghent (BE); Universiteit Gent, Ghent (BE)

(72) Inventors: Alain Goossens, Lokeren (BE); Tessa Moses, Ghent (BE); Jacob Pollier, Ghent (BE); Lorena Almagro Romero, Aljucer (ES)

(73) Assignees: VIB VZW, Ghent (BE); Universiteit Gent, Ghent (BE)

( * ) Notice: Subject to any disclaimer, the term of this patent is extended or adjusted under 35 U.S.C. 154(b) by 602 days.

(21) Appl. No.: 14/400,527

(22) PCT Filed: May 13, 2013

(86) PCT No.: PCT/EP2013/059821
§ 371 (c)(1),
(2) Date: Nov. 11, 2014

(87) PCT Pub. No.: WO2013/167751
PCT Pub. Date: Nov. 14, 2013

(65) Prior Publication Data
US 2015/0141633 A1 May 21, 2015

Related U.S. Application Data

(60) Provisional application No. 61/645,998, filed on May 11, 2012, provisional application No. 61/732,817, filed on Dec. 3, 2012.

(51) Int. Cl.
| | | |
|---|---|---|
| *C12P 15/00* | (2006.01) |
| *C12P 33/00* | (2006.01) |
| *C07C 35/44* | (2006.01) |
| *C07C 47/46* | (2006.01) |
| *C07C 49/727* | (2006.01) |
| *C07C 62/32* | (2006.01) |
| *C07D 307/00* | (2006.01) |
| *C12N 9/90* | (2006.01) |
| *C12P 17/04* | (2006.01) |

(52) U.S. Cl.
CPC .............. *C12P 15/00* (2013.01); *C07C 35/44* (2013.01); *C07C 47/46* (2013.01); *C07C 49/727* (2013.01); *C07C 62/32* (2013.01); *C07D 307/00* (2013.01); *C12N 9/90* (2013.01); *C12P 17/04* (2013.01); *C12P 33/00* (2013.01); *C07C 2603/52* (2017.05); *C12Y 504/99* (2013.01)

(58) Field of Classification Search
CPC .......... C12P 15/00; C12P 17/04; C07C 62/32; C07D 307/00; C12Y 114/13134
See application file for complete search history.

(56) References Cited

FOREIGN PATENT DOCUMENTS

| | | |
|---|---|---|
| EP | 2351846 A1 | 8/2011 |
| WO | 2013167751 A1 | 11/2013 |

OTHER PUBLICATIONS

Lambert et al., Modulation of Triterpene Saponin Production: In Vitro Cultures, Elicitation, and Metabolic Engineering, Applied Biochemistry and Biotechnology, 2011, pp. 220-237, vol. 164, Humana Press Inc., New York, US.
Kirby et al., Engineering triterpene production in *Saccharomyces cerevisiae*-beta-amyrin synthase from Artimisia annua, FEBS Journal, Apr. 10, 20008, pp. 1852-1859, vol. 275, No. 8.
Kastelic-Shudolc et al., Involvement of the Cell Wall to Nocardia-Restricta on the Bioconversions of Steroid Sapogenins, World Journal of Microbiology and Biotechnology, Jan. 1, 1991, pp. 22-24, vol. 7, No. 1 Rapid Communications of Oxford, Oxford, GB.
Augustin et al., Molecular activities, biosynthesis and evolution of triterpenoid saponins, Photochemistry, Jan. 11, 2011, pp. 435-457, vol. 72, No. 6, Pergamon Press, GB.
Singer et al., Microbial Transformations in a Cyclodextrin Medium Part 2, Reduction of Androstenedione to Testosterone by *Saccharomyces-cerevisiae*, Applied Microbiology and Biotechnology, 1991, pp. 731-737, vol. 35, No. 6.
Moses, Tessa, Metabolic engineering for production of triterpenoid saponin building blocks in plants and yeast, Thesis, Ghent University, Faculty of Sciences, Belgium, Dec. 1, 2012, pp. 1-225.
Moses et al., Bioengineering of plant (tri)terpenoids: from metabolic engineering of plants to synthetic biology in vivo and in vitro, New Phytologist, May 14, 2013, retrieved from the Internet: URL: http://onlinelibrary.wiley.com/doi/10.1111/nph.12325/pds [Retrieved on Aug. 9, 2013].
Triterpene sapogenins, Phytolab, online catalogue 2012, pp. 1-2, XP002711222, Retrieved from the Internet: URL: http://phyproof.phytolab.de/reference-substances/isoprenoids/terpenoid-type/triterpenes/triterpene-sapogenins.html?_from _store=default&_store=english&dir=asc&limit=16&order=cas&p=3, retrieved on Aug. 13, 2013.
PCT International Search Report, PCT/EP2013/059821, dated Oct. 28, 2013.
Jambhekar et al., Cyclodextrins in pharmaceutical formulations I: structure and physicochemical properties, formation of complexes, and types of complexes, Feb. 2016, Drug Discovery Today, vol. 21, No. 2, pp. 357-362.
Li et al., Triterpenoids of Marine Origin as Anti-Cancer Agents, Molecules 2013, 18, pp. 7886-7909.

*Primary Examiner* — Kagnew H Gebreyesus
(74) *Attorney, Agent, or Firm* — TraskBritt, P.C.

(57) ABSTRACT

The disclosure relates to a method for enhancing the biosynthesis and/or secretion of sapogenins in the culture medium of plant and microbial cell cultures. Further, the disclosure also relates to the identification of novel genes involved in the biosynthesis of sapogenin intermediates, as well as to novel sapogenin compounds.

11 Claims, 33 Drawing Sheets
(15 of 33 Drawing Sheet(s) Filed in Color)

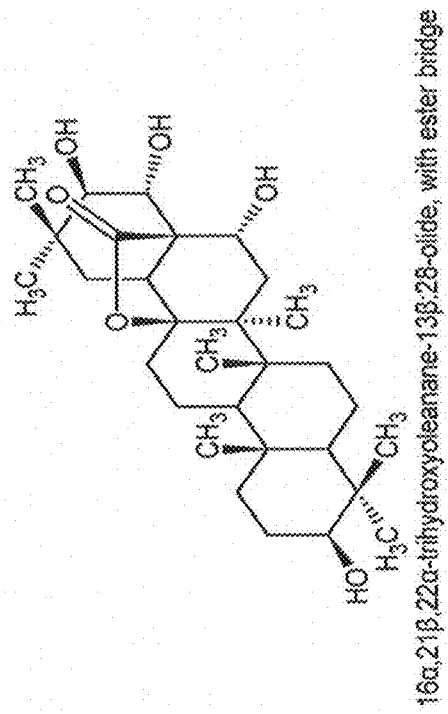
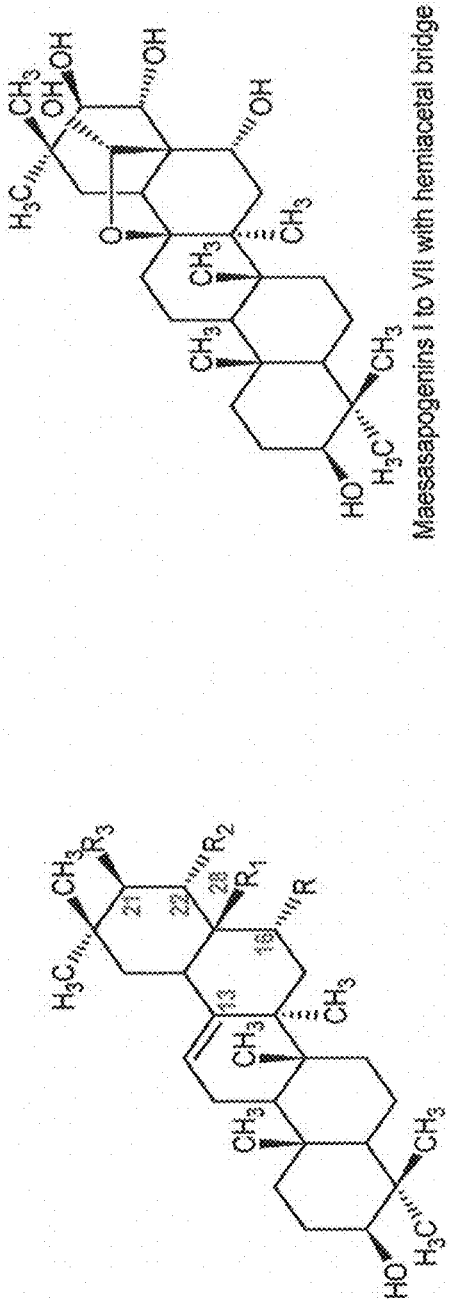
FIG. 14

SEQUENCE LISTING

<160> NUMBER OF SEQ ID NOS: 21

<210> SEQ ID NO 1
<211> LENGTH: 1437
<212> TYPE: DNA
<213> ORGANISM: Bupleurum falcatum

<400> SEQUENCE: 1

```
atggaacttt ctatcactct gatgcttatt ttctcaacaa ccatcttctt tatatttcgt      60
aatgtgtaca accatctcat ctctaaacac aaaaactatc cccctggaag tatgggcttg     120
ccttacattg gcgaaacact tagtttcgcg agatacatca ccaaaggagt ccctgaaaaa     180
```

```
ttcgtaatag aaagacaaaa gaaatattca acaacaatat ttaagacctc cttgttcgga      240
gaaaacatgg tggtgttggg cagtgcagag ggcaacaaat ttattttttgg aagcgaggag     300 aagtatttac gagtgtggtt tccaagttct gtggacaaag tgttcaaaaa atctcataag     360
agaacgtcgc aggaagaagc tattaggttg cgcaaaaaca tggtgccatt tctcaaagca     420
gatttgttga aagttatgt accaataatg acacattta tgaaacaaca tgtgaactcg       480
cattggaatt gcgagacctt gaaggcttgt cctgtgatca aggattttac gtttacttta    540
gcttgtaaac ttttttttag tgtagacaat cctttggagc tagagaagtt aatcaagcta    600
tttgtgaata tagtgaatgg cctccttacg gtccctattg atctcccggg acaaaatttt    660
agaggagtta taagagtgt caagactatt cgccatgcgc ttaaagtgtt gatcaggcaa     720
cgaaaggtgg atattagaga gaaaagagcc acacctacgc aagatatatt gtcgataatg    780
ctggcacagg ctgaggacga gaactatgaa atgaatgatg aagatgtggc caatgacttt    840
cttgcagttt tgcttgctag ttatgattct gccaatacta cactcaccat gattatgaaa    900
tatcttgctg aatatcccga aatgtatgat cgagttttca gagaacaaat ggaggtggca    960
aagacgaaag gaaaagatga attactcaac ttggacgact tgcaaaagat gaattatact   1020
tggaatgtag cttgtgaagt actgagaatt gcaacaccaa cgttcggagc attcagagag   1080
gttattgcag attgtacata cgaagggtac accataccaa aaggctggaa gctatattat   1140
gccccgcgtt ttacccatgg aagtgcaaaa tactttcaag atccagaaa atttgatcca   1200 tcgcgatttg aaggtgatgg tgcgcctcct tatacattcg ttccattcgg aggagggctc   1260
cggatgtgcc ctggatacaa gtatgcaaag attatagtac tagtgttcat gcacaatata   1320
gttacaaagt tcaaatggga gaaagttaac cctaatgaga aaatgacagt aggaatcgta   1380
tcagcgccaa gtcaaggact tccactgcgt ctccatcccc acaaatctcc atcttaa     1437

<210> SEQ ID NO 2
<211> LENGTH: 1428
<212> TYPE: DNA
<213> ORGANISM: Maesa lanceolata

<400> SEQUENCE: 2
atgtgggtag tgggattaat tggtgtggct gtggtaacaa tattgataac tcagtatgta     60
tacaaatgga gaaatccaaa gactgtgggt gttctgccac ctggttcaat gggtctgcct    120
ttgatcgggg agactcttca acttctcagc cgtaatccat ccttggatct tcatccttttc   180 atcaagagca gaatccaaag atatgggcag atattcgcga ccaatatcgt aggtcgaccc    240
ataatagtaa ccgctgatcc gcagctcaat aattaccttt ccaacaaga aggaagagca    300 gtagaactgt ggtacttgga cagctttcaa aagctattta acttagaagg tgcaaacagg    360
ccgaacgcag ttggtcacat tcacaagtac gttagaagtg tatacttgag tctctttggc    420
gtcgagagcc ttaaaacaaa gttgcttgcc gatattgaga aaacagtccg caaaaatctt    480
attggtggga caaccaaagg caccttttgat gcaaaacatg cttctgccaa tatggttgct    540 gttttttgctg caaaatactt gttcggacat gattacgaga atcgaaaga agatgtaggc    600 agcataatcg acaacttcgt acaaggtctt ctcgcattcc cattgaatgt tcccggtaca    660
aagttccaca atgtatgaa ggacaagaaa aggctggaat caatgatcac taacaagcta    720
aaggagagaa tagctgatcc gaacagcgga caagggggatt tccttgatca agcagtgaaa    780
gacttgaata gcgaattctt cataacagag acttttatcg tttcggtgac gatgggagct    840
ttatttgcga cggttgaatc ggtttcgaca gcaattggac tagctttcaa gtttttttgca   900
```

-continued

```
gagcacccct gggttttgga tgacctcaag gctgagcatg aggctgtcct tagcaaaaga    960
gaggatagaa attcacctct cacgtgggac gaatatagat cgatgacaca cacgatgcac   1020
tttatcaatg aagtcgtccg tttgggaaat gttttcctg gaattttgag gaaagcactg   1080
aaagatattc catataatgg ttatacaatt ccgtccggtt ggaccattat gattgtgacc   1140 tctaccttg cgatgaaccc tgagatattc aaggatcctc ttgcattcaa tccgaaacgt   1200
tggcgggata ttgatcccga aactcaaact aaaaacttta tgcctttcgg tggtgggacg   1260
agacaatgcg caggtgcaga gctagccaag gcattctttg ctaccttcct ccatgtttta   1320
atcagcgaat atagctggaa gaaagtgaag ggaggaagcg ttgctcggac acctatgtta   1380
agttttgaag atggcatatt tattgaggtc accaagaaaa acaagtga                1428
```

<210> SEQ ID NO 3
<211> LENGTH: 478
<212> TYPE: PRT
<213> ORGANISM: Bupleurum falcatum

<400> SEQUENCE: 3

```
Met Glu Leu Ser Ile Thr Leu Met Leu Ile Phe Ser Thr Thr Ile Phe
1               5                   10                  15

Phe Ile Phe Arg Asn Val Tyr Asn His Leu Ile Ser Lys His Lys Asn
            20                  25                  30

Tyr Pro Pro Gly Ser Met Gly Leu Pro Tyr Ile Gly Glu Thr Leu Ser
        35                  40                  45

Phe Ala Arg Tyr Ile Thr Lys Gly Val Pro Glu Lys Phe Val Ile Glu
    50                  55                  60

Arg Gln Lys Lys Tyr Ser Thr Thr Ile Phe Lys Thr Ser Leu Phe Gly
65                  70                  75                  80

Glu Asn Met Val Val Leu Gly Ser Ala Glu Gly Asn Lys Phe Ile Phe
                85                  90                  95

Gly Ser Glu Glu Lys Tyr Leu Arg Val Trp Phe Pro Ser Ser Val Asp
            100                 105                 110

Lys Val Phe Lys Lys Ser His Lys Arg Thr Ser Gln Glu Glu Ala Ile
        115                 120                 125

Arg Leu Arg Lys Asn Met Val Pro Phe Leu Lys Ala Asp Leu Leu Arg
    130                 135                 140

Ser Tyr Val Pro Ile Met Asp Thr Phe Met Lys Gln His Val Asn Ser
145                 150                 155                 160

His Trp Asn Cys Glu Thr Leu Lys Ala Cys Pro Val Ile Lys Asp Phe
                165                 170                 175

Thr Phe Thr Leu Ala Cys Lys Leu Phe Phe Ser Val Asp Asn Pro Leu
            180                 185                 190

Glu Leu Glu Lys Leu Ile Lys Leu Phe Val Asn Ile Val Asn Gly Leu
        195                 200                 205

Leu Thr Val Pro Ile Asp Leu Pro Gly Thr Lys Phe Arg Gly Val Ile
    210                 215                 220

Lys Ser Val Lys Thr Ile Arg His Ala Leu Lys Val Leu Ile Arg Gln
225                 230                 235                 240

Arg Lys Val Asp Ile Arg Glu Lys Arg Ala Thr Pro Thr Gln Asp Ile
                245                 250                 255

Leu Ser Ile Met Leu Ala Gln Ala Glu Asp Glu Asn Tyr Glu Met Asn
            260                 265                 270

Asp Glu Asp Val Ala Asn Asp Phe Leu Ala Val Leu Leu Ala Ser Tyr
        275                 280                 285
```

```
Asp Ser Ala Asn Thr Thr Leu Thr Met Ile Met Lys Tyr Leu Ala Glu
    290                 295                 300

Tyr Pro Glu Met Tyr Asp Arg Val Phe Arg Glu Gln Met Glu Val Ala
305                 310                 315                 320

Lys Thr Lys Gly Lys Asp Glu Leu Leu Asn Leu Asp Asp Leu Gln Lys
                325                 330                 335

Met Asn Tyr Thr Trp Asn Val Ala Cys Glu Val Leu Arg Ile Ala Thr
                340                 345                 350

Pro Thr Phe Gly Ala Phe Arg Glu Val Ile Ala Asp Cys Thr Tyr Glu
            355                 360                 365

Gly Tyr Thr Ile Pro Lys Gly Trp Lys Leu Tyr Ala Pro Arg Phe
370                 375                 380

Thr His Gly Ser Ala Lys Tyr Phe Gln Asp Pro Glu Lys Phe Asp Pro
385                 390                 395                 400

Ser Arg Phe Glu Gly Asp Gly Ala Pro Pro Tyr Thr Phe Val Pro Phe
                405                 410                 415

Gly Gly Gly Leu Arg Met Cys Pro Gly Tyr Lys Tyr Ala Lys Ile Ile
                420                 425                 430

Val Leu Val Phe Met His Asn Ile Val Thr Lys Phe Lys Trp Glu Lys
            435                 440                 445

Val Asn Pro Asn Glu Lys Met Thr Val Gly Ile Val Ser Ala Pro Ser
450                 455                 460

Gln Gly Leu Pro Leu Arg Leu His Pro His Lys Ser Pro Ser
465                 470                 475

<210> SEQ ID NO 4
<211> LENGTH: 475
<212> TYPE: PRT
<213> ORGANISM: Maesa lanceolata

<400> SEQUENCE: 4

Met Trp Val Val Gly Leu Ile Gly Val Ala Val Val Thr Ile Leu Ile
1               5                   10                  15

Thr Gln Tyr Val Tyr Lys Trp Arg Asn Pro Lys Thr Val Gly Val Leu
            20                  25                  30

Pro Pro Gly Ser Met Gly Leu Pro Leu Ile Gly Glu Thr Leu Gln Leu
        35                  40                  45

Leu Ser Arg Asn Pro Ser Leu Asp Leu His Pro Phe Ile Lys Ser Arg
    50                  55                  60

Ile Gln Arg Tyr Gly Gln Ile Phe Ala Thr Asn Ile Val Gly Arg Pro
65                  70                  75                  80

Ile Ile Val Thr Ala Asp Pro Gln Leu Asn Asn Tyr Leu Phe Gln Gln
                85                  90                  95

Glu Gly Arg Ala Val Glu Leu Trp Tyr Leu Asp Ser Phe Gln Lys Leu
            100                 105                 110

Phe Asn Leu Glu Gly Ala Asn Arg Pro Asn Ala Val Gly His Ile His
        115                 120                 125

Lys Tyr Val Arg Ser Val Tyr Leu Ser Leu Phe Gly Val Glu Ser Leu
    130                 135                 140

Lys Thr Lys Leu Leu Ala Asp Ile Glu Lys Thr Val Arg Lys Asn Leu
145                 150                 155                 160

Ile Gly Gly Thr Thr Lys Gly Thr Phe Asp Ala Lys His Ala Ser Ala
                165                 170                 175

Asn Met Val Ala Val Phe Ala Ala Lys Tyr Leu Phe Gly His Asp Tyr
                180                 185                 190
```

Glu Lys Ser Lys Glu Asp Val Gly Ser Ile Ile Asp Asn Phe Val Gln
            195                 200                 205

Gly Leu Leu Ala Phe Pro Leu Asn Val Pro Gly Thr Lys Phe His Lys
210                 215                 220

Cys Met Lys Asp Lys Lys Arg Leu Glu Ser Met Ile Thr Asn Lys Leu
225                 230                 235                 240

Lys Glu Arg Ile Ala Asp Pro Asn Ser Gly Gln Gly Asp Phe Leu Asp
            245                 250                 255

Gln Ala Val Lys Asp Leu Asn Ser Glu Phe Phe Ile Thr Glu Thr Phe
            260                 265                 270

Ile Val Ser Val Thr Met Gly Ala Leu Phe Ala Thr Val Glu Ser Val
            275                 280                 285

Ser Thr Ala Ile Gly Leu Ala Phe Lys Phe Phe Ala Glu His Pro Trp
            290                 295                 300

Val Leu Asp Asp Leu Lys Ala Glu His Glu Ala Val Leu Ser Lys Arg
305                 310                 315                 320

Glu Asp Arg Asn Ser Pro Leu Thr Trp Asp Glu Tyr Arg Ser Met Thr
            325                 330                 335

His Thr Met His Phe Ile Asn Glu Val Val Arg Leu Gly Asn Val Phe
            340                 345                 350

Pro Gly Ile Leu Arg Lys Ala Leu Lys Asp Ile Pro Tyr Asn Gly Tyr
            355                 360                 365

Thr Ile Pro Ser Gly Trp Thr Ile Met Ile Val Thr Ser Thr Leu Ala
            370                 375                 380

Met Asn Pro Glu Ile Phe Lys Asp Pro Leu Ala Phe Asn Pro Lys Arg
385                 390                 395                 400

Trp Arg Asp Ile Asp Pro Glu Thr Gln Thr Lys Asn Phe Met Pro Phe
            405                 410                 415

Gly Gly Gly Thr Arg Gln Cys Ala Gly Ala Glu Leu Ala Lys Ala Phe
            420                 425                 430

Phe Ala Thr Phe Leu His Val Leu Ile Ser Glu Tyr Ser Trp Lys Lys
            435                 440                 445

Val Lys Gly Gly Ser Val Ala Arg Thr Pro Met Leu Ser Phe Glu Asp
            450                 455                 460

Gly Ile Phe Ile Glu Val Thr Lys Lys Asn Lys
465                 470                 475

<210> SEQ ID NO 5
<211> LENGTH: 49
<212> TYPE: DNA
<213> ORGANISM: Artificial Sequence
<220> FEATURE:
<223> OTHER INFORMATION: Primer

<400> SEQUENCE: 5
ggggacaagt tgtacaaaa aagcaggctt aatggaactt tctatcact        49

<210> SEQ ID NO 6
<211> LENGTH: 48
<212> TYPE: DNA
<213> ORGANISM: Artificial Sequence
<220> FEATURE:
<223> OTHER INFORMATION: Primer

<400> SEQUENCE: 6
ggggaccact ttgtacaaga aagctgggta ttaagatgga gatttgtg        48

<210> SEQ ID NO 7
<211> LENGTH: 54
<212> TYPE: DNA
<213> ORGANISM: Artificial Sequence
<220> FEATURE:
<223> OTHER INFORMATION: Primer

<400> SEQUENCE: 7
ggggaccact tgtacaaga aagctgggta ttaagctttg tgtggataaa ggcg    54

<210> SEQ ID NO 8
<211> LENGTH: 50
<212> TYPE: DNA
<213> ORGANISM: Artificial Sequence
<220> FEATURE:
<223> OTHER INFORMATION: Primer

<400> SEQUENCE: 8
accgcaugtt agcagacttc ctctgccctc agatggagat tgtgggat    50

<210> SEQ ID NO 9
<211> LENGTH: 50
<212> TYPE: DNA
<213> ORGANISM: Artificial Sequence
<220> FEATURE:
<223> OTHER INFORMATION: Primer

<400> SEQUENCE: 9
atgcggugac gtcgaggaga atcctggccc aatggagcct aatttctatc    50

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
ctcttgcatt caatccgaaa c    21

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
agcaaagaat gccttggcta    20

<210> SEQ ID NO 12
<211> LENGTH: 49
<212> TYPE: DNA
<213> ORGANISM: Artificial Sequence
<220> FEATURE:
<223> OTHER INFORMATION: Primer

<400> SEQUENCE: 12
ggggacaagt tgtacaaaa aagcaggctt aatgtgggta gtgggatta    49

<210> SEQ ID NO 13
<211> LENGTH: 48
<212> TYPE: DNA
<213> ORGANISM: Artificial Sequence
<220> FEATURE:
<223> OTHER INFORMATION: Primer

<400> SEQUENCE: 13
ggggaccact tgtacaaga aagctgggta tcacttgttt ttcttggt                48

<210> SEQ ID NO 14
<211> LENGTH: 58
<212> TYPE: DNA
<213> ORGANISM: Artificial Sequence
<220> FEATURE:
<223> OTHER INFORMATION: Primer

<400> SEQUENCE: 14
ggggacaagt tgtacaaaaa aagcaggctt actcgagatg tggaagctga agatagca    58

<210> SEQ ID NO 15
<211> LENGTH: 57
<212> TYPE: DNA
<213> ORGANISM: Artificial Sequence
<220> FEATURE:
<223> OTHER INFORMATION: Primer

<400> SEQUENCE: 15
ggggaccact tgtacaaga aagctgggtt gctagctcaa ttggagagcc acaagcg      57

<210> SEQ ID NO 16
<211> LENGTH: 51
<212> TYPE: DNA
<213> ORGANISM: Artificial Sequence
<220> FEATURE:
<223> OTHER INFORMATION: Primer

<400> SEQUENCE: 16
ggggacaagt tgtacaaaaa aagcaggctt aatggaagta cattgggttt g           51

<210> SEQ ID NO 17
<211> LENGTH: 50
<212> TYPE: DNA
<213> ORGANISM: Artificial Sequence
<220> FEATURE:
<223> OTHER INFORMATION: Primer

<400> SEQUENCE: 17
ggggaccact tgtacaaga aagctgggta ctaagcacat gaaacctta               50

<210> SEQ ID NO 18
<211> LENGTH: 50
<212> TYPE: DNA
<213> ORGANISM: Artificial Sequence
<220> FEATURE:
<223> OTHER INFORMATION: Primer

<400> SEQUENCE: 18
accgcaugtt agcagacttc ctctgccctc cttgttttc ttggtgacct               50

<210> SEQ ID NO 19
<211> LENGTH: 50
<212> TYPE: DNA
<213> ORGANISM: Artificial Sequence
<220> FEATURE:
<223> OTHER INFORMATION: Primer

<400> SEQUENCE: 19
atgcggugac gtcgaggaga atcctggccc aatggaagta cattgggttt              50

```
<210> SEQ ID NO 20
<211> LENGTH: 24
<212> TYPE: DNA
<213> ORGANISM: Artificial Sequence
<220> FEATURE:
<223> OTHER INFORMATION: Primer

<400> SEQUENCE: 20
cctccttata cattcgttcc attc                                              24

<210> SEQ ID NO 21
<211> LENGTH: 24
<212> TYPE: DNA
<213> ORGANISM: Artificial Sequence
<220> FEATURE:
<223> OTHER INFORMATION: Primer

<400> SEQUENCE: 21
ttagggtcta ctttctccca tttg                                              24
```

TRITERPENOID SAPOGENIN PRODUCTION IN PLANT AND MICROBIAL CULTURES

CROSS-REFERENCE TO RELATED APPLICATIONS

This application is a national phase entry under 35 U.S.C. § 371 of International Patent Application PCT/EP2013/059821, filed May 13, 2013, designating the United States of America and published in English as International Patent Publication WO 2013/167751 A1 on Nov. 14, 2013, which claims the benefit under Article 8 of the Patent Cooperation Treaty and under 35 U.S.C. § 119(e) to U.S. Provisional Patent Application Ser. No. 61/732,817, filed Dec. 3, 2012 and to U.S. Provisional Patent Application Ser. No. 61/645,998, filed May 11, 2012.

STATEMENT ACCORDING TO 37 C.F.R. § 1.821(c) or (e)-SEQUENCE LISTING SUBMITTED AS PDF FILE WITH A REQUEST TO TRANSFER CRF FROM PARENT APPLICATION

Pursuant to 37 C.F.R. § 1.821(c) or (e), a file containing a PDF version of the Sequence Listing has been submitted concomitant with this application, the contents of which are hereby incorporated by reference. The transmittal documents of this application include a Request to Transfer CRF from the parent application.

TECHNICAL FIELD

The disclosure relates to the fields of plant secondary metabolites with pharmacological or other industrial properties and metabolic engineering of these phytochemicals. More specifically, the disclosure relates to a method for enhancing the biosynthesis and/or secretion of sapogenin intermediates in the culture medium of plant and microbial cell cultures. Further, the disclosure also relates to the identification of novel genes involved in the biosynthesis of sapogenin intermediates, as well as to novel sapogenin compounds.

BACKGROUND

Plants synthesize an overwhelming variety of triterpene saponins with an enormous range of biological activities relevant for the pharmaceutical and chemical industry (e.g., additives to foods and cosmetics). Interest in triterpenoid saponins and its precursors has increased recently because of data showing their diverse biological activities and beneficial properties, which include antifungal, antibacterial, antiviral, antitumor, molluscicidal, insecticidal, and antifeedant activities (Suzuki et al. 2002; Sparg et al. 2004; Huhman et al. 2005). Saponins are synthesized by multiple glycosylations of sapogenin building blocks, which, in turn, are produced by multiple modifications (e.g., hydroxylations) of basic sapogenin backbones such as β-amyrin, lupeol, and dammarenediol. These diverse backbones are generated by specific cyclizations of 2,3-oxidosqualene, which is also an intermediate in the synthesis of membrane sterols. As an illustration, more than seventy saponins have been identified in the model legume, M. truncatula (Huhman and Sumner 2002; Pollier et al. 2011), the core of this diversity being centralized in a few aglycones (sapogenins). Also, these precursor sapogenins are very valuable compounds and are important starter molecules for further synthetic modifications. For example, the naturally occurring triterpenoid sapogenin oleanolic acid and its derivatives possess several promising pharmacological activities, such as hepato-protective effects, and anti-inflammatory, antioxidant, or anti-cancer activities (Pollier and Goossens 2012).

The first committed step in triterpenoid saponin biosynthesis is the cyclization of 2,3-oxidosqualene (FIG. 1). This reaction is catalyzed by specific oxidosqualene cyclases (OSCs), including β-amyrin synthase (bAS; EC 5.4.99.-), and has been functionally characterized in several plants (Kushiro et al. 1998, Herrera et al. 1998, Iturbe-Ormaetxe et al. 2003, Morita et al. 2000, Suzuki et al. 2002). Then, the action of oxidative enzymes (typically cytochrome P450 monooxygenases or CYPs) and glycosyltransferases convert β-amyrin to various triterpene saponins in different plant species. For example, subsequent modifications that impart functional properties and diversify the basic triterpenoid backbone include the addition of small functional groups, including hydroxyl, keto, aldehyde, and carboxyl moieties, generally followed by glycosylation reactions (Augustin et al. 2011). To date, a number of CYPs that use β-amyrin as a substrate have been identified in dicotyledonous plants, whereas just one (CYP51H10) has been identified in monocots.

Present availability of saponins and sapogenins depends on their extractability from plants and is often uneconomical and inefficient. Often, laborious extraction schemes have to be developed for each specific metabolite of interest and a steady supply of sufficient amounts of specific sapo(ge)nins from plants that accumulate mixtures of structurally related compounds is not feasible. Synthetic chemistry mainly attempts to address these issues by chemically linking desired side chains to extracted sapogenins, as was done for oleanolic acid. However, the structural complexity of the sapogenins hampers chemical synthesis and the availability of corresponding sapogenins forms a major bottleneck.

The culture of plant cells has been explored since the 1960s as a viable alternative for the production of complex phytochemicals of industrial interest. For example, the use of large-scale plant cell cultures in bioreactors for the production of alkaloids has been extensively studied (Verpoorte et al. 1999). Despite the promising features and developments, the production of plant-derived pharmaceuticals by plant cell cultures has not been fully commercially exploited. The main reasons for this reluctance shown by industry to produce phytochemicals by means of cell cultures, compared to the conventional extraction of whole plant material, are economical ones based on the slow growth and the low production levels of phytochemicals by such plant cell cultures. Important causes are the toxicity of such compounds to the plant cell, and the role of catabolism of these compounds. Another important problem is that many phytochemicals, such as the triterpene saponins and its precursors, are mostly retained intracellularly, complicating the downstream processing and purification. Another important problem is that for many phytochemicals, the precursors or intermediates in the pathway do not accumulate or only in trace amounts, because they are readily converted by the downstream enzymes.

Biotechnological production of either complete saponins, or of sapogenin pathway intermediates that are not readily accessible, may circumvent the limitation of natural sapo (ge)nin availability. However, circumvention of laborious and uneconomical extraction procedures for industrial production from plants is also hampered by lack of knowledge and availability of genes in saponin biosynthesis. As a consequence, although triterpene synthases have been expressed in microbial hosts such as *Saccharomyces cerevisiae*, there has been little effort made so far to engineer the metabolism of a microbial host for enhanced production of triterpenes. By contrast, there have been many considerable efforts to engineer microbes for higher production of mono-, sesqui- and diterpenes. Notably, triterpene production may not be as amenable to engineering efforts as the volatile sesquiterpenes and monoterpenes that readily diffuse out of the cell.

Therefore, a need exists for the cost-effective biotechnological production of high value sapo(ge)nins or other triterpene building blocks in a convenient host cell.

BRIEF SUMMARY

Evidence is available that sapogenins, when produced in their natural hosts (plants), are often only found in trace amounts intracellularly in plant cells, as also demonstrated in Example 1. Moreover, and as shown in Examples 3 and 4, although sapogenins can be heterologously produced in genetically engineered yeast cells, they are only detected when extracted from the cells, and they are not found in the growth medium. In order to overcome these problems, it has been found that by incubating a eukaryotic cell culture that is capable of intracellularly synthesizing sapogenins in a culture medium with cyclodextrins, significant amounts of sapogenins can be extracted from the culture medium (Examples 5, 6 and 7). Cyclodextrins, which are cyclic oligosaccharides consisting of five or more α-D-glucopyranose residues linked by a(1→4) glucosidic bonds, are known to act as sequestering agents of phytosterols from membranes (Raffaele et al. 2009) and have been used as elicitors to increase the production and extraction of phytosterols from cultures of plant cells (EP2351846; Sabater-Jara et al. 2010). In the disclosure, it is shown that intracellularly synthesized sapogenins can be released in the growth medium of eukaryotic cell cultures in the presence of cyclodextrins and can accumulate in significant amounts. In addition, it was shown that substantially higher amounts can be obtained by repeatedly adding cyclodextrins to the culture medium.

Thus, in a first aspect, the disclosure relates to a method for producing triterpenoid sapogenins in the extracellular medium of a eukaryotic cell culture comprising:
  a. providing eukaryotic cells capable of synthesizing triterpenoid sapogenins under suitable conditions;
  b. incubating the cells in culture medium comprising cyclodextrins; and
  c. optionally, extracting the sapogenins from the culture medium.

In certain embodiments, the eukaryotic cells naturally produce triterpenoid sapogenins, such as plants cells. Alternatively, the eukaryotic cells are genetically engineered to produce triterpenoid sapogenins. Such genetically engineered eukaryotic cells can be microbial cells, such as yeast cells, or plant cells, or algal cells.

In certain embodiments, the cyclodextrins are selected from the group comprising randomly methylated cyclodextrins or hydroxypropylated cyclodextrins. Preferably, the cyclodextrin is a β-cyclodextrin. According to particular embodiments, the cyclodextrins may be added to the culture medium once or at different consecutive time points.

In other aspects, the disclosure also envisages eukaryotic cells genetically engineered to synthesize sapogenins.

Further, a sapogenin obtained by any of the above-described methods is also encompassed.

According to yet another aspect, the disclosure relates to an isolated polypeptide selected from the group consisting of:
  (a) a polypeptide encoded by a polynucleotide comprising SEQ ID NO:1 or 2;
  (b) a polypeptide comprising a polypeptide sequence having a least 75% identity to the polypeptide encoded by a polynucleotide sequence having SEQ ID NO:1 or 2;
  (c) a polypeptide comprising an amino acid sequence as set forth in SEQ ID NO:3 or 4;
  (d) a polypeptide comprising an amino acid sequence with at least 75% identity to SEQ ID NO:3 or 4;
  (e) fragments and/or variants of the polypeptides according to (a), (b), (c), or (d).

In one embodiment, the disclosure relates to any of the above-described polypeptides wherein the polypeptide sequence is consisting of an amino acid sequence as set forth in SEQ ID NO:3 or 4 and polypeptide sequences having at least 75% identity to SEQ ID NO:3 or 4.

According to yet another aspect, the disclosure relates to an isolated polynucleotide selected from the group consisting of:
  (a) a polynucleotide comprising a polynucleotide sequence having the sequence SEQ ID NO:1 or 2;
  (b) a polynucleotide comprising a polynucleotide sequence having at least 70% identity to the sequence having SEQ ID NO:1 or 2;
  (c) a polynucleotide that encodes the polypeptide sequence as set forth in SEQ ID NO:3 or 4;
  (d) a polynucleotide that encodes the polypeptide sequence as set forth in SEQ ID NO:3 or 4;
  (e) fragments and variants of the polynucleotides according to (a), (b), (c) or (d).

In a specific embodiment, the disclosure relates to a chimeric gene comprising the following operably linked sequences: a) a promoter region capable of directing expression in a eukaryotic cell (as defined hereinbefore); b) a DNA region encoding a polypeptide as defined above; and c) a 3' polyadenylation and transcript termination region.

A vector comprising a polynucleotide sequence or a chimeric gene as defined above also forms part of the disclosure, as well as a host cell comprising a polynucleotide sequence or a chimeric gene or a vector as defined above.

According to a particular aspect, the disclosure provides a transgenic plant or a cell derived thereof that is transformed with the above-described vector.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 14: Chemical structure of maesasapogenins.

DETAILED DESCRIPTION

Figure 1:
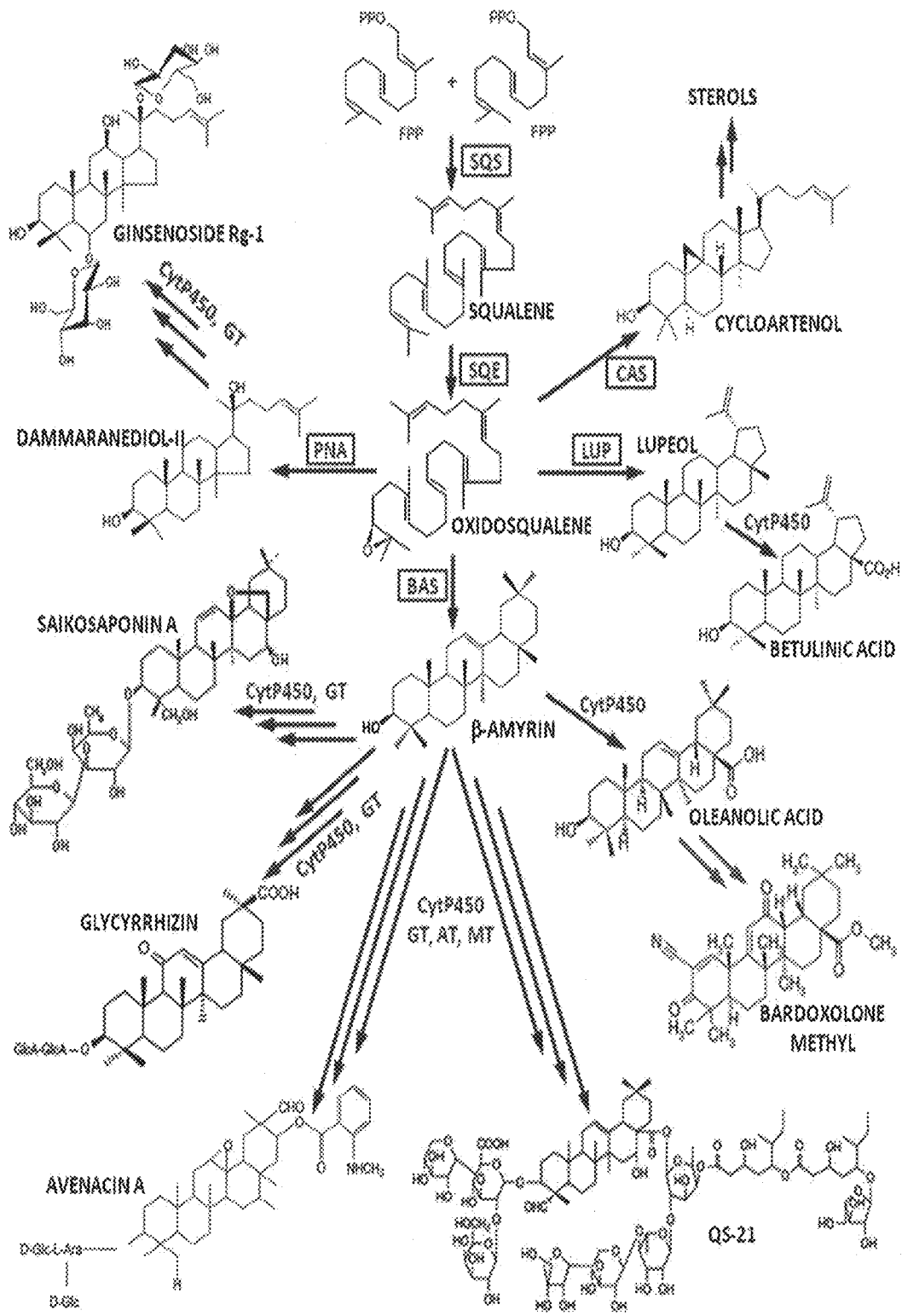
FIG. 1: Plant bioactive triterpene saponins. Schematic summary of biosynthetic pathways and variability in structure. Single and multiple arrows indicate single and multiple catalytic (enzymatic or semi-synthetic) conversions, respectively. AT, acyltransferase; BAS, β-amyrin synthase; CAS, cycloartenol synthase; CytP450, Cytochrome P450; FPP, farnesylpyrophosphate; GT, glycosyltransferase; LUP, lupeol synthase; MT, methyltransferase; PNA, dammarenediol-II synthase; SQE, squalene epoxidase; and SQS, squalene synthase.

The disclosure will be described with respect to particular embodiments and with reference to certain drawings; the disclosure is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in this description and claims, it does not exclude other elements or steps. Where an indefinite or definite article is used when referring to a singular noun, e.g., "a" or "an," "the," this includes a plural of that noun unless something else is specifically stated. Furthermore, the terms "first," "second," "third," and the like, in the description and in the claims, are used for distinguishing between similar elements and not necessarily for describing a sequential or chronological order. It is to be understood that the terms so used are interchangeable under appropriate circumstances and that the embodiments of the disclosure described herein are capable of operation in sequences other than described or illustrated herein.

Unless otherwise defined herein, scientific and technical terms and phrases used in connection with the disclosure shall have the meanings that are commonly understood by those of ordinary skill in the art. Generally, nomenclatures used in connection with, and techniques of molecular and cellular biology, genetics and protein and nucleic acid chemistry and hybridization described herein are those well-known and commonly used in the art. The methods and techniques of the disclosure are generally performed according to conventional methods well known in the art and as described in various general and more specific references that are cited and discussed throughout this specification unless otherwise indicated. See, for example, Sambrook et al., *Molecular Cloning: A Laboratory Manual,* 2d ed., Cold Spring Harbor Laboratory Press, Cold Spring Harbor, N.Y. (1989); Ausubel et al., *Current Protocols in Molecular Biology,* Greene Publishing Associates (1992, and Supplements to 2002); and Leach, *Molecular Modelling: Principles and Applications,* 2d ed., Prentice Hall, New Jersey (2001).

According to a first aspect, the disclosure relates to a method for producing triterpenoid sapogenins in the extracellular medium of a eukaryotic cell culture comprising:
  a. providing eukaryotic cells capable of synthesizing triterpenoid sapogenins under suitable conditions; and
  b. incubating the cells in culture medium comprising cyclodextrins; and
  c. optionally, extracting the sapogenins from the culture medium.

Saponins are a group of natural bio-active compounds that consist of an isoprenoidal-derived aglycone, designated "genin" or "sapogenin," covalently linked to one or more sugar moieties. This combination of polar and non-polar structural elements in their molecules explains their soap-like behavior in aqueous solutions. Most known saponins are plant-derived secondary metabolites, though several saponins are also found in marine animals such as sea cucumbers and starfish. In plants, saponins are generally considered to be part of defense systems due to antimicrobial, fungicidal, allelopathic, insecticidal and molluscicidal, etc., activities. Typically, saponins reside inside the vacuoles of plant cells. Extensive reviews on molecular activities, biosynthesis, evolution, classification, and occurrence of saponins are given by, e.g., Augustin et al. (2011) and Vincken et al. (2007). Thus, the term "sapogenin," as used herein, refers to an aglycone, or non-saccharide, moiety of the family of natural products known as saponins.

The commonly used nomenclature for saponins distinguishes between triterpenoid saponins (also: triterpene saponins) and steroidal saponins, which is based on the structure and biochemical background of their aglycones. Both sapogenin types are thought to derive from 2,3-oxidosqualene, a central metabolite in sterol biosynthesis. In phytosterol anabolism, 2,3-oxidosqualene is mainly cyclized into cycloartenol. "Triterpenoid sapogenins" branch off the phytosterol pathway by alternative cyclization of 2,3-oxidosqualene, while "steroidal sapogenins" are thought to derive from intermediates in the phytosterol pathway downstream of cycloartenol formation (see also FIG. 1). A more detailed classification of saponins based on sapogenin structure with 11 main classes and 16 subclasses has been proposed by Vincken et al. (2007; particularly from page 276 to page 283, and also FIGS. 1 and 2), which is all incorporated herein by reference. In particular, saponins may be selected from the group comprising dammarane-type saponins, tirucallane-type saponins, lupane-type saponins, oleanane-type saponins, taraxasterane-type saponins, ursane-type saponins, hopane-type saponins, cucurbitane-type saponins, cycloartane-type saponins, lanostane-type saponins, and steroid-type saponins. The aglycon backbones, the sapogenins, can be similarly classified and may be selected from the group comprising dammarane-type sapogenins, tirucallane-type sapogenins, lupane-type sapogenins, oleanane-type sapogenins, taraxasterane-type sapogenins, ursane-type sapogenins, hopane-type sapogenins, cucurbitane-type sapogenins, cycloartane-type sapogenins, lanostane-type sapogenins, and steroid-type sapogenins. Examples of sapogenins produced in plants are given in Table 1.

According to the above definitions, and as used herein, the "triterpenoid sapogenins" may be selected from the group comprising dammarane-type sapogenins, tirucallane-type sapogenins, lupane-type sapogenins, oleanane-type sapogenins, ursane-type sapogenins, and hopane-type sapogenins. Thus, according to specific embodiments, the triterpenoid sapogenins as produced by the method of the disclosure are dammarane-type sapogenins, or tirucallane-type sapogenins, or lupane-type sapogenins, or oleanane-type sapogenins, or ursane-type sapogenins, or hopane-type sapogenins.

Triterpenoid sapogenins typically have a tetracyclic or pentacyclic skeleton. As described in the Background section, the sapogenin building blocks themselves may have multiple modifications, e.g., small functional groups, including hydroxyl, keto, aldehyde, and carboxyl moieties, of precursor sapogenin backbones such as β-amyrin, lupeol, and dammarenediol.

The terms "triterpene" and "triterpenoid" are used interchangeably herein.

It is to be understood that the triterpenoid sapogenins, as used herein, also encompass new-to-nature triterpenoid compounds, which are structurally related to the naturally occurring triterpenoid sapogenins. These new-to-nature triterpenoid sapogenins may be currently unextractable compounds by making use of existing extraction procedures or may be novel compounds that can be obtained after genetic engineering of the synthesizing eukaryotic host cell (see further herein).

For the sake of clarity, the term "triterpenoid sapogenins," as used herein, is not meant to cover phytosterols or phytosterol pathway intermediates. Phytosterols, which encompass plant sterols and stanols, are triterpenes that are important structural components of plant membranes and free phytosterols serve to stabilize phospholipid bilayers in plant cell membranes just as cholesterol does in animal cell membranes. Stanols are a fully saturated subgroup of phytosterols (contain no double bonds). Non-limiting examples of phytosterols, which form important structural components of plant membranes, are stigmasterol, β-sitosterol, fucosterol, and campesterol.

times also called cycloamyloses) are meant cyclic oligosaccharides composed of five or more (α-1,4)-linked α-D-glucopyranose subunits, which are well-known in the art. As used herein, "cyclodextrins" encompass both naturally occurring cyclodextrins as well as chemical derivatives thereof, as described further herein. Cyclodextrins possess a

TABLE 1

Triterpenoid sapogenins comprising the core of commonly accumulating saponins produced by plants.

| Plant genus | Sapogenins comprised in commonly accumulating saponins | Chemical formula of sapogenin | Reference |
|---|---|---|---|
| Medicago | 2,3-dihydro-23-oxoolean-12-en-28-oic acid | $C_{30}H_{46}O_5$ | (Tava et al., 2011) |
| | Medicagenic acid | $C_{30}H_{46}O_6$ | |
| | Zanhic acid | $C_{30}H_{46}O_7$ | |
| | Oleanolic acid; Soyasapogenol E | $C_{30}H_{48}O_3$ | |
| | Hederagenin, 2-hydroxyoleanolic acid; Queretaroic acid | $C_{30}H_{48}O_4$ | |
| | Bayogenin; 2-hydroxyqueretaroic acid; Caulophyllogenin | $C_{30}H_{48}O_5$ | |
| | Sophoradiol; 3,24-dihydroolean-12-ene | $C_{30}H_{50}O_2$ | |
| | Soyasapogenol B | $C_{30}H_{50}O_3$ | |
| | Soyasapogenol A | $C_{30}H_{50}O_4$ | |
| Panax | Dammarenediol | $C_{30}H_{52}O_2$ | (Zou et al., 2002) |
| | Panaxadiol; Protopanaxadiol | $C_{30}H_{52}O_3$ | |
| | Panaxatriol; Protopanaxatriol | $C_{30}H_{52}O_4$ | |
| Bupleurum | Rotundioside O sapogenin | $C_{30}H_{46}O_4$ | (Ashour and Wink, 2011) |
| | Rotundioside L, M sapogenin | $C_{30}H_{46}O_5$ | |
| | Sandrosapogenin III, VIII | $C_{30}H_{46}O_6$ | |
| | Sandrosapogenin IV | $C_{30}H_{46}O_7$ | |
| | Saikogenin C, M; Rotundioside B, C sapogenin; Sandrosapogenin IX, X; Rotundifolioside A, I, J sapogenin | $C_{30}H_{48}O_3$ | |
| | Saikogenin A, B1, B2, D, G, K, N, O, P, S; Prosaikogenin A, H; Rotundioside A, J, K, Q, S, V sapogenin; Rotundifolioside D, E, F, G, H Sandrosapogenin II, V, VI; Bupleuroside VI sapogenin; Saikosapogenin L, Q, Q2, R, U, V2, V; Scorzoneroside A, B, C sapogenin | $C_{30}H_{48}O_4$ | |
| | Sandrosapogenin II, V, VI; Bupleuroside VI sapogenin; Saikosapogenin L, Q, Q2, R, U, V2, V; Scorzoneroside A, B, C sapogenin | $C_{30}H_{48}O_5$ | |
| | Rotundioside D sapogenin | $C_{30}H_{50}O_3$ | |
| | Rotundifolioside B, C | $C_{30}H_{50}O_4$ | |
| | Hydroxysaikosapogenin A, C, D; Bupleuroside VIII sapogenin | $C_{30}H_{50}O_5$ | |
| | Rotundioside N sapogenin | $C_{30}H_{50}O_5$ | |
| | Saikosapogenin F | $C_{30}H_{52}O_3$ | |
| | Methoxysaikosapogenin F; Saikosapogenin T; Bupleuroside IX sapogenin; Rotundioside X, Y sapogenin | $C_{30}H_{52}O_4$ | |
| | Saikogenin B3, B4; Rotundioside P, R, U sapogenin | $C_{30}H_{52}O_5$ | |
| Maesa | 16-oxo-28-hydroxyolean-12-ene | $C_{30}H_{48}O_3$ | (Manguro et al., 2011) |
| | 16,22-dihydroxyolean-12-en-28-al | $C_{30}H_{48}O_4$ | |
| | 16,21,22-trihydroxyoleanane-13:28-ollide | $C_{30}H_{48}O_6$ | |
| | 16,28-dihydroxyolean-12-ene | $C_{30}H_{50}O_3$ | |
| | 16,22,28-trihydroxyolean-12-ene | $C_{30}H_{50}O_4$ | |
| | 16,21,22,28-tetrahydroxyolean-12-ene | $C_{30}H_{50}O_5$ | |
| | Maesasapogenin I, II, III, IV, V, VI, VII | $C_{30}H_{50}O_6$ | |
| Saponaria | Quillaic acid | $C_{30}H_{46}O_5$ | (Guo et al., 1998) |
| Betula | Betulin | $C_{30}H_{48}O_2$ | (Rickling and Glombitza, 1993) |
| | Betulinic acid | $C_{30}H_{48}O_3$ | |
| | Betulafolientetraol | $C_{30}H_{52}O_5$ | |
| Oleander | Oleanolic acid; Ursolic acid | $C_{30}H_{48}O_3$ | (Stiti et al, 2007) |
| | Maslinic acid | $C_{30}H_{48}O_4$ | |
| | Bacchara-12,21-dien-3-ol | $C_{30}H_{48}O$ | |
| | Butyrospermol | $C_{30}H_{50}O$ | |

The method of the disclosure makes use of cyclodextrins for the production of triterpenoid sapogenins in the culture medium of eukaryotic cells that are capable of synthesizing triterpenoid sapogenins. With "cyclodextrins" (CDs) (sometimes also called cycloamyloses) are meant cyclic oligosaccharides cage-like supramolecular structure, and are capable of forming inclusion complexes with a variety of guest molecules: CDs incorporate compounds in their hydrophobic cavities depending on the cavity size. The most typical cyclodextrins contain a set of six to eight glucopyranoside units in a ring (the cyclodextrin core), creating a cone shape. Within this family, α-cyclodextrins (αCD) have six glucopyranoside units, β-cyclodextrins (βCD) have seven glucopyranoside units, and γ-cyclodextrins (γCD) have eight glucopyranoside units in a ring. Each glucopyranoside unit has, according to the standard atom numbering system, one primary alcohol group at carbon 6 and two secondary alcohol groups at carbons 2 and 3. These natural cyclodextrins, in particular βCD, are of limited aqueous solubility. Therefore, several derivatives of cyclodextrins have been developed. Numerous chemical modifications of cyclodextrins are known in the art, as summarized, for instance, by A. Croft and R. Bartsch in Tetrahedron Report No. 147, *Tetrahedron* (1983) 39(9):1417-1474, and which is incorporated herein by reference. These derivatives usually are produced by aminations, esterifications or etherifications of primary and secondary hydroxyl groups of the cyclodextrins. Depending on the substituent, the solubility of the cyclodextrin derivatives is usually different from that of their parent cyclodextrins. Virtually all derivatives have a changed hydrophobic cavity volume and also these modifications can improve solubility, stability against light or oxygen and help control the chemical activity of guest molecules. For example, and without the purpose of being limitative, water-soluble cyclodextrin derivatives of commercial interest include the hydroxypropyl derivatives of βCD and γCD, the randomly methylated β-cyclodextrin (RMβCD), and sulfobutylether β-cyclodextrin sodium salt (SBEβCD).

Thus, according to a preferred embodiment, the cyclodextrin that is used in the method of the disclosure is chosen from the group comprising randomly methylated cyclodextrin or hydroxypropylated cyclodextrin. Preferably, the degree of substitution by methyls per glucose unit of the randomly methylated cyclodextrin is between one and three, and more preferably, the degree of substitution by methyls per glucose unit of the randomly methylated cyclodextrin is two. Preferably, the degree of substitution by hydroxypropyls per glucose unit of the hydroxypropylated cyclodextrin is between 0.6 and 0.9. According to another preferred embodiment, the cyclodextrin that is used in the method of the disclosure is a β-cyclodextrin. According to still another embodiment, the cyclodextrin that is used in the method of the disclosure is a methylated β-cyclodextrin.

In another embodiment, the concentration of cyclodextrins in the culture medium is less than 25 mM, preferably less than 10 mM, more preferably between 2 and 7 mM. According to more specific embodiments, the concentration of cyclodextrins in the culture medium is 5 mM or 2.5 mM, or 1 mM. In one other embodiment, cyclodextrins are added to the culture medium at one point in time, for example, immediately before or after inoculation with eukaryotic cells. Preferably, cyclodextrins are added to the culture medium at different consecutive time points, for example, immediately before or after inoculation with eukaryotic cells, and then on a daily basis after the first addition of cyclodextrins, or every other day after the first addition of cyclodextrins. This is further illustrated, without the purpose of being limitative, in Example 5.

With "production" of triterpenoid sapogenins is meant both intracellular production as well as secretion into the medium. According to a preferred embodiment, the triterpenoid sapogenins as produced by the method of the disclosure are secreted into the extracellular medium. The production of triterpenoid sapogenins typically is enhanced or induced by using the method of the disclosure. An "enhanced production" of a triterpenoid sapogenin means that there exists already a detectable amount of this metabolite in the eukaryotic cell in the absence of cyclodextrins but that detection only becomes possible in the extracellular medium upon adding cyclodextrins according to the disclosure. An "induced production" of a triterpenoid sapogenin means that there is no detectable production of this metabolite in the eukaryotic cell in the absence of cyclodextrins but that detection becomes possible in the cell and the extracellular medium upon addition of cyclodextrins according to the disclosure. With an increase in the production of one or more sapogenins according to the method of the disclosure, it is understood that production may be enhanced or induced with a factor 2, 3, 4, 5, 10, 20, 50, 100 or more, relative to the production in the absence of cyclodextrins.

Eukaryotic cells provided in the above-described method can be of any unicellular or multicellular eukaryotic organism, but, in particular embodiments, microbial, plant, and algal cells are envisaged. The nature of the cells used will typically depend on the desired sapogenins and/or the ease and cost of producing the sapogenins. According to particular embodiments, the plant cell as used is derived from a plant of the genus selected from the group comprising *Medicago, Nova, Bupleurum, Maesa, Saponaria, Betula, Quillaja, Aesculus, Chenopodium, Hedera, Acacia, Centella, Oleander, Avena, Arabidopsis,* or *Nicotiana*. The term "plant" as used herein refers to vascular plants (e.g., gymnosperms and angiosperms). According to further particular embodiments, the "microbial cell" as used herein is a yeast cell, in particular, a yeast cell of a *Saccharomyces* species (e.g., *Saccharomyces cerevisiae*), a *Hansenula* species (e.g., *Hansenula polymorpha*), a *Yarrowia* species (e.g., *Yarrowia lipolytica*), a *Kluyveromyces* species (e.g., *Kluyveromyces lactis*), a *Pichia* species (e.g., *Pichia pastoris*) or a *Candida* species (e.g., *Candida utilis*). According to a specific embodiment, the eukaryotic cells as used are *Saccharomyces* cells. According to further particular embodiments, the algal cells are derived from algae of the genus selected from the group comprising *Dunaliella, Chlorella,* or *Chlamydomonas*. According to a very particular embodiment, the eukaryotic cells as used are not plant cells.

In a particular embodiment, the eukaryotic cells may naturally have the capability of synthesizing triterpene saponins and triterpene sapogenin building blocks, such as plant cells. A "plant cell" is understood, according to the disclosure, as being any cell that is derived from or found in a plant and that is able to form or is part of undifferentiated tissues, such as calli or cell cultures, differentiated tissues such as embryos, parts of plants, plants or seeds.

In an alternative embodiment, the "eukaryotic cells," as used herein, themselves do not naturally produce triterpenoid sapo(ge)nins, but may do so after genetic engineering. Thus, preferably, eukaryotic cells artificially producing sapogenins refers to cells that, while not naturally having the ability to synthesize sapogenins, have acquired such ability by means of genetic manipulation processes including transgenesis. This particularly applies to yeast cells or algal cells, which naturally do not synthesize sapogenins. In yet another embodiment, the eukaryotic cells as used herein may be genetically engineered to produce another spectrum of sapogenins, as compared to the natural spectrum that is produced by the wild-type strain, which particularly may apply to plant cells.

Thus, according to a preferred embodiment, the "plant cell," as used herein, may be a genetically engineered plant cell, which is a plant cell derived from a transgenic plant. A "transgenic plant," as used herein, refers to a plant comprising a recombinant polynucleotide and/or a recombinant polypeptide resulting in the expression of a regulatory or biosynthetic enzyme of the sapogenin biosynthesis pathway. A transgenic plant refers to a whole plant as well as to a plant part, such as seed, fruit, leaf, or root, plant tissue, plant cells or any other plant material, and progeny thereof. A transgenic plant can be obtained by transforming a plant cell with an expression cassette and regenerating such plant cell into a transgenic plant. Such plants can be propagated vegetatively or reproductively. The transforming step may be carried out by any suitable means, including by *Agrobacterium*-mediated transformation and non-*Agrobacterium*-mediated transformation, as discussed further below. Plants can be regenerated from the transformed cell (or cells) by techniques known to those skilled in the art. Where chimeric plants are produced by the process, plants in which all cells are transformed may be regenerated from chimeric plants having transformed germ cells, as is known in the art. Methods that can be used to transform plant cells or tissue with expression vectors include both *Agrobacterium* and non *Agrobacterium* vectors. *Agrobacterium*-mediated gene transfer exploits the natural ability of *Agrobacterium tumefaciens* to transfer DNA into plant chromosomes and is described in detail in G. Gheysen, G. Angenon, and M. Van Montagu, 1998, *Agrobacterium*-mediated plant transformation: a scientifically intriguing story with significant applications in K. Lindsey (Ed.), *Transgenic Plant Research*, Harwood Academic Publishers, Amsterdam, pp. 1-33; and in H. A. Stafford (2000), *Botanical Review* 66:99-118. A second group of transformation methods is the non-*Agrobacterium*-mediated transformation and these methods are known as direct gene transfer methods. An overview is brought by P. Barcelo and P. A. Lazzeri (1998), Direct gene transfer: chemical, electrical and physical methods in K. Lindsey (Ed.), *Transgenic Plant Research*, Harwood Academic Publishers, Amsterdam, pp. 35-55. Methods include particle gun delivery, microinjection, electroporation of intact cells, polyethyleneglycol-mediated protoplast transformation, electroporation of protoplasts, liposome-mediated transformation, silicon-whiskers-mediated transformation, etc. A suitable control plant would include a genetically unaltered or non-transgenic plant of the parental line (wild-type) used to generate a transgenic plant herein.

Genetically transformed hairy root cultures can be obtained by transformation with virulent strains of *Agrobacterium rhizogenes*, and they can produce high contents of secondary metabolites, including triterpenoid sapo(ge)nins, characteristic to the mother plant. Protocols used for establishing of hairy root cultures vary, as well as the susceptibility of plant species to infection by *Agrobacterium* (Toivounen et al. 1993; Vanhala et al. 1995). It is known that the *Agrobacterium* strain used for transformation has a great influence on root morphology and the degree of secondary metabolite accumulation in hairy root cultures. It is possible by systematic clone selection, e.g., via protoplasts, to find high yielding, stable, and from single-cell-derived hairy root clones. This is possible because the hairy root cultures possess a great somaclonal variation. Another possibility of transformation is the use of viral vectors (Turpen 1999).

Any plant tissue or plant cells capable of subsequent clonal propagation, whether by organogenesis or embryogenesis, may be transformed with an expression vector of interest. The team "organogenesis" means a process by which shoots and roots are developed sequentially from meristematic centers; the term "embryogenesis" means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include protoplasts, leaf disks, pollen, embryos, cotyledons, hypocotyls, megagametophytes, callus tissue, existing meristematic tissue (e.g., apical meristems, axillary buds, and root meristems), and induced meristem tissue (e.g., cotyledon meristem and hypocotyls meristem).

According to a particularly preferred embodiment, the "yeast cell," as used herein in any of the above-described methods, is a genetically engineered yeast cell, such as a yeast cell expressing an exogenous regulatory or biosynthetic enzyme of the sapogenin biosynthesis pathway (see also Tables 2 and 3). Preferably, the genetically engineered yeast cell is overexpressing an oxidosqualene cyclase (EC 5.4.99.-) and/or a cytochrome P450 (EC 1.14.-). According to a particular embodiment, the "genetically engineered yeast cell," as used herein in any of the above-described methods, is overexpressing a cytochrome P450, which is capable of hydroxylating a carbon at position 21 of an oleanane-type backbone as pictured in FIG. 10. According to a preferred embodiment, the genetically engineered yeast cell as used in any of the above-described methods is overexpressing SEQ ID NO:3 or 4, or fragments or variants thereof (as described further herein).

According to a further preferred embodiment, the genetically engineered yeast cell as used is deficient in expression and/or activity of an enzyme involved in endogenous sterol synthesis. For example, and without the purpose of being limitative, key enzymes in the yeast ergosterol biosynthetic pathway may be down-regulated, in particular, the lanosterol synthase gene (EC 5.4.99.7) to enable maximal and controllable flux toward the heterologous production of the desired triterpenoid sapogenin compounds.

The term "endogenous" as used herein, refers to substances (e.g., genes) originating from within an organism, tissue, or cell. Analogously, "exogenous" as used herein, is any material originated outside of an organism, tissue, or cell, but that is present (and typically can become active) in that organism, tissue, or cell.

Table 2. Overview of oxidosqualene cyclase (OSCs) reported in the literature as involved in sapogenin biosynthesis. 2,3-Oxidosqualene cyclization products identified to emerge from the activity of the corresponding OSC are indicated in squared brackets: aa—α-amyrin, ba—β-amyrin, bau—baurenol, da—damyrin, dam—dammarenediol, fri—friedelin, ge—germanicol, glu—glutinol, isotir—isotirucallol, lu—lupeol, lud—lupane-3β,20-diol, tir—tirucalla-7,24-dien-3β-ol, minor—additional byproducts either reported to be of minor appearance or to represent <10% of the observed products (Table 2 derived from Augustin et al. 2011).

| Name | GenBank ID | Plant species | Product |
|---|---|---|---|
| Accurate b-amyrin synthases | | | |
| AaBAS | ACA13386 | *A. annua* | [ba] |
| AsOXA1 | AAX14716 | *A. sedifolius* | [ba] |
| AsbAS1 | CAC84558 | *A. strigosa* | [ba] |
| BgbAS | BAF80443 | *B. gymnorhiza* | [ba] |
| BPY | BAB83088 | *B. platyphylla* | [ba] |
| EtAS | BAE43642 | *E. tirucalli* | [ba] |
| GgbAS1 | BAA89815 | *G. glabra* | [ba] |
| GsAS1 | ACO24697 | *G. straminea* | [ba] |
| cOSC1 | BAE53429 | *L. japonicus* | [ba] |
| b-AS = MtAMY1 | CAD23247 | *M. truncatula* | [ba] |

-continued

| Name | GenBank ID | Plant species | Product |
| --- | --- | --- | --- |
| NsbAS1 | ACH88048 | N. sativa | [ba] |
| PNY | BAA33461 | P. ginseng | [ba] |
| PNY2 | BAA33722 | P. ginseng | [ba] |
| PSY | BAA97558 | P. sativum | [ba] |
| SlTTS1 | ADU52574 | S. lycopersicum | [ba] |
| SvBS | ABK76265 | S. vaccaria | [ba] |
| Accurate lupeol synthases | | | |
| BgLUS | BAF80444 | B. gymnorhiza | [lu] |
| BPW | BAB83087 | B. platyphylla | [lu] |
| GgLUS1 | BAD08587 | G. glabra | [lu] |
| cOSC3 | BAE53430 | L. japonicus | [lu] |
| OEW | BAA86930 | O. europaea | [lu] |
| RcLUS | ABB76766 | R. communis | [lu] |
| TRW | BAA86932 | T. officinale | [lu] |
| Accurate dammarenediol synthases | | | |
| CaDDS | AAS01523 | C. asiatica | [dam] |
| PNA = DDS | BAF33291 | P. ginseng | [dam] |
| DDS = PNA | ACZ71036 | P. ginseng | [dam] |
| Multifunctional OSCs | | | |
| LUP1/At1g78970 | NP_178018 | A. thaliana | [lu/lud + 4 minor] |
| LUP5/At1g66960 | NP_176868 | A. thaliana | [tir/isotir + 4] |
| PEN6/At1g78500 | NP_177971 | A. thaliana | [lu/bau/aa + 5] |
| CsOSC2/CSV | BAB83254 | C. speciosus | [ba/ge/lu + add.] |
| LjAMY2 | AAO33580 | L. japonicus | [ba/lu + 1 minor] |
| KcMS | BAF35580 | K. candel | [lu/ba/aa] |
| KdGLS | ADK35124 | K. daigremontiana | [glu/fri/ba + 1] |
| OEA | BAF63702 | O. europaea | [aa/ba + 3minor] |
| PSM | BAA97559 | P. sativum | [aa/ba + 6minor] |
| RsM1 | BAF80441 | R. stylosa | [ge/ba + 1 minor] |
| SlTTS2 | ADU52575 | S. lycopersicum | [da/aa/ba + 4 minor] |

TABLE 3

Overview of CYPs reported in the literature as involved in sapogenin biosynthesis.

| Name | GenBank ID | Plant species | Reference |
| --- | --- | --- | --- |
| CYP51H10 | ABG88965 | A. strigosa | (Kunii et al., 2012) |
| CYP716A12 | FN995113 | M. truncatula | (Carelli et al., 2011) |
| CYP716A15 | BAJ84106 | V. vinifera | (Fukushima et al., 2011) |
| CYP716A17 | BAJ84107 | V. vinifera | (Fukushima et al., 2011) |
| CYP716AL1 | FN995113 | C. roseus | (Huang et al., 2012) |
| CYP716A47 | AEY75212 | P. ginseng | (Han et al., 2011) |
| CYP716A53v2 | AFO63031 | P. ginseng | (Han et al., 2012) |
| CYP72A61v2 | BAL45199 | M. truncatula | (Fukushima et al., 2013) |
| CYP72A63 | AB558146 | M. truncatula | (Seki et al., 2011) |
| CYP72A68v2 | BAL45204 | M. truncatula | (Fukushima et al., 2013) |
| CYP72A154 | AB558153 | G. uralensis | (Seki et al., 2011) |
| CYP88D6 | AB433179 | G. uralensis | (Seki et al., 2008) |
| CYP93E1 | NM_001249225 | G. max | (Shibuya et al., 2006) |
| CYP93E2 | DQ335790 | M. truncatula | (Li et al., 2007) |
| CYP93E3 | AB437320 | G. uralensis | (Seki et al., 2008) |

Suitable cell culture media for eukaryotic cells, in particular, plant cells and microbial cells, are known in the art. For plant cells, exemplary media include standard growth media, many of which are commercially available (e.g., Sigma Chemical Co., St. Louis, Mo.). Examples include Schenk-Hildebrandt (SH) medium, Linsmaier-Skoog (LS) medium, Murashige and Skoog (MS) medium, Gamborg's B5 medium, Nitsch & Nitsch medium, White's medium, and other variations and supplements well known to those of skill in the art (see, e.g., Plant Cell Culture, Dixon, ed. IRL Press, Ltd. Oxford (1985); and George et al., Plant Culture Media, Vol. 1, Formulations and Uses Exegetics Ltd. Wilts, UK, (1987)). (See, e.g., Plant Cell Culture, Dixon, ed. IRL Press, Ltd. Oxford (1985); and George et al., Plant Culture Media, Vol. 1, Formulations and Uses Exegetics Ltd. Wilts, UK, (1987)).

For yeast cells, exemplary media include standard growth media, many of which are commercially available (e.g., Clontech, Sigma Chemical Co., St. Louis, Mo.). Examples include Yeast Extract Peptone Dextrose (YPD or YPED) medium, Yeast Extract Peptone Glycerol (YPG or YPEG) medium, Hartwell's complete (HC) medium, Synthetic complete (SC) medium, Yeast Nitrogen Base (YNB), and other variations and supplements well known to those of skill in the art (see, Yeast Protocol Handbook, Clontech).

The incubation conditions (temperature, photoperiod, shaking, auxin/cytokine hormone ratio, promoter-inducing conditions, promoter-repressing conditions, etc.) will depend, among other factors, on the cells to be incubated and are standard techniques in the art. In a particular embodiment, the current disclosure can be combined with other known methods to enhance the production and/or the secretion of triterpenoid sapogenin production in eukaryotic cell cultures, for example (1) by improvement of the cell culture conditions, (2) by metabolic engineering, (3) by the addition of specific elicitors to the cell culture.

Preferably, the eukaryotic cell is induced before it produces secondary metabolites such as triterpenoid sapogenins, meaning that the cell culture is stimulated by the addition of an external factor. External factors include the application of heat, the application of cold, the addition of acids, bases, metal ions, fungal membrane proteins, sugars and the like. In the case of plants, it is demonstrated that better production of plant secondary metabolites occurs via elicitation. Elicitors are compounds capable of inducing defense responses in plants. These are usually not found in intact plants but their biosynthesis is induced after wounding or stress conditions. Commonly used elicitors are jasmonates, mainly jasmonic acid and its methyl ester, methyl jasmonate. Jasmonates are linoleic acid derivatives of the plasma membrane and display a wide distribution in the plant kingdom. They were originally classified as growth inhibitors or promoters of senescence but now it has become apparent that they have pleiotropic effects on plant growth and development. Jasmonates appear to regulate cell division, cell elongation and cell expansion and thereby stimulate organ or tissue formation. They are also involved in the signal transduction cascades that are activated by stress situations such as wounding, osmotic stress, desiccation and pathogen attack. Methyl jasmonate (MeJA) is known to induce the accumulation of numerous defense-related secondary metabolites through the induction of genes coding for the enzymes involved in the biosynthesis of these compounds in plants. Jasmonates can modulate gene expression from the (post)transcriptional to the (post)translational level, both in a positive as well as in a negative way. Genes that are up-regulated are, e.g., defense- and stress-related genes (PR proteins and enzymes involved with the synthesis of phytoalexins and other secondary metabolites), whereas the activity of housekeeping proteins and genes involved with photosynthetic carbon assimilation are down-regulated. For example: the biosynthesis of phytoalexins and other secondary products in plants can also be boosted up by signal molecules derived from microorganisms or plants (such as peptides, oligosaccharides, glycopeptides, salicylic acid and lipophilic substances), as well as by various abiotic elicitors like UV-light, heavy metals (Cu, $VOSO_4$, Cd) and ethylene. The effect of any elicitor is dependent on a number of factors, such as the specificity of an elicitor, elicitor concentration, the duration of the treatment and growth stage of the culture.

A number of suitable culture media for callus induction and subsequent growth on aqueous or solidified media are known. Exemplary media include standard growth media, many of which are commercially available (e.g., Sigma Chemical Co., St. Louis, Mo.). Examples include Schenk-Hildebrandt (SH) medium, Linsmaier-Skoog (LS) medium, Murashige and Skoog (MS) medium, Gamborg's B5 medium, Nitsch & Nitsch medium, White's medium, and other variations and supplements well known to those of skill in the art During or after the sapogenin production in the growth medium of a eukaryotic cell culture, according to any of the above described methods, the sapogenins can be extracted from the cells. According to a preferred embodiment, the sapogenins are extracted from the culture medium wherein the sapogenins are secreted. Accordingly, the methods of producing sapogenins may optionally also comprise the step of extracting the sapogenins from the culture medium. Eventually, the sapogenins may also be further purified. Means that may be employed to this end are known to the skilled person. Generally, triterpenoid sapogenins can be measured intracellularly or in the extracellular space by methods known in the art. Such methods comprise analysis by thin-layer chromatography, high-pressure liquid chromatography, capillary electrophoresis, gas chromatography combined with mass spectrometric detection, radioimmunoassay (RIA) and enzyme immuno-assay (ELISA). For example, *Medicago* triterpene sapo(ge)nin content can be analyzed by reverse-phase UPLC/ICR/FT-MS, and is also further illustrated in the Examples section.

In a further aspect, the disclosure also provides a eukaryotic cell genetically engineered to synthesize sapogenins and/or pathway intermediates. In particular, the genetically engineered cell is a yeast cell, for example a *Saccharomyces, Schizosaccharomyces, Pichia, Yarrowia, Candida* or *Hansenula* cell. According to a particularly preferred embodiment, the yeast cell is genetically engineered to express an exogenous regulatory or biosynthetic enzyme of the sapogenin biosynthesis pathway (see also Tables 2 and 3). Preferably, the yeast cell is genetically engineered to overexpress an oxidosqualene cyclase (EC 5.4.99.-) and/or a cytochrome P450 (EC 1.14.-). According to a particular embodiment, the yeast cell is genetically engineered to overexpress a cytochrome P450, which is capable of hydroxylating a carbon at position 21 of an oleanane-type backbone as pictured in FIG. 10. According to a preferred embodiment, the yeast cell is genetically engineered to overexpress SEQ ID NO:3 or 4, or fragments or variants thereof (as described further herein).

In still another aspect, the disclosure also encompasses existing or novel sapogenins obtained by any of the above-described methods. The sapogenins that are extracellularly accumulating in the growth medium of a eukaryotic cell culture in the presence of cyclodextrins are readily accessible and can be exploited by industry for a variety of purposes, either directly, or after further synthetic chemistry. For example, sapogenins and its derivatives (including saponins) can be used as additives to foods and cosmetics, preservatives, flavor modifiers, agents for removal of cholesterol from dietary products, and may also be very valuable for their pharmacological properties. For example, several saponins and sapogenins are considered to possess activities such as anti-inflammatory, anti-carcinogenic, anti-bacterial, anti-fungal and antiviral effects. Saponins are also of interest as valuable adjuvants and the first saponin-based vaccines are introduced commercially (reviewed in Sun et al. 2009).

Figure 10:
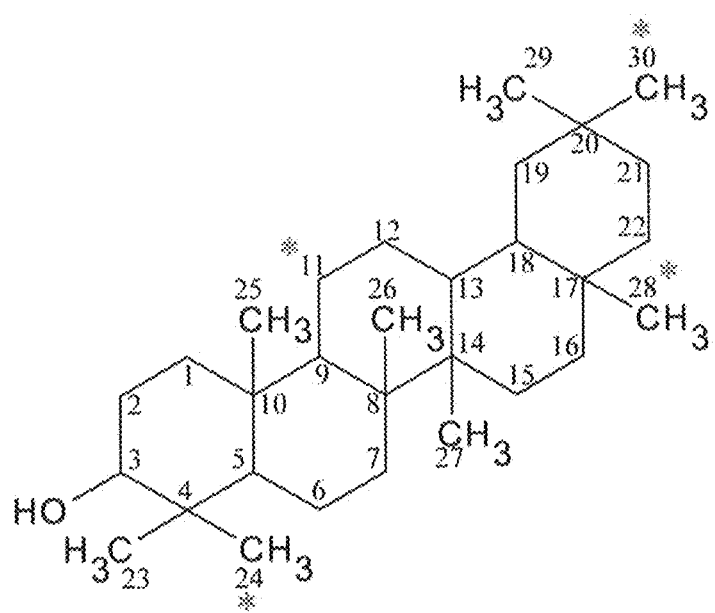
FIG. 10: Chemical structure of oleanane-type sapogenin backbone. Asterisks (*) indicate the carbon positions for which a CytP450 has already been characterized.

In a specific embodiment, sapogenins that are hydroxylated on a carbon at position 21 of an oleanane-type backbone as pictured in FIG. 10 are encompassed here.

According to another aspect, the disclosure relates to an isolated polypeptide selected from the group consisting of:
(a) a polypeptide encoded by a polynucleotide comprising SEQ ID NO:1 or 2;
(b) a polypeptide comprising a polypeptide sequence having at least 75% identity to the polypeptide encoded by a polynucleotide sequence having SEQ ID NO:1 or 2;
(c) a polypeptide comprising an amino acid sequence as set forth in SEQ ID NO:3 or 4;
(d) a polypeptide comprising an amino acid sequence with at least 75% identity to SEQ ID NO:3 or 4;
(e) fragments and/or variants of the polypeptides according to (a), (b), (c), or (d).

In one embodiment, the disclosure relates to any of the above-described polypeptides wherein the polypeptide sequence is consisting of an amino acid sequence as set forth in SEQ ID NO:3 or 4 and polypeptide sequences having at least 75% identity to SEQ ID NO:3 or 4.

According to another aspect, the disclosure relates to an isolated polynucleotide selected from the group consisting of:
(a) a polynucleotide comprising a polynucleotide sequence having the sequence SEQ ID NO:1 or 2;
(b) a polynucleotide comprising a polynucleotide sequence having at least 70% identity to the sequence having SEQ ID NO:1 or 2;
(c) a polynucleotide that encodes the polypeptide sequence as set forth in SEQ ID NO:3 or 4;
(d) a polynucleotide that encodes the polypeptide sequence as set forth in SEQ ID NO:3 or 4;
(e) fragments and variants of the polynucleotides according to (a), (b), (c) or (d).

As used herein, the terms "polypeptide," "protein," and "peptide" are used interchangeably and refer to a polymeric form of amino acids of any length, which can include coded and non-coded amino acids, chemically or biochemically modified or derivatized amino acids, and polypeptides having modified peptide backbones.

As used herein, the terms "nucleic acid," "polynucleotide," and "polynucleic acid" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The polynucleotide molecule may be linear or circular. The polynucleotide may comprise a promoter, an intron, an enhancer region, a polyadenylation site, a translation initiation site, 5' or 3' untranslated regions, a reporter gene, a selectable marker or the like. The polynucleotide may comprise single-stranded or double-stranded DNA or RNA. The polynucleotide may comprise modified bases or a modified backbone. A nucleic acid that is up to about 100 nucleotides in length, is often also referred to as an oligonucleotide.

An "isolated polypeptide" or an "isolated polynucleotide," as used herein, refers to, respectively, an amino acid sequence or a polynucleotide sequence that is not naturally occurring or no longer occurring in the natural environment wherein it was originally present.

As used herein, the terms "identical" or "percent identity," in the context of two or more nucleic acids or polypeptide sequences, refer to two or more sequences or subsequences that are the same or have a specified percentage of amino acid residues or nucleotides that are the same (e.g., 75% identity over a specified region), when compared and aligned for maximum correspondence over a comparison window or designated region as measured using sequence comparison algorithms or by manual alignment and visual inspection. Preferably, the identity exists over a region that is at least about 25 amino acids or nucleotides in length, or, more preferably, over a region that is 50-100 amino acids or nucleotides or even more in length. According to preferred embodiments, the disclosure relates to an isolated polypeptide comprising a polypeptide sequence having at least 75%, at least 80%, at least 85%, at least 90%, at least 95%, at least 96%, at least 97%, at least 98% or at least 99% identity to the polypeptide encoded by a polynucleotide sequence having SEQ ID NO:1 or 2, or having at least 75%, at least 80%, at least 85%, at least 90%, at least 95%, at least 96%, at least 97%, at least 98% or at least 99% identity to a polypeptide comprising an amino acid sequence as set forth in SEQ ID NO:3 or 4. In other preferred embodiments, the disclosure relates to an isolated polynucleotide comprising a polynucleotide sequence having at least 70%, at least 75%, at least 80%, at least 85%, at least 90%, at least 95%, at least 96%, at least 97%, at least 98% or at least 99% identity to the sequence having SEQ ID NO:1 or 2.

In a particular embodiment, fragments and variants of any of the above polynucleotides or polypeptides also form part of this disclosure.

In reference to a nucleotide sequence, "a fragment" refers to any sequence of at least 15 consecutive nucleotides, preferably at least 30 consecutive nucleotides, more preferably at least 50, 60, 70, 80, 90, 100, 150, 200 consecutive nucleotides or more, of any of the sequences provided herein. If desired, the fragment may be fused at either terminus to additional base pairs, which may number from 1 to 20, typically 50 to 100, but up to 250 to 500 or more.

A "fragment," as referred to polypeptides, refers to a subsequence of the polypeptide. Fragments may vary in size from as few as five amino acids to the length of the intact polypeptide, but are preferably at least 10, 15, 20, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75 amino acids in length. If desired, the fragment may be fused at either terminus to additional amino acids, which may number from 1 to 20, typically 50 to 100, but up to 250 to 500 or more. A "functional fragment" means a polypeptide fragment possessing the ability to hydroxylate a carbon at position 21 of an oleanane-type backbone as pictured in FIG. 10.

A "variant" as used herein refers to homologs, orthologs and paralogs and include, but are not limited to, homologs, orthologs and paralogs of SEQ ID NOS:1-4. Homologs of a protein encompass peptides, oligopeptides and polypeptides having amino acid substitutions, deletions and/or insertions, preferably by a conservative change, relative to the unmodified protein in question and having similar biological and functional activity as the unmodified protein from which they are derived; or in other words, without significant loss of function or activity. Orthologs and paralogs, which are well-known terms by the skilled person, define subcategories of homologs and encompass evolutionary concepts used to describe the ancestral relationships of genes. Paralogs are genes within the same species that have originated through duplication of an ancestral gene; orthologs are genes from different organisms that have originated through speciation, and are also derived from a common ancestral gene. Several different methods are known by those of skill in the art for identifying and defining these functionally homologous sequences. General methods for identifying orthologues and paralogues include phylogenetic methods, sequence similarity and hybridization methods. Percentage similarity and identity can be determined electronically. Examples of useful algorithms are PILEUP (Higgins & Sharp, CABIOS 5:151 (1989)), BLAST and BLAST 2.0 (Altschul et al., *J. Mol. Biol.* 215:403 (1990); software for performing BLAST analyses is publicly available through the National Center for Biotechnology Information (http://www.ncbi.nlm.nih.gov/)). Preferably, the homologue, orthologue or paralogue has a sequence identity at a protein level of at least 50%, preferably 60%, more preferably 70%, even more preferably 80%, most preferably 90% as measured in a BLASTp.

Further, it will be appreciated by those of skill in the art, that any of a variety of polynucleotide sequences are capable of encoding the polypeptides of the disclosure. Due to the degeneracy of the genetic code, many different polynucleotides can encode identical and/or substantially similar polypeptides. Sequence alterations that do not change the amino acid sequence encoded by the polynucleotide are termed "silent" variations. With the exception of the codons ATG and TGG, encoding methionine and tryptophan, respectively, any of the possible codons for the same amino acid can be substituted by a variety of techniques, e.g., site-directed mutagenesis, available in the art. Accordingly, any and all such variations of a sequence are a feature of the disclosure. In addition to silent variations, other conservative variations that alter one, or a few amino acids in the encoded polypeptide, can be made without altering the function of the polypeptide (i.e., enhanced secondary metabolite production, in the context of the disclosure), these conservative variants are, likewise, a feature of the disclosure.

Conservative substitutions or variations, as used herein, are those in which at least one residue in the amino acid sequence has been removed and a different residue inserted in its place. Such substitutions generally are made in accordance with the table depicted below. This table shows amino acids that can be substituted for an amino acid in a protein and that are typically regarded as conservative substitutions.

| Residue | Conservative Substitutions |
| --- | --- |
| Ala | Ser |
| Arg | Lys |
| Asn | Gln, His |
| Asp | Glu |
| Gln | Asn |
| Cys | Ser |
| Glu | Asp |
| Gly | Pro |
| His | Asn, Gln |
| Ile | Leu, Val |
| Leu | Ile, Val |
| Lys | Arg, Gln |
| Met | Leu, Ile |
| Phe | Met, Leu, Tyr |
| Ser | Thr, Gly |
| Thr | Ser, Val |
| Trp | Tyr |
| Tyr | Trp, Phe |
| Val | Ile, Leu |

Substitutions that are less conservative than those in the above table can be selected by picking residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that, in general, are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

Substitutions, deletions and insertions introduced into the sequences are also envisioned by the disclosure. Such sequence modifications can be engineered into a sequence by site-directed mutagenesis or the other methods known in the art. Amino acid substitutions are typically of single residues; insertions usually will be on the order of from about one to ten amino acid residues; and deletions will range from about one to thirty residues. In preferred embodiments, deletions or insertions are made in adjacent pairs, e.g., a deletion of two residues or insertion of two residues. Substitutions, deletions, insertions or any combination thereof can be combined to arrive at a sequence. The mutations that are made in the polynucleotides of the disclosure should not create complementary regions that could produce secondary mRNA structure. Preferably, the polypeptide encoded by the DNA performs the desired function (i.e., hydroxylating a carbon at position 21 of an oleanane-type backbone as pictured in FIG. 10, in the context of this disclosure).

In a specific embodiment, the disclosure relates to a chimeric gene comprising the following operably linked sequences: a) a promoter region capable of directing expression in a eukaryotic cell (as defined hereinbefore); b) a DNA region encoding a polypeptide as defined above; and c) a 3' polyadenylation and transcript termination region.

The term "operably linked" as used herein refers to a linkage in which the regulatory sequence is contiguous with the gene of interest to control the gene of interest, as well as regulatory sequences that act in trans or at a distance to control the gene of interest. For example, a DNA sequence is operably linked to a promoter when it is ligated to the promoter downstream with respect to the transcription initiation site of the promoter and allows transcription elongation to proceed through the DNA sequence. A DNA for a signal sequence is operably linked to DNA coding for a polypeptide if it is expressed as a pre-protein that participates in the transport of the polypeptide. Linkage of DNA sequences to regulatory sequences is typically accomplished by ligation at suitable restriction sites or adapters or linkers inserted in lieu thereof using restriction endonucleases known to one of skill in the art.

The term "regulatory sequence" as used herein refers to polynucleotide sequences that are necessary to affect the expression of coding sequences to which they are operably linked. Expression control sequences are sequences that control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism. The term "control sequences" is intended to include, at a minimum, all components whose presence is essential for expression, and can also include additional components whose presence is advantageous, for example, leader sequences and fusion partner sequences.

A vector comprising a polynucleotide sequence or a chimeric gene as defined above also forms part of the disclosure, as well as a host cell comprising a polynucleotide sequence or a chimeric gene or a vector as defined above.

The term "vector" as used herein is intended to refer to a nucleic acid molecule capable of transporting another nucleic acid molecule to which it has been linked. The vector may be of any suitable type including, but not limited to, a phage, virus, plasmid, phagemid, cosmid, bacmid or even an artificial chromosome. Certain vectors are capable of autonomous replication in a host cell into which they are introduced (e.g., vectors having an origin of replication that functions in the host cell). Other vectors can be integrated into the genome of a host cell upon introduction into the host cell, and are thereby replicated along with the host genome. Moreover, certain preferred vectors are capable of directing the expression of certain genes of interest. Such vectors are referred to herein as "recombinant expression vectors" (or simply, "expression vectors"). Suitable vectors have regulatory sequences, such as promoters, enhancers, terminator sequences, and the like as desired and according to a particular host organism (e.g., plant cell). Typically, a recombinant vector according to the disclosure comprises at least one "chimeric gene" or "expression cassette." Expression cassettes are generally DNA constructs preferably including (5' to 3' in the direction of transcription): a promoter region, a polynucleotide sequence, homologue, variant or fragment thereof of the disclosure operably linked with the transcription initiation region, and a termination sequence including a stop signal for RNA polymerase and a polyadenylation signal. It is understood that all of these regions should be capable of operating in biological cells, such as plant cells, to be transformed. The promoter region comprising the transcription initiation region, which preferably includes the RNA polymerase binding site, and the polyadenylation signal may be native to the biological cell to be transformed or may be derived from an alternative source, where the region is functional in the biological cell.

The term "recombinant host cell" ("expression host cell," "expression host system," "expression system" or simply "host cell"), as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell that resides in a living tissue or organism. Host cells can be of bacterial, fungal, plant or mammalian origin.

According to yet another aspect, the disclosure provides a transgenic plant or a cell derived thereof that is transformed with the above-described vector.

The term "plant" as used herein refers to vascular plants (e.g., gymnosperms and angiosperms). A "transgenic plant" refers to a plant comprising a recombinant polynucleotide and/or a recombinant polypeptide according to the disclosure. A transgenic plant refers to a whole plant as well as to a plant part, such as seed, fruit, leaf, or root, plant tissue, plant cells or any other plant material, and progeny thereof. A transgenic plant can be obtained by transforming a plant cell with an expression cassette of the disclosure and regenerating such plant cell into a transgenic plant. Such plants can be propagated vegetatively or reproductively. The transforming step may be carried out by any suitable means, including by *Agrobacterium*-mediated transformation and non-*Agrobacterium*-mediated transformation, as discussed in detail below. Plants can be regenerated from the transformed cell (or cells) by techniques known to those skilled in the art. Where chimeric plants are produced by the process, plants in which all cells are transformed may be regenerated from chimeric plants having transformed germ cells, as is known in the art. Methods that can be used to transform plant cells or tissue with expression vectors of the disclosure include both *Agrobacterium* and non-*Agrobacterium* vectors. *Agrobacterium*-mediated gene transfer exploits the natural ability of *Agrobacterium tumefaciens* to transfer DNA into plant chromosomes and is described in detail in G. Gheysen, G. Angenon, and M. Van Montagu, 1998, *Agrobacterium*-mediated plant transformation: a scientifically intriguing story with significant applications in K. Lindsey (Ed.), *Transgenic Plant Research*, Harwood Academic Publishers, Amsterdam, pp. 1-33; and in H. A. Stafford (2000), *Botanical Review* 66:99-118. A second group of transformation methods is the non-*Agrobacterium*-mediated transformation and these methods are known as direct gene transfer methods. An overview is brought by P. Barcelo and P. A. Lazzeri (1998), Direct gene transfer: chemical, electrical and physical methods in K. Lindsey (Ed.), *Transgenic Plant Research*, Harwood Academic Publishers, Amsterdam, pp. 35-55.

Methods include particle gun delivery, microinjection, electroporation of intact cells, polyethyleneglycol-mediated protoplast transformation, electroporation of protoplasts, liposome-mediated transformation, silicon-whiskers-mediated transformation, etc.

Hairy root cultures can be obtained by transformation with virulent strains of *Agrobacterium rhizogenes*, and they can produce high content of secondary metabolites characteristic to the mother plant. Protocols used for establishing of hairy root cultures vary, as well as the susceptibility of plant species to infection by *Agrobacterium* (Toivounen et al. 1993; Vanhala et al. 1995). It is known that the *Agrobacterium* strain used for transformation has a great influence on root morphology and the degree of secondary metabolite accumulation in hairy root cultures. It is possible by systematic clone selection, e.g., via protoplasts, to find high yielding, stable, and from single-cell-derived hairy root clones. This is possible because the hairy root cultures possess a great somaclonal variation. Another possibility of transformation is the use of viral vectors (Turpen 1999).

Any plant tissue or plant cells capable of subsequent clonal propagation, whether by organogenesis or embryogenesis, may be transformed with an expression vector of the disclosure. The term "organogenesis" means a process by which shoots and roots are developed sequentially from meristematic centers; the term "embryogenesis" means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include protoplasts, leaf disks, pollen, embryos, cotyledons, hypocotyls, megagametophytes, callus tissue, existing meristematic tissue (e.g., apical meristems, axillary buds, and root meristems), and induced meristem tissue (e.g., cotyledon meristem and hypocotyls meristem).

A "control plant" as used in the disclosure refers to a plant cell, seed, plant component, plant tissue, plant organ or whole plant used to compare against transgenic or genetically modified plant for the purpose of identifying a difference in production of sapogenins in the transgenic or genetically modified plant. A control plant may in some cases be a transgenic plant line that comprises an empty vector or marker gene, but does not contain the recombinant polynucleotide of the disclosure that is expressed in the transgenic or genetically modified plant being evaluated. In general, a control plant is a plant of the same line or variety as the transgenic or genetically modified plant being tested. A suitable control plant would include a genetically unaltered or non-transgenic plant of the parental line (wild-type) used to generate a transgenic plant herein.

Plants of the disclosure may include, but are not limited to, plants or plant cells of agronomically important crops that are or are not intended for animal or human nutrition, such as maize or corn, wheat, barley, oat, *Brassica* spp. plants such as *Brassica napus* or *Brassica juncea*, soybean, bean, alfalfa, pea, rice, sugarcane, beetroot, tobacco, sunflower, cotton, *Arabidopsis*, vegetable plants such as cucumber, leek, carrot, tomato, lettuce, peppers, melon, watermelon, diverse herbs such as oregano, basilicum and mint. It may also be applied to plants that produce valuable compounds, e.g., useful as, for instance, pharmaceuticals, as ajmalicine, vinblastine, vincristine, ajmaline, reserpine, rescinnamine, camptothecine, ellipticine, quinine, and quinidine, taxol, morphine, scopolamine, atropine, cocaine, sanguinarine, codeine, genistein, daidzein, digoxinu, calystegins or as food additives such as anthocyanins, and vanillin, including, but not limited to, the classes of compounds mentioned above. Examples of such plants include, but not limited to, *Papaver* spp., *Rauwolfia* spp., *Taxus* spp., *Cinchona* spp., *Eschscholtzia californica*, *Camptotheca acuminata*, *Hyoscyamus* spp., *Berberis* spp., *Coptis* spp., *Datura* spp., *Atropa* spp., *Thalictrum* spp., *Peganum* spp. Preferred members of the genus *Taxus* comprise *Taxus brevifolia, Taxus baccata, Taxus cuspidata, Taxus canadensis* and *Taxus floridana*.

The polynucleotide sequence, homologue, variant or fragment thereof of the disclosure may be expressed in, for example, a plant cell under the control of a promoter that directs constitutive expression or regulated expression. Regulated expression comprises temporally or spatially regulated expression and any other form of inducible or repressible expression. Temporally means that the expression is induced at a certain time point, for instance, when a certain growth rate of the plant cell culture is obtained (e.g., the promoter is induced only in the stationary phase or at a certain stage of development). Spatially means that the promoter is only active in specific organs, tissues, or cells (e.g., only in roots, leaves, epidermis, guard cells or the like). Other examples of regulated expression comprise promoters whose activity is induced or repressed by adding chemical or physical stimuli to the plant cell. In a preferred embodiment, the expression is under control of environmental, hormonal, chemical, and/or developmental signals. Such promoters for plant cells include promoters that are regulated by (1) heat, (2) light, (3) hormones, such as abscisic acid, and methyl jasmonate (4) wounding or (5) chemicals such as salicylic acid, chitosans or metals. Indeed, it is well known that the expression of secondary metabolites can be boosted by the addition of, for example, specific chemicals, jasmonate and elicitors. In a particular embodiment, the co-expression of several (more than one) polynucleotide sequences or homologues or variants or fragments thereof, in combination with the induction of secondary metabolite synthesis, is beneficial for an optimal and enhanced production of secondary metabolites. Alternatively, the at least one polynucleotide sequence, homologue, variant or fragment thereof is placed under the control of a constitutive promoter. A constitutive promoter directs expression in a wide range of cells under a wide range of conditions. Examples of constitutive plant promoters useful for expressing heterologous polypeptides in plant cells include, but are not limited to, the cauliflower mosaic virus (CaMV) 35S promoter, which confers constitutive, high-level expression in most plant tissues including monocots, the nopaline synthase promoter and the octopine synthase promoter. The expression cassette is usually provided in a DNA or RNA construct that is typically called an "expression vector," which is any genetic element, e.g., a plasmid, a chromosome, a virus, behaving either as an autonomous unit of polynucleotide replication within a cell (i.e., capable of replication under its own control) or being rendered capable of replication by insertion into a host cell chromosome, having attached to it another polynucleotide segment, so as to bring about the replication and/or expression of the attached segment. Suitable vectors include, but are not limited to, plasmids, bacteriophages, cosmids, plant viruses and artificial chromosomes. The expression cassette may be provided in a DNA construct, which also has at least one replication system. In addition to the replication system, there will frequently be at least one marker present, which may be useful in one or more hosts, or different markers for individual hosts. The markers may a) code for protection against a biocide, such as antibiotics, toxins, heavy metals, certain sugars or the like; b) provide complementation, by imparting prototrophy to an auxotrophic host; or c) provide a visible phenotype through the production of a novel compound in the plant. Exemplary genes that may be employed include neomycin phosphotransferase (NPTII), hygromycin phosphotransferase (HPT), chloramphenicol acetyltransferase (CAT), nitrilase, and the gentamicin resistance gene. For plant host selection, non-limiting examples of suitable markers are β-glucuronidase, providing indigo production, luciferase, providing visible light production, Green Fluorescent Protein and variants thereof, NPTII, providing kanamycin resistance or G418 resistance, HPT, providing hygromycin resistance, and the mutated aroA gene, providing glyphosate resistance.

The term "promoter activity" refers to the extent of transcription of a polynucleotide sequence, homologue, variant or fragment thereof that is operably linked to the promoter whose promoter activity is being measured. The promoter activity may be measured directly by measuring the amount of RNA transcript produced, for example, by Northern blot or indirectly by measuring the product coded for by the RNA transcript, such as when a reporter gene is linked to the promoter.

According to a further aspect of the disclosure, the above-described polynucleotide sequences (and encoded proteins) can be used for the biosynthesis of (novel) triterpenoid sapogenin compounds. To illustrate this further, without the purpose of being limitative, one is referred to the Examples section below.

The following examples are intended to promote a further understanding of the disclosure. While this disclosure is described herein with reference to illustrated embodiments, it should be understood that the disclosure is not limited hereto. Those having ordinary skill in the art and access to the teachings herein will recognize additional modifications and embodiments within the scope thereof. Therefore, the disclosure is limited only by the claims attached herein.

EXAMPLES

I. Introduction

Example 1. Triterpenoid Sapogenins in Plant Cultures

In an attempt to detect triterpenoid sapogenins from plant cultures, hairy roots of the model legume *Medicago truncatula* transformed with a GATEWAY™ plasmid pK7WG2D-GUS, containing a non-functional β-glucuronidase gene (GUS) expressed from a $^{35}$S promoter (Pollier et al., 2011) were analyzed. The hairy roots were grown for three weeks in 30 ml Murashige and Skoog basal salt mixture including vitamins (Duchefa) prior to an organic extraction and gas chromatography-mass spectrometry (GC-MS) analysis. The roots were harvested from the culture medium, frozen in liquid nitrogen and ground to a fine powder. A total metabolite extraction was performed on this ground material using 1 ml of methanol. The methanol phase was evaporated to dryness and the subsequent pellet was extracted with 1 ml hexane, since the triterpenoid sapogenins are extremely hydrophobic in nature. The hexane phase was separated from the undissolved residue, evaporated to dryness and trimethylsilylated as described (Radosevich et al. 1985). This derivatized material was subjected to GC-MS (GC model 6890, MS model 5973, Agilent) analysis where, a 1 µl aliquot was injected in splitless mode into a VF-5 ms capillary column (VARIAN® CP9013, Agilent) and operated at a constant helium flow of 1 ml/minute. The injector temperature was set to 280° C. and the oven temperature was held at 80° C. for 1 minute post-injection, ramped to 280° C. at 20° C./minute, held at 280° C. for 45 minutes, ramped to 320° C. at 20° C./minute, held at 320° C. for 1 minute, and finally cooled down to 80° C. at 50° C./minute at the end of the run. The MS transfer line was set to 250° C., the MS ion source to 230° C., and the quadrupole to 150° C., throughout.

Figure 2:
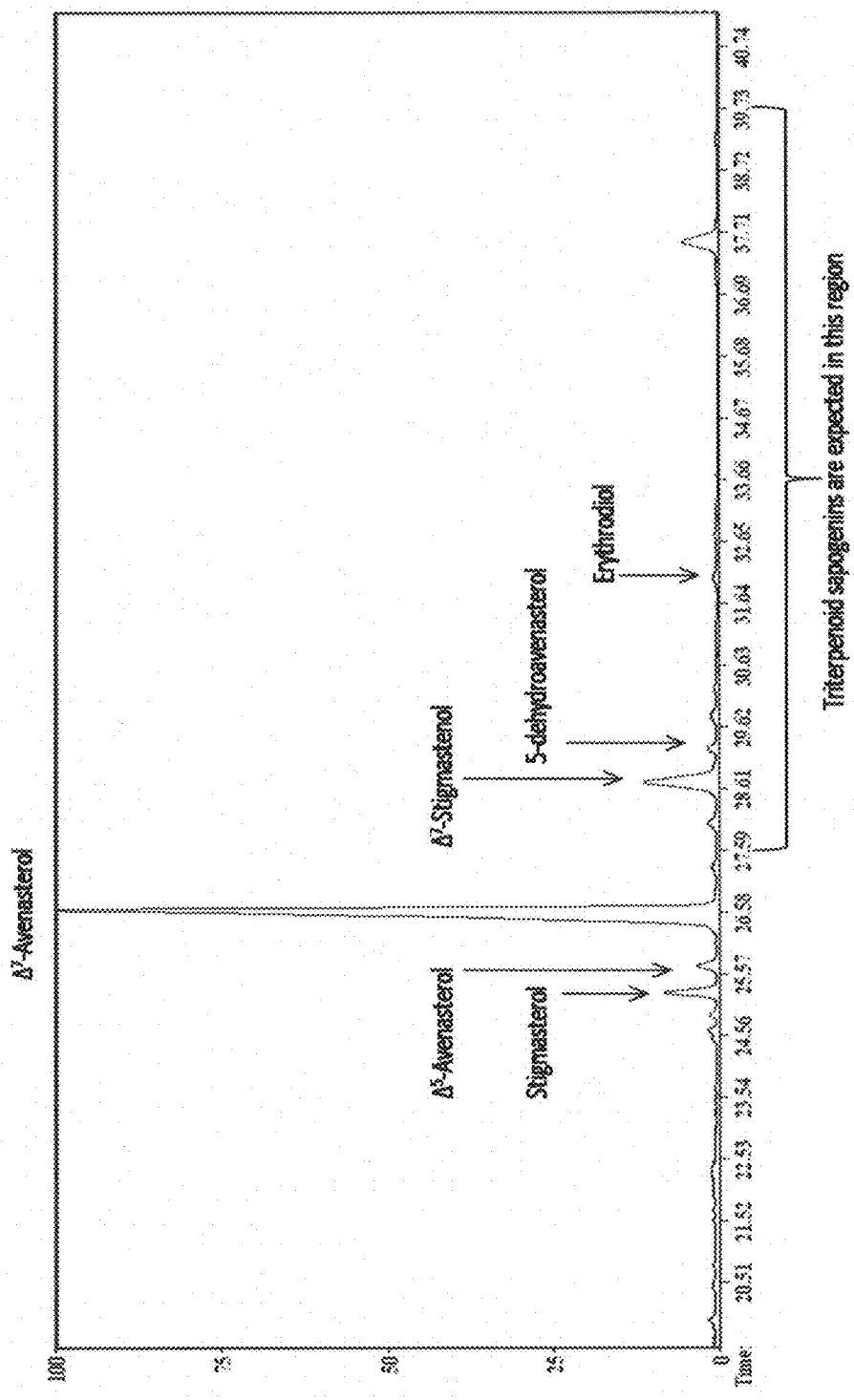
FIG. 2: GC chromatogram of extraction from *M. truncatula* hairy roots showing the presence of abundant sterols and sterol intermediates, but only trace amounts of triterpenoid sapogenins.

Owing to the hydrophobicity of sterols, multiple sterols and sterol intermediates were detected in the GC chromatogram of this extract (FIG. 2). The identity of these compounds was confirmed using the MS electron ionization (EI) pattern described in literature (data not shown). However, only trace amounts of erythrodiol and no other triterpenoid sapogenins were detected in this chromatogram (FIG. 2), emphasizing their low abundance in a glycosyl-free form in the hairy roots. Due to this inability to detect triterpene sapogenins from plant cultures, a yeast strain capable of accumulating detectable amounts of these valuable compounds were engineered.

II. Production of Triterpenoid Sapogenins in Microbial Cultures

Example 2. Generation of Yeast Strain TM1 with Modified Sterol Biosynthesis

Triterpene saponin and sterol biosynthesis depend on the same precursor, i.e., oxidosqualene (FIG. 1). To enable maximal and controllable flux toward the heterologous production of the desired triterpene compounds, the endogenous sterol synthesis of the model yeast *Saccharomyces cerevisiae* was first engineered, which leads to ergosterol as a major compound.

The ergosterol biosynthetic pathway of the *Saccharomyces cerevisiae* strain S288c BY4742 was modified as described (Kirby et al., 2008) with adaptations. The lanosterol synthase gene (ERG7) (GenBank accession number NM_001179202) was made conditionally down-regulatable by replacing the native ERG7 promoter with a methionine-repressible MET3 promoter as described for ERG9 in *S. cerevisiae* CEN.PK 113-7D (Asadollahi et al., 2008), to generate strain TM1. The amount of ergosterol produced by TM1 in the presence of different concentrations of methionine was quantified using the sterol quantification method as described (Arthington-Skaggs et al., 1999). A 60% reduction in ergosterol accumulation was observed in TM1 with 1.5 mM methionine when compared to wild-type cells. Further, a truncated, feedback-uncoupled, copy of isoform 1 of the rate-limiting enzyme 3-hydroxy-3-methylglutaryl-CoA reductase (tHMG1) (GenBank accession number NM_001182434) was generated as described (Polakowski et al., 1998). The tHMG1 was cloned into the multiple cloning site (MCS) 1 of the high copy number plasmid pESC-URA (Agilent Technologies) behind the galactose inducible GAL10 promoter to generate pESC-URA[GAL10/tHMG1], which was transformed into TM1 to generate strain TM5.

Example 3. Generation of β-Amyrin-Producing Yeast Strain TM3

Figure 3:
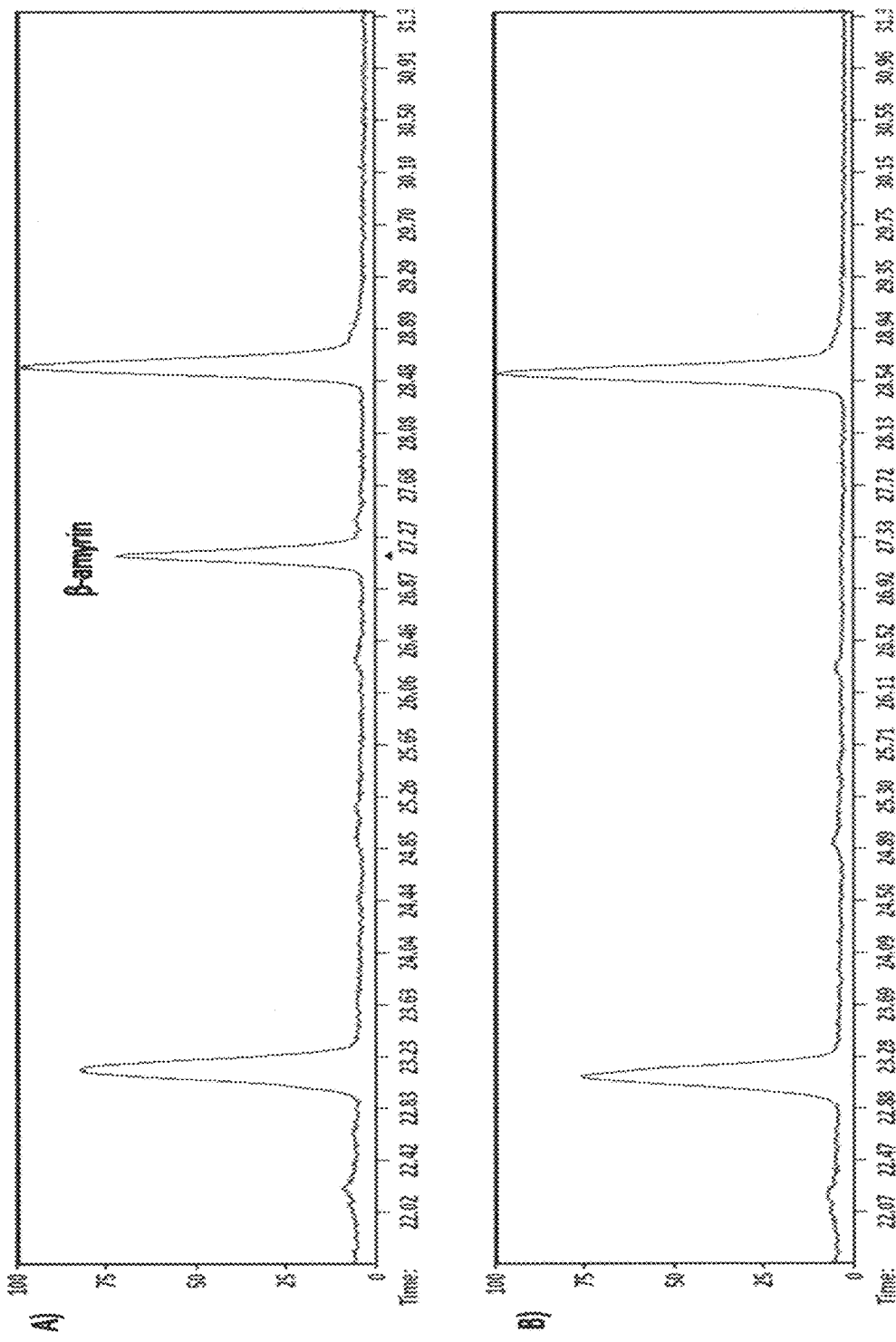
FIG. 3: GC chromatogram of: Panel A) extraction from cells of strain TM3 showing β-amyrin at 27.2 min, Panel B) extraction from spent medium of strain TM3, Panel C) extraction from cells of strain TM5, and Panel D) β-amyrin standard.
Figure 3:
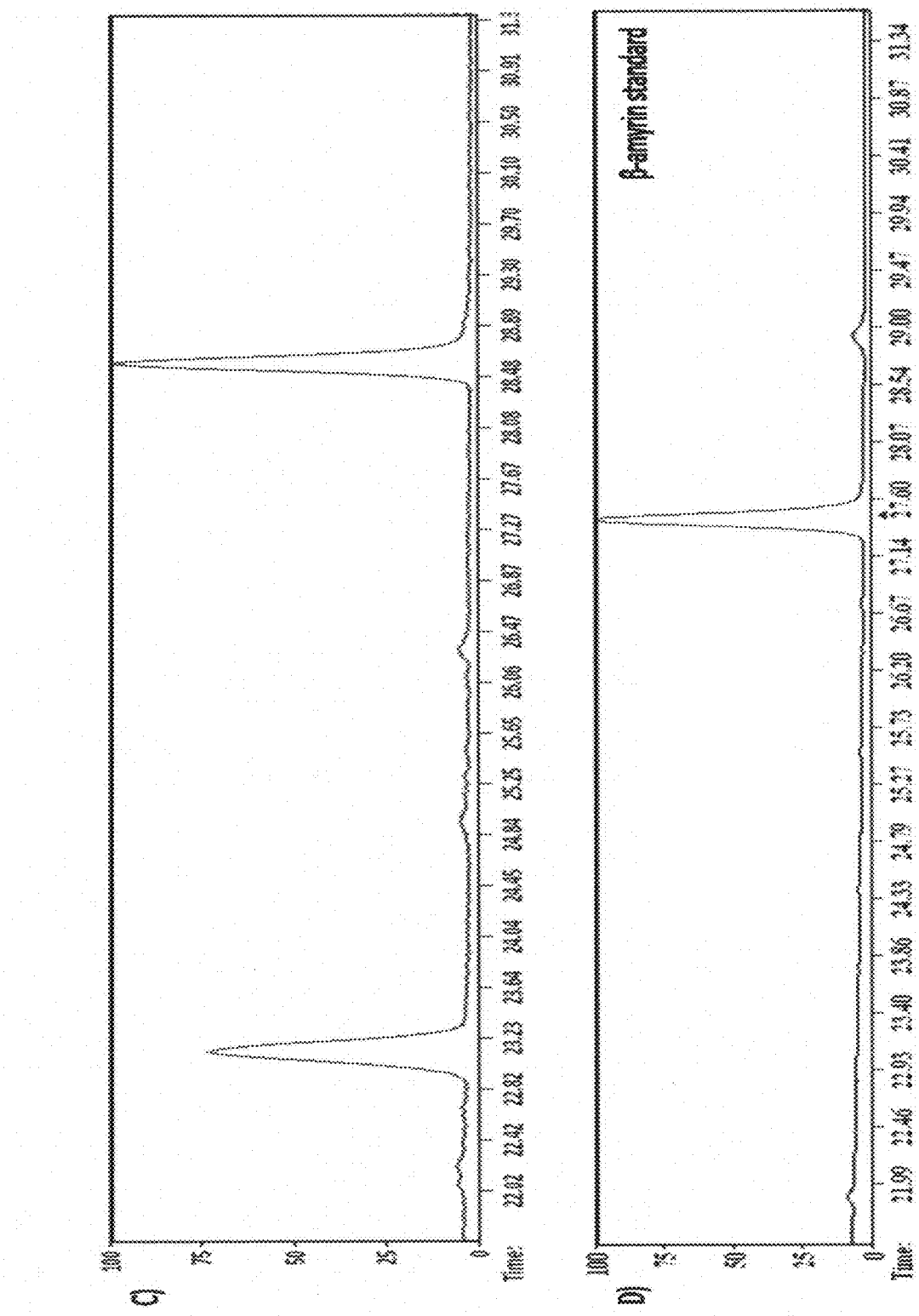

The *Glycyrrhiza glabra* β-amyrin synthase (GgbAS) (GenBank accession number AB037203; (Hayashi et al., 2001)) was cloned into the MCS 2 of plasmid pESC-URA [GAL10/tHMG1] to generate pESC-URA[GAL10/tHMG1; GAL1/bAS]. Strain TM1 was transformed with this plasmid using the lithium acetate-mediated transformation method to generate strain TM3. To validate the production of β-amyrin in TM3, strains TM3 and TM5 were first precultured in minimal synthetic defined (SD) base-containing drop out (DO) supplement—Ura (SD-Ura) (Clontech) medium for 18-20 hours at 30° C. and 250 rpm. The precultures were washed prior to inoculating Minimal SD Base Gal/Raf containing DO supplement—Ura (SD Gal/Raf-Ura) (Clontech) medium to a starting optical density of 0.25. The cultures were incubated as before for 24 hours, prior to addition of 10 mM methionine to a final concentration of 1.5 mM, following which they were incubated further for 48 hours. Yeast cells from a 1 ml culture were used for extraction and gas chromatography-mass spectrometry (GC-MS) analysis as described (Kirby et al., 2008) with modifications. The cell pellet was resuspended in an equal volume of 40% potassium hydroxide and 50% ethanol prior to lysis by boiling at 95° C. for 10 minutes. An organic extraction was performed on the lysate using an equivalent volume of hexane and vortexing at high speed for 1 minute. The hexane extraction was repeated thrice before the phases were pooled and evaporated to dryness. A trimethylsilyl derivatization was performed on the dried material, and used for GC-MS analysis. The GC chromatograms showed the presence of a single peak at 27.2 minutes corresponding to 36.2 mg/L of β-amyrin in TM3 but not in TM5 (FIG. 3). The EI pattern for this peak was identical to a standard of β-amyrin (Extrasynthese) (data not shown). However, when a similar extraction and GC-MS analysis was performed on 1 ml of spent medium without yeast cells, no β-amyrin could be detected from either TM3 or TM5 (FIG. 3). In conclusion, a yeast strain was engineered that is capable of synthesizing β-amyrin in significant amounts; however, the β-amyrin that is generated is not secreted to the extracellular medium.

Example 4. Generation of Lupeol-Producing Yeast Strain TM6

Figure 4:
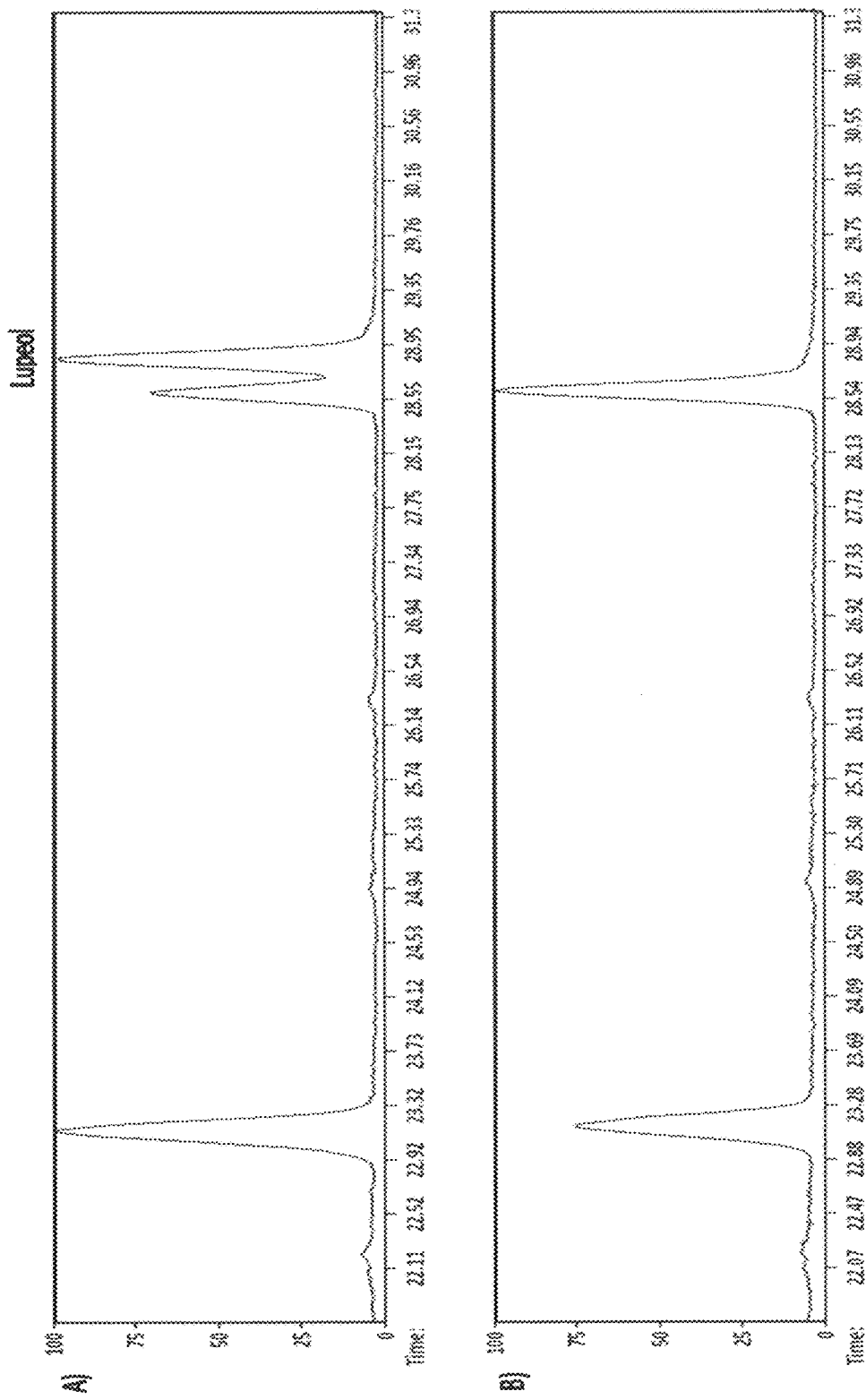
FIG. 4: GC chromatogram of: Panel A) extraction from cells of strain TM6 showing lupeol at 28.9 min, Panel B) extraction from spent medium of strain TM6, Panel C) extraction from cells of strain TM5, and Panel D) lupeol standard.
Figure 4:
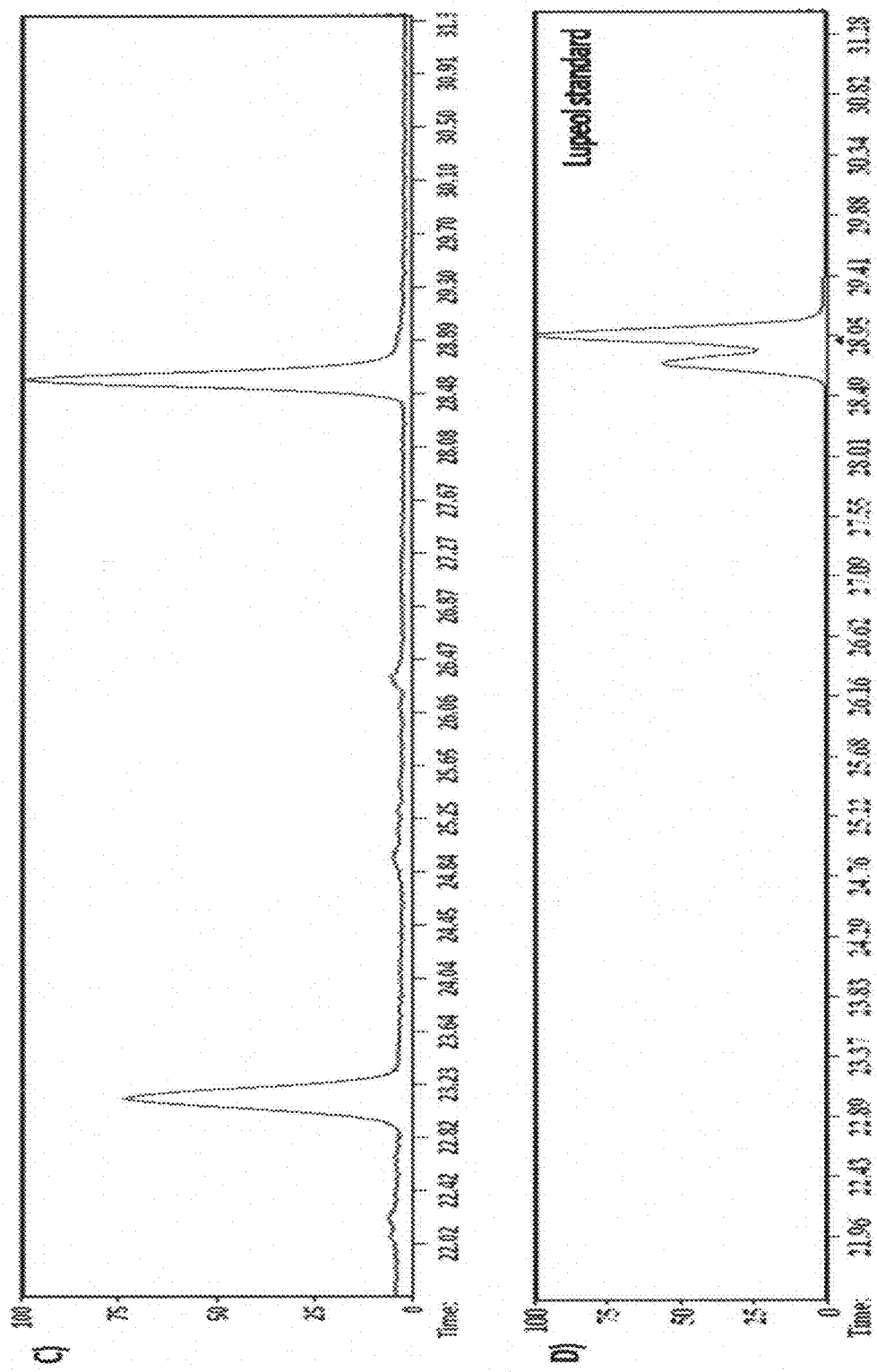

The *Arabidopsis thaliana* lupeol synthase (AtLUS1) (GenBank accession number U49919; (Herrera et al., 1998)) was cloned into the MCS 2 of plasmid pESC-URA[GAL10/tHMG1] to generate pESC-URA[GAL10/tHMG1; GAL1/AtLUS1]. The plasmid was transformed into strain TM1 to generate a lupeol-producing strain TM6. The production of lupeol by strain TM6 was verified by culturing as described in Example 3 and analyzing the trimethylsilylated fraction by GC-MS. A single peak at 28.9 minutes corresponding to 46.3 mg/L of lupeol with an EI pattern identical to a standard of lupeol (Extrasynthese) (data not shown), was observed in the GC chromatograms of TM6 but not TM5. Again, no lupeol was detected in the spent medium of strains TM6 and TM5 (FIG. 4). It can, thus, similarly be concluded that, although lupeol is synthesized by the engineered yeast strain, it is not secreted to the growth medium.

Figure 5:
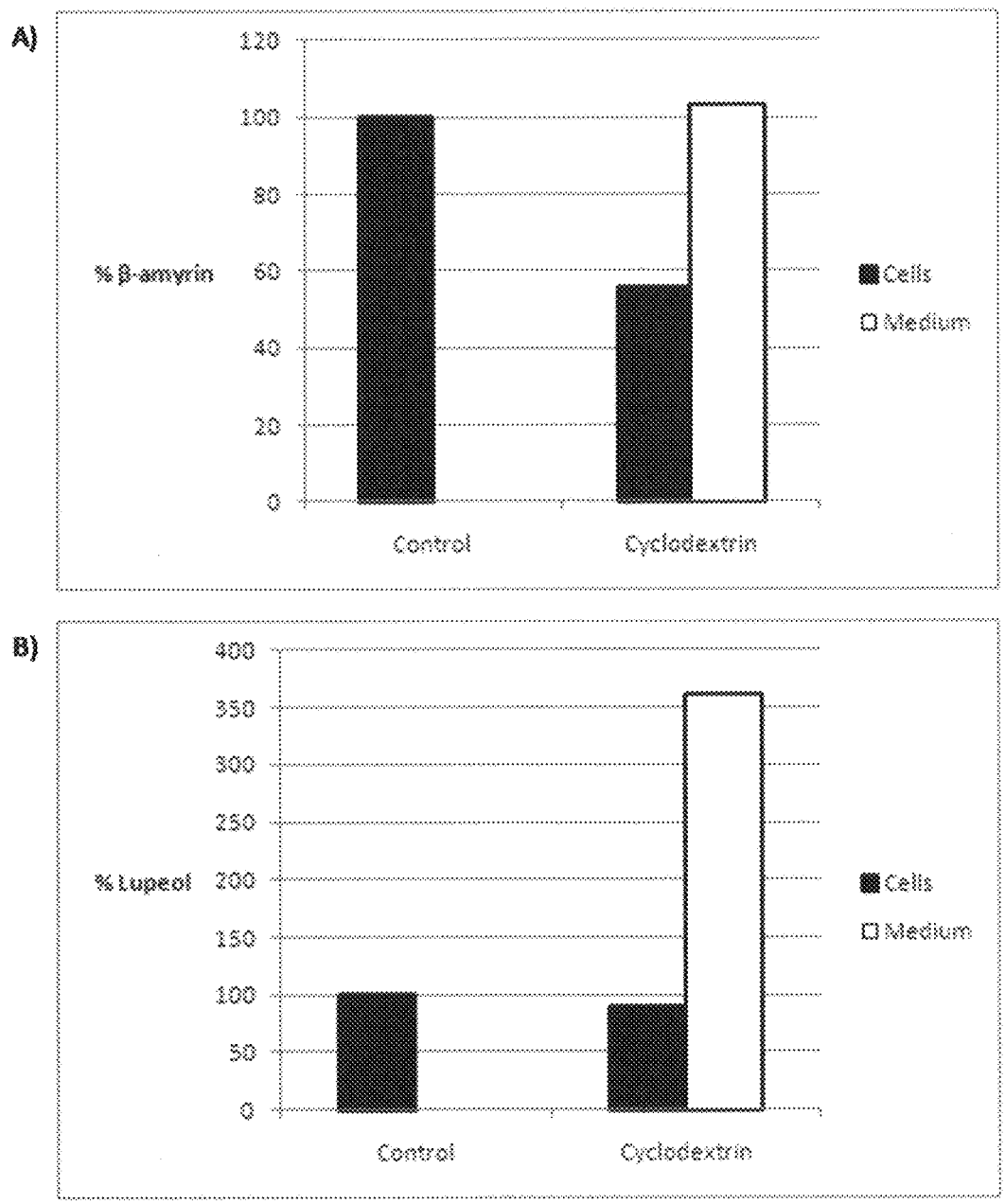
FIG. 5: Quantification of: Panel A) β-amyrin from the cells and spent medium of strain TM3, where 100% corresponds to 36.2 mg/L of β-amyrin, and Panel B) lupeol from the cells and spent medium of strain TM6, where 100% corresponds to 46.3 mg/L of lupeol. Higher concentrations of β-amyrin and lupeol were quantified from the extracts of spent medium compared to cell pellet upon cyclodextrin treatment.

Example 5. Cyclodextrin Facilitates Secretion of β-Amyrin and Lupeol into the Medium Strains TM3, TM6 and TM5 were cultured as in Example 2 with modifications. The precultures were prepared and inoculated into SD Gal/Raf-Ura medium and incubated for 24 hours as described. Along with methionine, 250 mM methyl-β-cyclodextrin (CAVASOL©, Wacker Quimica Ibérica S.A.) was also added to a final concentration of 5 mM and the cultures were incubated further under the same conditions. Post 24 hours incubation, 250 mM methyl-β-cyclodextrin was added once again to a concentration of 5 mM and the cultures were incubated further for 24 hours. The cells and spent medium were harvested from 1 ml of the culture and processed separately for extraction and GC-MS analysis as described in Example 3. GC chromatograms confirmed the presence of β-amyrin and lupeol in the cell pellet as well as in spent medium of strains TM3 and TM6, respectively, but not TM5, with higher concentrations of both β-amyrin and lupeol quantified from the extracts of spent medium (37.3 mg/L and 164.2 mg/L, respectively) when compared to cell pellet (20.4 mg/L and 41.7 mg/L, respectively) (FIG. 5). Additionally, the total concentration of both β-amyrin and lupeol is found to be 1.6-fold and 4.4-fold, respectively, higher in cultures treated with cyclodextrin when compared to non-treated controls. The absence of β-amyrin and lupeol in the extracts obtained from spent medium of cells cultured in the absence of cyclodextrin and vice versa strongly underscore the effects of cyclodextrins on the secretion of triterpene sapogenin backbones into the medium.

Figure 6:
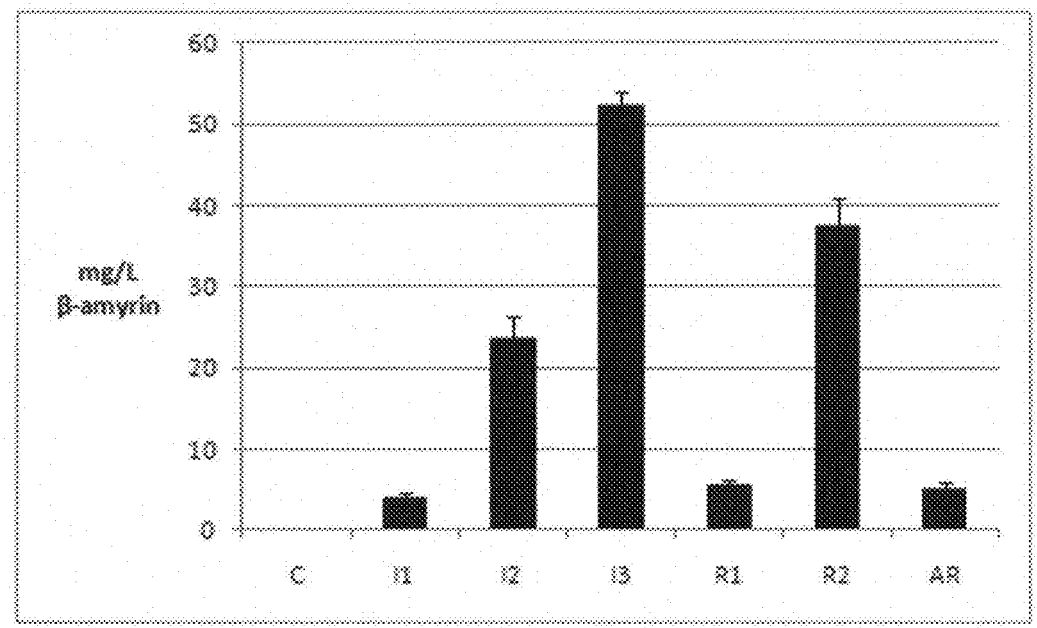
FIG. 6: Dose-dependent secretion of β-amyrin quantified for strain TM3, where cyclodextrin was added on: Day 1 (I1), Day 1 and 2 (I12), Day 1, 2 and 3 (I3), Day 2 (R1), Day 2 and 3 (R2), Day 3 (AR) and untreated control (C).

Further, it was determined whether cyclodextrin facilitates the secretion of triterpene sapogenin backbones in a dose-dependent manner. For this, the β-amyrin-producing strain TM3 was employed and applied cyclodextrin at different times during culturing. A total of seven culturing conditions were set up, which included an untreated control (C) and six treated samples, with cyclodextrin added to a concentration of 5 mM each time. To samples I1, I2 and I3, cyclodextrin was added on Day 1 immediately after inoculation into SD Gal/Raf-Ura medium. To samples I2 and I3, an additional dose of cyclodextrin was added on Day 2, together with addition of methionine. Additionally, to sample I3, a third dose of cyclodextrin was added on Day 3. Further, to samples R1, R2, and AR1, cyclodextrin was added on; Day 2 only, Day 2 and Day 3, and Day 3 only, respectively. Extractions were performed on the spent medium of all the samples on Day 4 and quantified for β-amyrin using GC-MS as described. Surprisingly, a direct correlation was observed between the amount of β-amyrin quantified from the spent medium and the number of times cyclodextrin was added to the sample, thereby suggesting the dose-dependent nature of this secretion (FIG. 6). For the purpose of the following experiments, being the generation of sapogenins derived from its precursors (e.g., β-amyrin, lupeol), it was decided to employ condition R2 for all subsequent experiments. In this way, the excessive secretion from the cells into the medium and, hence, loss of β-amyrin, which is the precursor for the consecutive cytochrome P450 monooxygenases (CYPs), is prevented.

Example 6. Secretion of Triterpene Sapogenins from Strains TM10, TM11, TM12 and TM22

To produce triterpene sapogenins in the yeast strain, β-amyrin and lupeol were modified with three characterized cytochrome P450 monooxygenases (CYPs), CYP716A12 (GenBank accession number FN995113; (Carelli et al., 2011)), CYP88D6 (GenBank accession number AB433179; (Seki et al., 2008)) and CYP93E2 (GenBank accession number DQ335790; (Li et al., 2007)). The CYPs need a CYP reductase (CPR) as a redox partner for their activity. Therefore, *A. thaliana* CPR, ATR1 (At4g24520) along with the CYPs were simultaneously cloned. Both the CYPs and CPR were PCR amplified and cloned into the entry vector pDONR221 by GATEWAY™ recombination (Invitrogen Life Technologies). Further, the CYPs were GATEWAY™ recombined into the high copy number expression vector, pAG423GAL-ccdB (Addgene plasmid 14149) containing the GAL1 promoter and HIS3 auxotrophic marker to generate the plasmids pAG423[GAL1/CYP716A12], pAG423 [GAL1/CYP88D6] and pAG423[GAL1/CYP93E2]. The CPR was GATEWAY™ recombined into the high copy number expression vector pAG425GAL-ccdB (Addgene plasmid 14153) having the GAL1 promoter and LEU2 auxotrophic marker to generate plasmid pAG425[GAL1/AtATR1].

Figure 7:
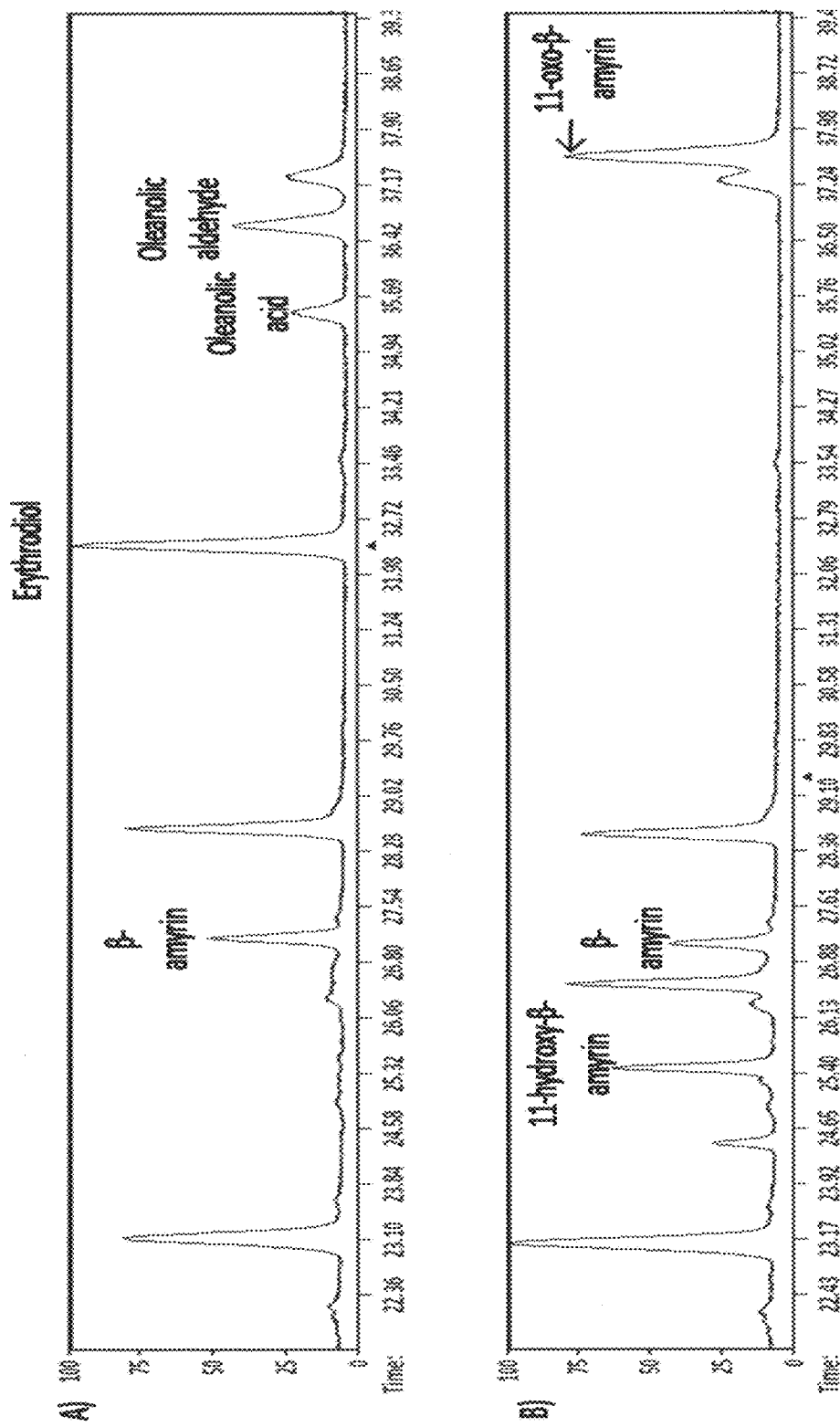
FIG. 7: GC chromatograms of extraction performed on spent medium of: Panel A) strain TM10 expressing CYP716A12, Panel B) strain TM11 expressing CYP88D6, Panel C) strain TM12 expressing CYP93E2, and Panel D) control strain TM26 expressing no CYP.
Figure 7:
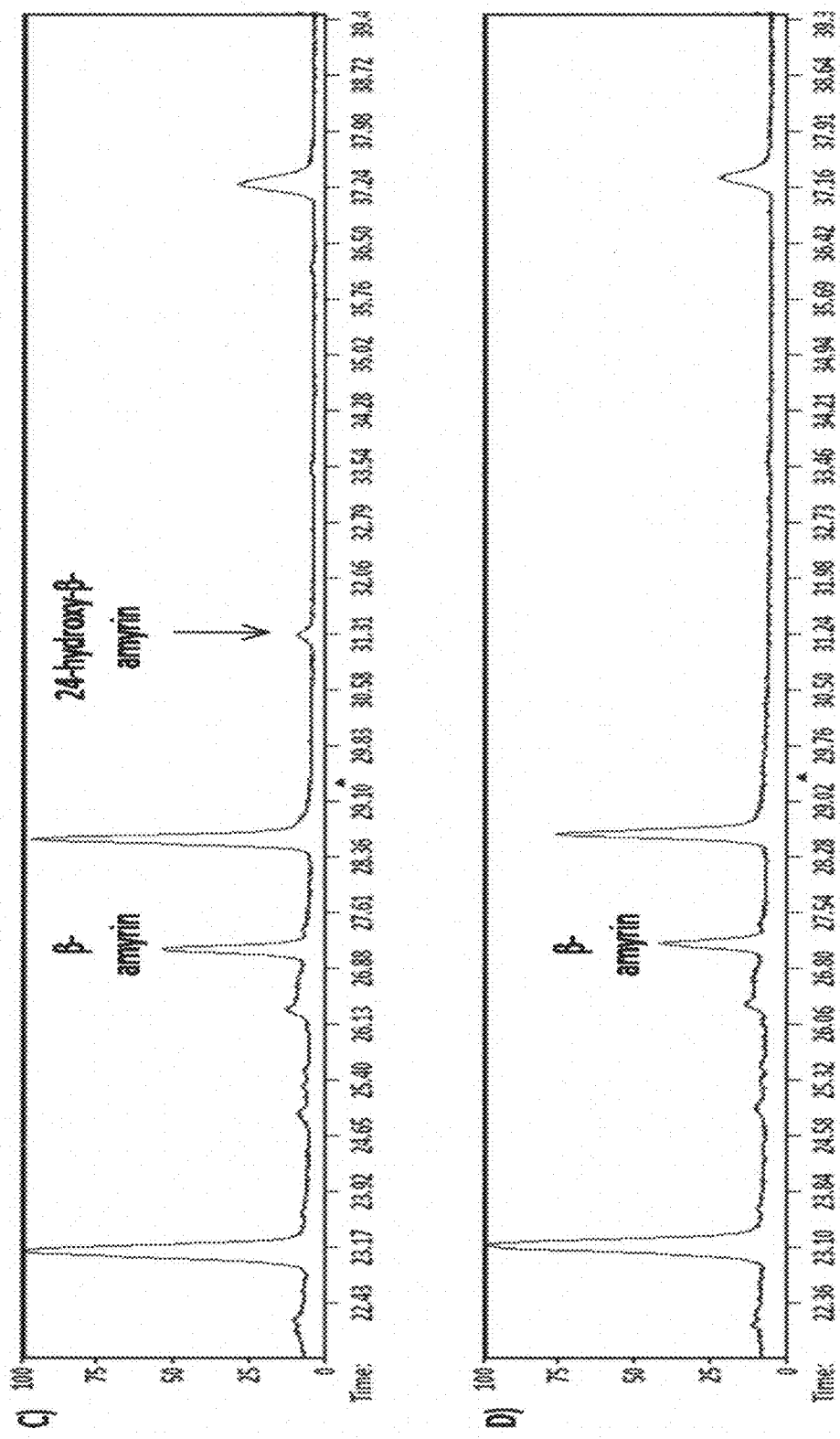

The TM3 strain was transformed with the plasmid pAG425[GAL1/AtATR1], in combination with either pAG423[GAL1/CYP716A12], pAG423[GAL1/CYP88D6], pAG423[GAL1/CYP93E2] or pAG423GAL-ccdB to generate strains TM10, TM11, TM12 and TM26, respectively. The spent medium of strains TM10, TM11, TM12 and TM26, cultured in SD Gal/Raf-Ura/-His/-Leu medium with cyclodextrin treatment as described in Example 5, was analyzed by GC-MS. Peaks corresponding to erythrodiol, oleanolic aldehyde and oleanolic acid at high concentrations were detected in the GC chromatograms of extract from TM10, indicating the C-28 hydroxylation of β-amyrin mediated by CYP716A12. Similarly, 11-hydroxy-β-amyrin and 11-oxo-β-amyrin were detected in the chromatogram of strain TM11 and 24-hydroxy-β-amyrin in the extract of strain TM12. The identity of all the hydroxylated β-amyrin peaks was confirmed by comparing their EI patterns against available standards (erythrodiol, oleanolic acid (Extrasynthese)), or previous reports when a commercial standard was unavailable. No hydroxylated β-amyrin was detected in the chromatogram of TM26 (FIG. 7). The presence of triterpene sapogenins in the growth medium of strains TM10, TM11 and TM12 suggest the role of cyclodextrin in the secretion of oleanane-type sapogenins from the yeast cells into the culture medium.

Figure 8:
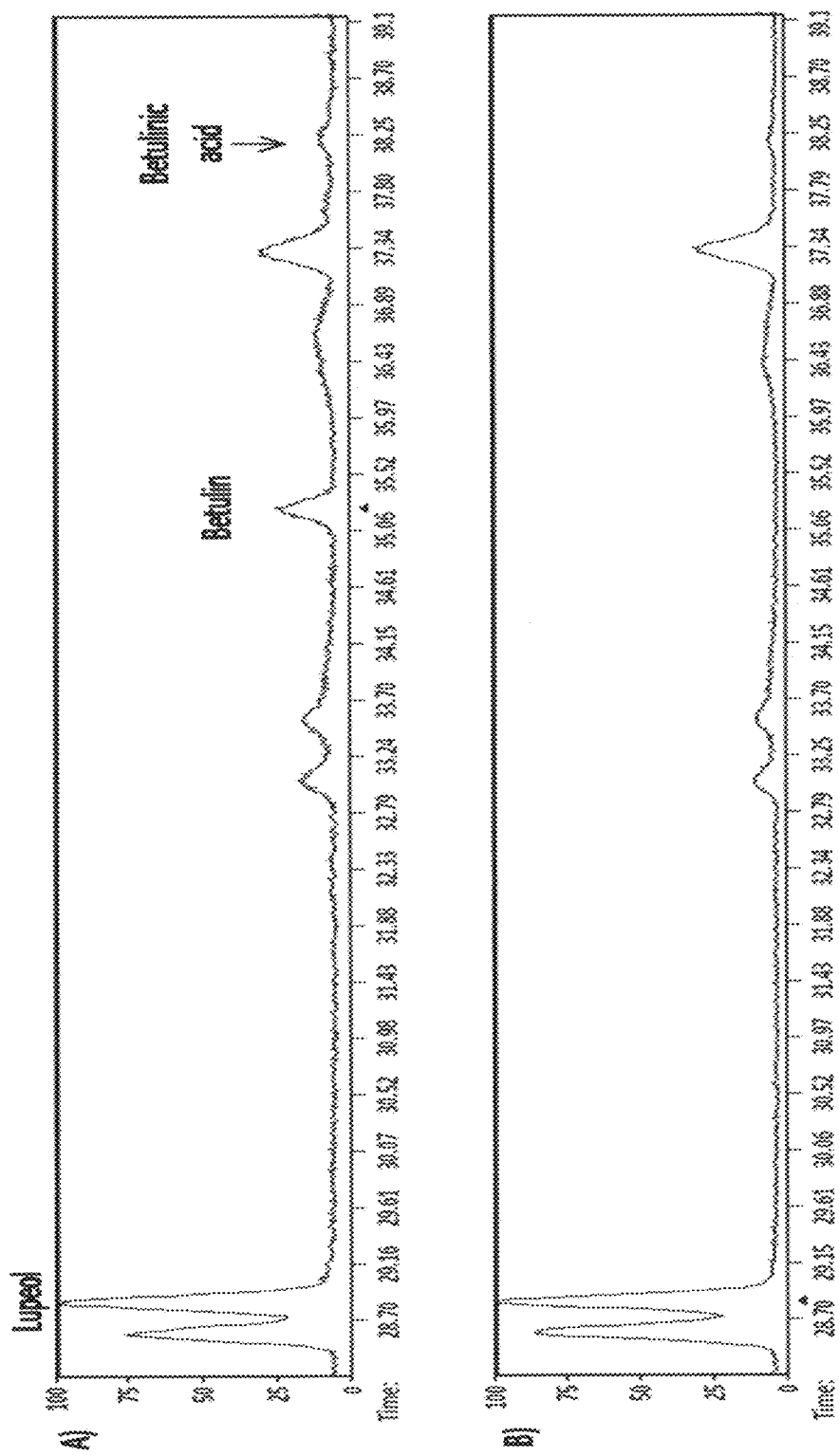
FIG. 8: GC chromatograms of extraction performed on spent medium of: Panel A) strain TM22 expressing CYP716A12, and Panel B) control strain TM28 expressing no CYP.

Next, it was determined whether cyclodextrin could also facilitate the secretion of lupane-type triterpene sapogenins from the cells to the culture medium. For this, strains TM22 and TM28 were generated by transforming strain TM6 with the plasmids pAG425[GAL1/AtATR1] and pAG423[GAL1/CYP716A12] or pAG423GAL-ccdB, respectively. Strains TM22 and TM28 were cultured as described using SD Gal/Raf-Ura/-His/-Leu medium with cyclodextrin treatment and the spent medium was used for extraction and GC-MS analysis. 7.2 mg/L betulin and 2.4 mg/L betulinic acid were detected in the chromatograms of TM22 but not TM28, indicating the C-28 hydroxylation of lupeol by CYP716A12 (FIG. 8). The detection of hydroxylated and carboxylated lupeol in the growth medium further supports the effect of cyclodextrin in the secretion of lupane-type sapogenins as well.

III. Production of Triterpenoid Sapogenins in Plant Cultures

Example 7. Cyclodextrin Facilitates Secretion of Triterpene Sapogenins from *Medicago truncatula*

Figure 9:
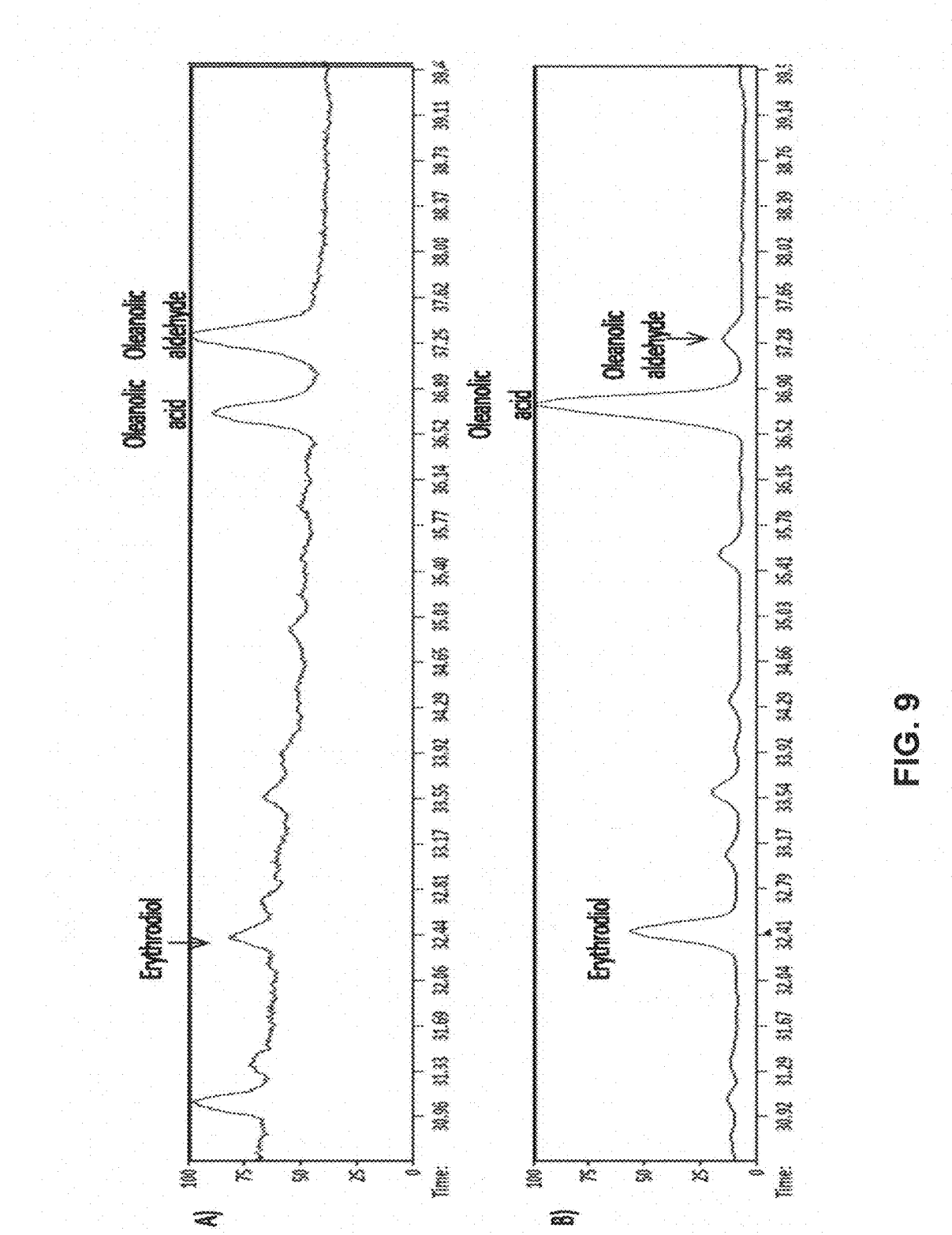
FIG. 9: GC chromatograms of extraction performed on spent medium of *M. truncatula* hairy roots treated for 48 hours with: Panel A) 25 mM cyclodextrin, Panel B) 25 mM cyclodextrin and 100 μM methyl jasmonate, Panel C) 100 μM methyl jasmonate, and Panel D) untreated control.
Figure 9:
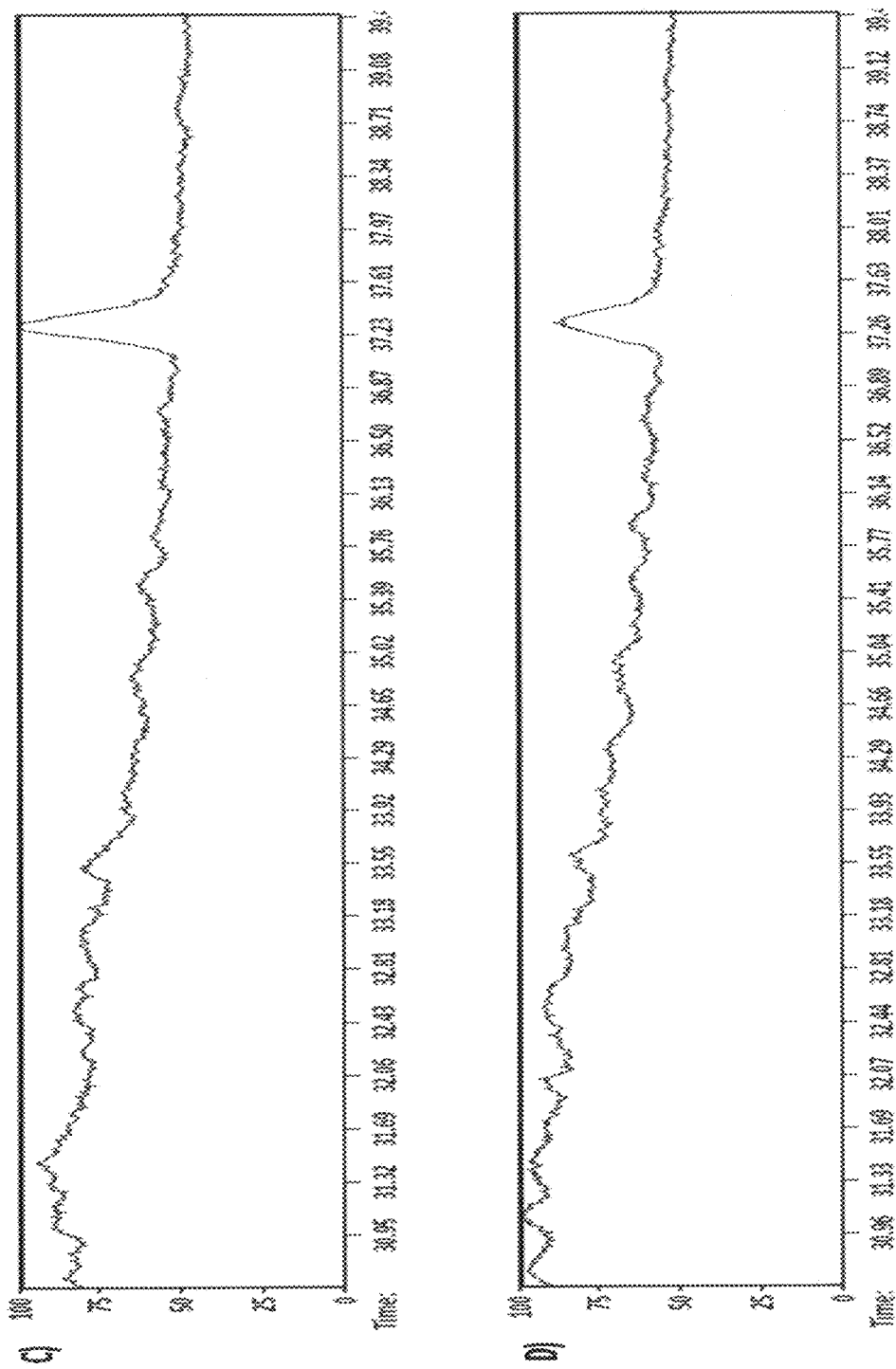

It was then determined whether cyclodextrins could also facilitate the production and/or secretion of triterpene sapogenins from the model legume *M. truncatula* by analyzing the spent medium of *M. truncatula* hairy roots transformed with pK7WG2D-GUS. The hairy roots were grown for two weeks in 20 ml Murashige and Skoog basal salt mixture including vitamins (Duchefa) prior to addition of 250 mM cyclodextrin to a final concentration of 25 mM, in combination with or without 100 µM methyl jasmonate, and compared to untreated and 100 µM methyl jasmonate only treated controls. The roots were harvested 48 hours after treatment and the spent medium was extracted and analyzed by GC-MS. Surprisingly, the triterpene sapogenins erythrodiol, oleanolic acid and oleanolic aldehyde, corresponding to the building blocks of the most abundant saponins produced by the hairy roots (Pollier et al., 2011), could now be detected in the GC chromatograms of medium of roots treated with cyclodextrin, but not in control roots (FIG. 9). EI patterns were compared against available standards to confirm the identity of erythrodiol and oleanolic acid (Extrasynthese), and previous reports for oleanolic aldehyde. Additionally, a significant increase, of up to 150-fold for erythrodiol and 2-fold for oleanolic acid, was noted when cyclodextrin was combined with methyl jasmonate treatment (FIG. 9). This confirms the role of cyclodextrins in the secretion of scarcely intracellularly accumulating saponin intermediates, the sapogenins, from plant cultures into the culturing medium, as described in Example 1.

IV. Identification and Characterization of Novel Saponin Biosynthetic Genes

Example 8. Transcript Profiling of MeJA-Treated *Bupleurum Falcatum* Reveals a Novel Plant Cytochrome P450

The genus *Bupleurum* consists of perennial herbs and forms an integral part of Asian traditional medicine in which it is used, either alone or in combination with other ingredients, for the treatment of common colds, fever and inflammatory disorders in the form of over-the-counter herbal teas.

Saikosaponins constitute the largest class of secondary metabolites in *Bupleurum* and account for ~7% of the total dry weight of roots. More than 120 closely related glycosylated oleanane- and ursane-type saikosaponins have been identified from this genus that can be distinguished only by the positions and numbers of double bonds in rings C and D and oxygenation patterns on C-16, C-23, C-28 and C-30 (FIG. 10) (Ashour and Wink, 2011). The presence of oxygenations at various positions on saikosapogenins suggests the presence of specific enzymes, generally CytP450s, capable of catalyzing these modifications on the β-amyrin and/or α-amyrin backbone in the genus *Bupleurum*. However, to date, not a single CytP450 or oxido-reductase involved in triterpene sapogenin biosynthesis has been identified from *Bupleurum* species.

To identify new saponin biosynthesis genes, a genome-wide cDNA-AFLP®-based transcript profiling was performed on the roots of hydroponically grown *B. falcatum* plants. *B. falcatum* seeds, obtained from a commercial source (on the World Wide Web at SandMountainHerbs.com), were sown in soil, and 2 weeks after germination, seedlings were transferred to aerated hydroponics medium containing 1 g/L 10-30-20 salts (Scotts, Ohio, USA), pH 6.5. Plants were grown at 16 hours/8 hours light/dark regime, at 21° C. The pH was monitored daily and adjusted to 6.5 by adding KOH to the hydroponics medium. Three weeks after the plants were transferred to the hydroponics medium, they were treated with 50 μM methyl jasmonate (MeJA) (dissolved in ethanol (EtOH)) or an equivalent amount of EtOH as a control, by adding the EtOH or MeJA solution directly to the hydroponics medium. For transcript profiling, roots were harvested 0, 0.5, 1, 2, 4, 8 and 24 hours after treatment, frozen in liquid nitrogen, and stored at −70° C. For each sample, three individual plants were pooled.

A full genome-wide cDNA-AFLP®-based transcript profiling on the roots of hydroponically grown *B. falcatum* plants was carried out as described in Vuylsteke et al. (2007). Gel images were analyzed with the AFLP-QUANTAR® PRO software (KEYGENE®, Wageningen, The Netherlands), allowing accurate quantification of band intensities. Extraction and analysis of expression data of all individual bands, selection of tags displaying differential expression, cluster analysis, sequencing, and BLAST analysis was performed as described (Rischer et al., 2006).

Using the complete set of 128 BstYI+1/MseI+2 primer combinations, the expression of a total of 18,800 transcript tags was monitored over time. In total, 1,771 MeJA-responsive transcript tags were isolated (hereafter referred to as "BF tags"). Direct sequencing of the reamplified BF tags gave good-quality sequences for 1217 (68.7%) of the fragments. To the remaining 554 tags (31.3%), no unique sequence could be attributed unambiguously, indicating that they might not represent unique gene tags, hence, these tags were not considered for further analysis. A BLAST search with the nucleotide sequences of the 1217 unique cDNA-AFLP® tags led to the annotation of 776 (63.7%) of the BF tags.

Figure 11:
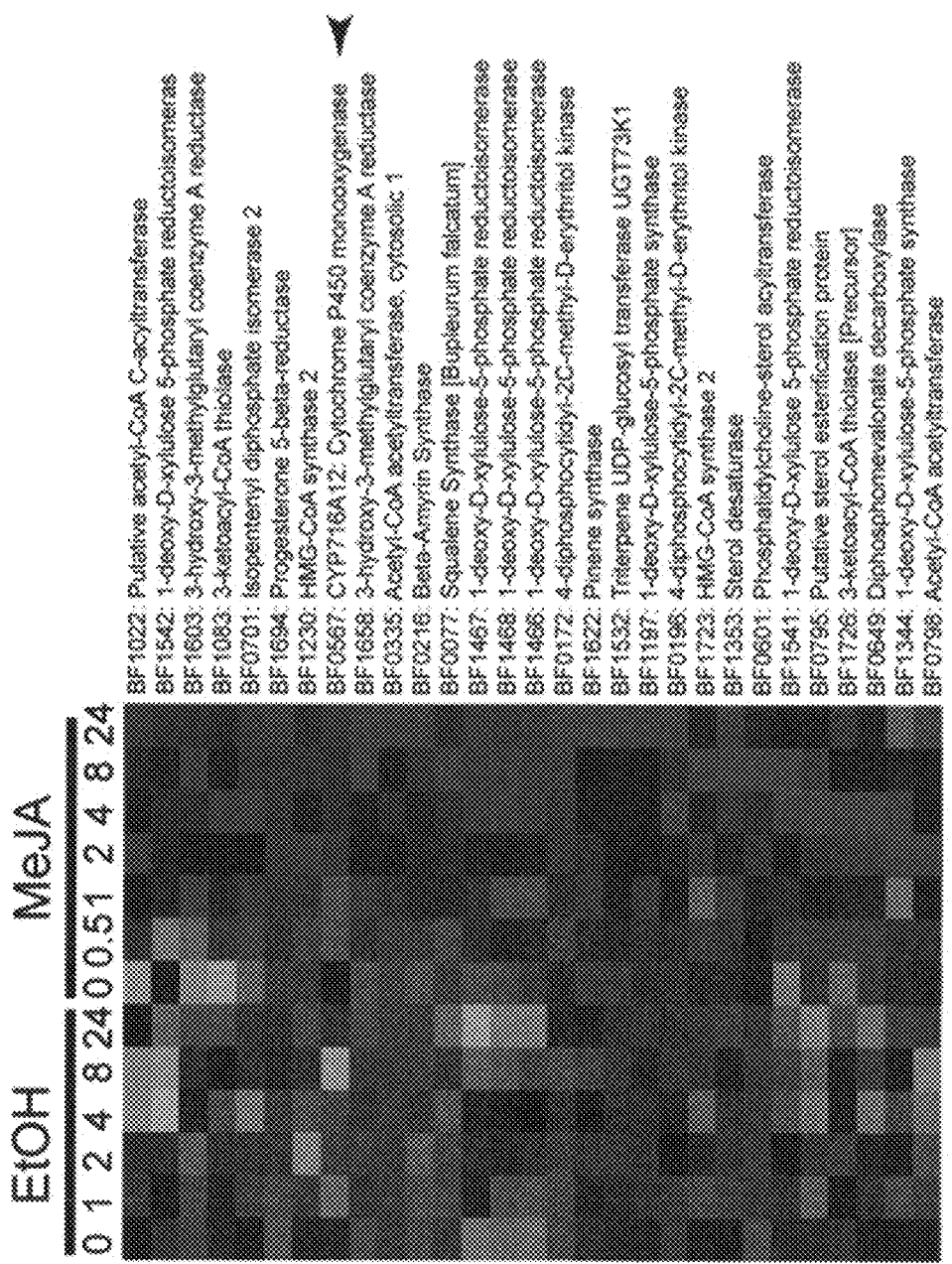
FIG. 11: Transcript profiling of jasmonate elicited *B. falcatum* roots. Subcluster of the *B. falcatum* transcriptome, comprising tags corresponding to genes reported to be involved in triterpene biosynthesis, or with high sequence similarity to such genes. Treatments and time points (in hours) are indicated on top. Blue and yellow boxes reflect transcriptional activation and repression relative to the average expression level, respectively. Gray boxes correspond to missing time points. The arrowhead indicates the CytP450 functionally defined in this study.

Average linkage hierarchical clustering analysis of the expression profiles of the 776 annotated BF tags showed that, upon MeJA treatment, the selected genes are either transcriptionally activated or transcriptionally repressed. The activated gene tags can be divided into different subclusters, based on the timing of the MeJA response. In one subcluster, genes are activated within 2 hours after the MeJA treatment, and their expression remains high thereafter. In this group, tags corresponding to genes encoding enzymes that catalyze early steps in the triterpene saponin biosynthesis, including squalene synthase (SQS) and β-amyrin synthase (bAS), can be found. These tags displayed an almost identical expression pattern, suggesting a tight co-regulation, and reached maximum levels of expression 8-24 hours post-elicitation (FIG. 11). The gene tag BF567 (hereafter named CYP716AO21) is tightly co-regulated with these genes (FIG. 11), and shows homology to the *M. truncatula* gene encoding the cytochrome P450 enzyme CYP716A12 that was recently shown to oxidize β-amyrin in a sequential three-step oxidation on C-28 to yield oleanolic acid through erythrodiol (Carelli et al., 2011; Fukushima et al., 2011). The full-length open reading frame (BF567, hereafter named CYP716AO21) corresponding to the gene tag CYP716AO21 was picked up from a *B. falcatum* Uncut Nanoquantity cDNA library (Pollier et al., 2011b). Using the primers (sense, 5'-CCTCCTTATACATTCGTTCCATTC-3' (SEQ ID NO:20) and antisense, 5'-TTAGGGTC-TACTTTCTCCCATTTG-3' (SEQ ID NO:21), the full-length coding sequence of CYP716AO21 (SEQ ID NO:1) corresponding to the gene tag CYP716AO21 was picked up from the screening of a *B. falcatum* Uncut Nanoquantity cDNA library (custom-made by Invitrogen, Carlsbad, Calif., USA) as reported (Pollier et al., 2011b). The full-length open reading frame (FL-ORF) of CYP716AO21 was PCR amplified for GATEWAY™ cloning into the entry vector pDONR221 using the primer pair P19 (GGGGA-CAAGTTTGTACAAAAAAGCAGGCTTAATGGAACTT-TCTATCACT (SEQ ID NO:5))+P20 (GGGGACCACTTT-GTACAAGAAAGCTGGGTATTAAGATGGAGATTT-GTG (SEQ ID NO:6)). The entry clone of CYP716AO21 was recombined into the high copy number expression vector pAG423GAL-ccdB (Addgene plasmid 14149) with the GAL1 promoter and HIS3 auxotrophic marker, resulting in pAG423[GAL1/CYP716AO21].

Example 9. In Vivo Activity of CYP716AO21 in Yeast Strain TM7

Figure 12:
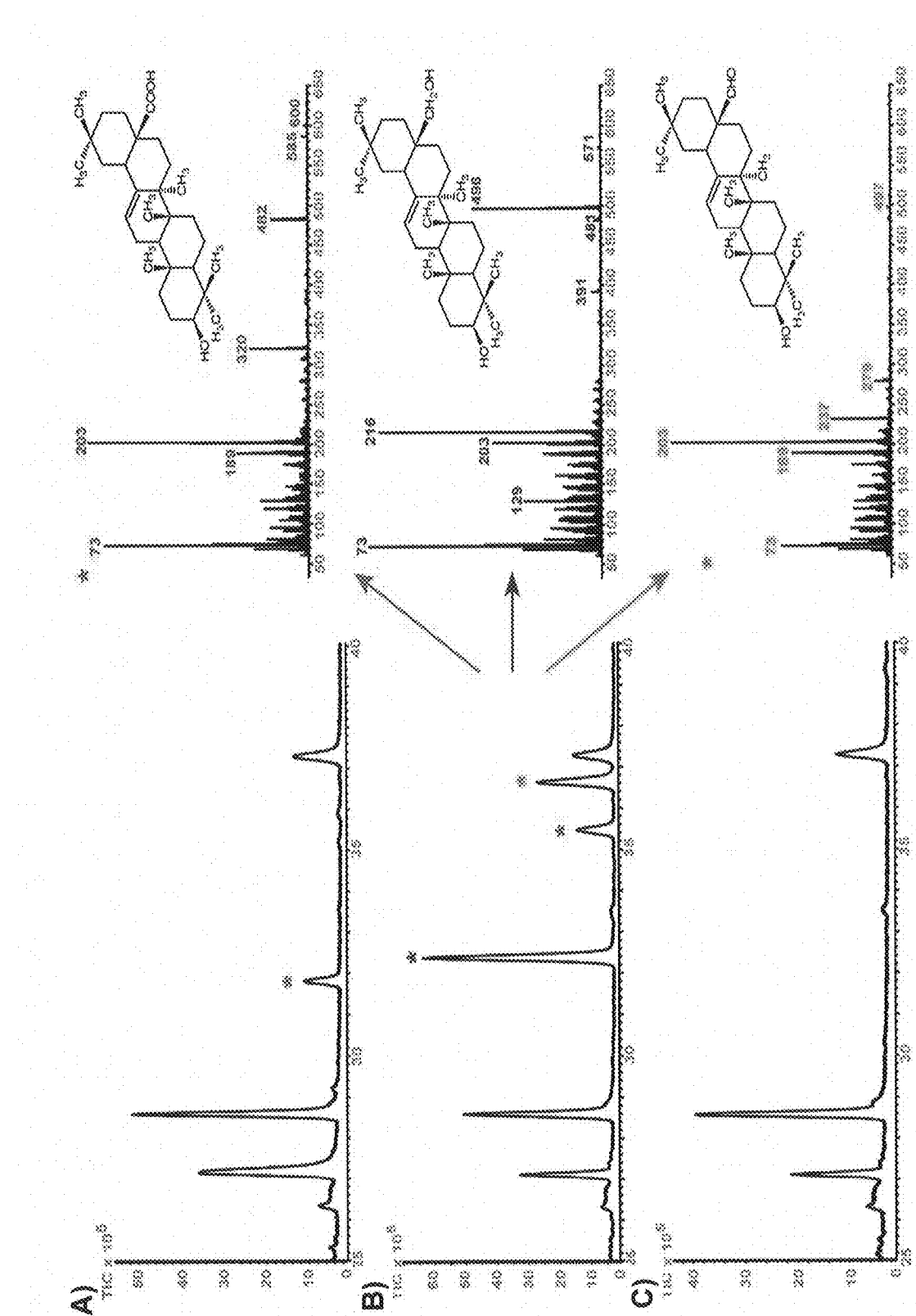
FIG. 12: GC chromatograms corresponding to: Panel A) Extraction from cells of strain TM7. Panel B) Extraction from cells of strain TM10. Enclosed box figure shows the mass spectra extracted from the indicated (*) peak. Panel C) Extraction from cells of control strain TM26. Panel D) Mass spectra extracted from the peak indicated (*) at 31.8 minutes of strain TM7. Panel E) Mass spectra of an erythrodiol standard.
Figure 12:
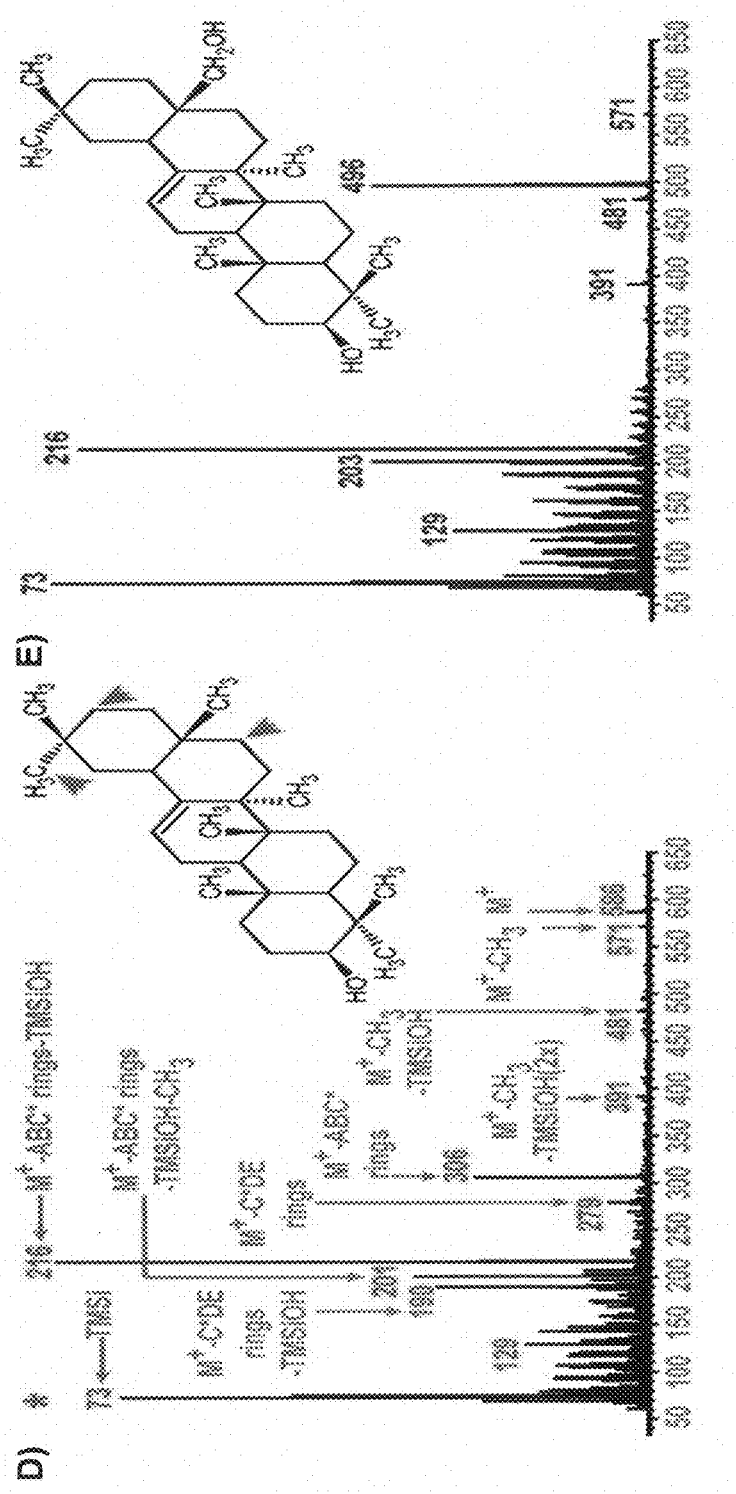

Yeast strain TM7 was generated by super-transforming strain TM3 (see Example 3) with plasmids pAG423[GAL1/CYP716AO21] and pAG425[GAL1/AtATR1], expressing CYP716AO21 and the *A. thaliana* CytP450 reductase (CPR), AtATR1 (At4g24520), respectively, from the galactose inducible GAL1 promoter. In parallel, a control strain TM26 harboring only pAG425[GAL1/AtATR1] in TM3 was also generated. Cell pellets analyzed by GC-MS showed the presence of a unique new peak eluting at 31.8 minutes in TM7 (FIG. 12, Panel A), but not TM26 (FIG. 12, Panel C). The EI pattern of this peak corresponded to a hydroxylated derivative of β-amyrin, with the alcohol function on either the D or E ring of β-amyrin (FIG. 12, Panel D).

Since CYP716AO21 was tentatively annotated as a homolog of the *M. truncatula* CYP716A12 (GenBank accession number FN995113; (Carelli et al., 2011)), the GC elution time was compared to the EI pattern of the new peak in TM7 with a standard of erythrodiol (28-hydroxy-β-amyrin). The strain TM10 was generated by transforming plasmid pAG423[GAL1/CYP716A12] along with pAG425 [GAL1/AtATR1] in TM3, and compared its GC-MS profile with TM7, TM26 and an erythrodiol standard. A peak corresponding to the elution time and EI of standard erythrodiol (FIG. 12, Panel E) was observed at 32.5 minutes in the GC chromatogram of TM10 (FIG. 12, Panel B) but not TM7 and TM26, indicating that CYP716AO21 hydroxylates β-amyrin at a position different than CYP716A12. Therefore, the oleanane-type triterpenoid sapogenins found in *Bupleurum* (Ashour and Wink, 2011) were looked at in order to narrow down the possible hydroxylation positions of CYP716AO21 on rings D and E of β-amyrin to C-16, C-21 and C-29 (FIG. 10), which are positions for which a CytP450 has not been characterized to date.

Example 10. Effect of CPR:CytP450 Ratio on In Vivo Activity of CYP716AO21

The endoplasmic reticulum (ER) localized CPRs are flavoproteins, containing both a redox cofactor flavin adenine dinucleotide (FAD) and flavin mononucleotide (FMN), that serve as electron donor proteins for several ER oxygenases, including CytP450s. Therefore, optimal interaction between CPR and CytP450 is essential to allow the reducing equivalents from NADPH to pass from the CPR to the CytP450 (Reed and Backes, 2012). In an attempt to increase the efficiency of hydroxylation of β-amyrin by CYP716AO21, the effect of the ratio of CPR to CytP450 was determined by varying the expression level of AtATR1 while keeping the expression of CYP716AO21 constant.

Figure 13:
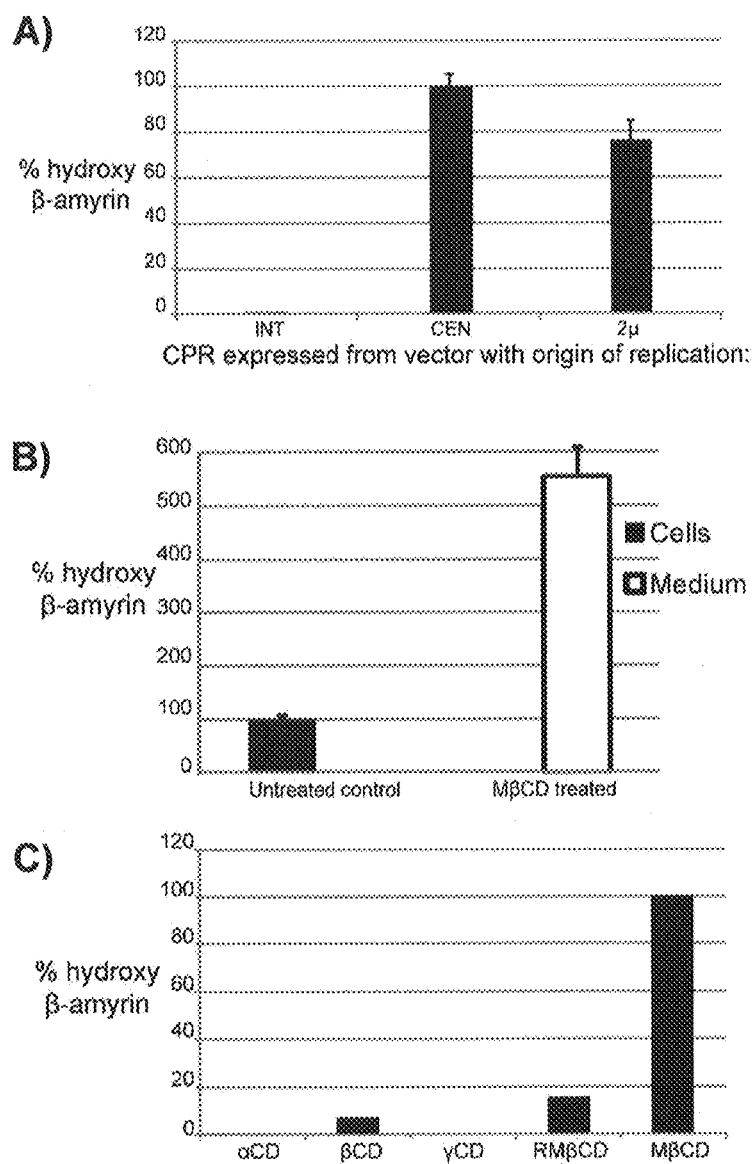
FIG. 13: Panel A) Effect of CPR:CytP450 ratio on the in vivo activity of CYP716AO21 in strains TM8, TM9 and TM7. Panel B) Relative amounts of hydroxylated β-amyrin quantified from the cells and spent medium of strain TM9. Panel C) Relative amounts of hydroxylated β-amyrin quantified from spent medium of strain TM9 treated with different variants of CD.

The CPR:CytP450 ratios between 1:5 and 1:30 have been reported to be ideal for the efficient functioning of yeast and mammalian CytP450s (Reed and Backes, 2012). Therefore, the AtATR1 was expressed from either an integrated (pAG305, 1 copy per cell), low-copy number (pAG415, 3-5 copies per cell), or high-copy number (pAG425, 10-40 copies per cell) vector, in combination with CYP716AO21 always expressed from the high-copy number plasmid (pAG423, 10-40 copies per cell). Thus, two strains were generated, TM8 and TM9, overexpressing pAG423[GAL1/CYP716AO21] along with pAG305[GAL1/AtATR1] or pAG415[GAL1/AtATR1], respectively, and compared the amount of hydroxylated β-amyrin produced by these strains with that of TM7. In accordance with this assumption, strain TM9 accumulated higher levels of hydroxylated β-amyrin compared to TM8 and TM7, with the lowest accumulation in the strain expressing the integrated copy of CPR (FIG. 13, Panel A). Therefore, AtATR1 was expressed from the low-copy number vector pAG415 for further experiments.

Example 11. Secretion of Triterpene Sapogenins from Strains TM9

For the following experiments with strain TM9, condition R2 was employed to avoid the excessive secretion and, hence, loss of β-amyrin, the precursor for CYP716AO21, from the cells into the medium. Surprisingly, the hydroxylated β-amyrin eluting at 31.8 minutes was only observed in the GC chromatograms of the spent medium and not cell pellets of TM9 upon MβCD treatment (FIG. 13, Panel B), suggesting the complete secretion of the hydroxylated product from the yeast cells into the medium.

The specificity of the type of CD used was also determined on the sequestering of hydroxylated β-amyrin from the cells into the spent medium of strain TM9. The most abundant variants of CD are α, β and γCD, which have 6, 7 and 8 glucose units, respectively. Therefore, αCD, βCD, γCD, Random MβCD (RMβCD) or MβCD were applied to a final concentration of 5 mM as in condition R2 and analyzed the spent medium on Day 4, for quantification of the amount of hydroxylated β-amyrin secreted into the medium. Sequestration was only observed with the βCD and its methylated versions and the highest amount of hydroxylated β-amyrin was detected upon RMβCD and MβCD treatment, suggesting a strong specificity of the methylated forms of CD over the unmethylated forms, for sequestering of triterpenoid sapogenins from yeast cells (FIG. 13, Panel C).

Example 12. Transcript Profiling of MeJA-Treated *Maesa Lanceolata* Reveals a Novel Plant Cytochrome P450

*Maesa lanceolata*, a member of the Myrsinaceae family, is a shrub or small tree indigenous to Africa. African traditional healers use extracts and/or parts of the plant for the treatment of a wide range of diseases including infectious hepatitis, bacillary dysentery, impetigo, ozena, dermatoses and neuropathies. Methanol extracts of *M. lanceolata* leaves are rich in maesasaponins and have been shown to possess virucidal, molluscicidal, fungistatic and antimutagenic activities (Sindambiwe et al., 1998). The maesasaponins identified so far are derived from an oleanane skeleton via modifications of the β-amyrin backbone, resulting in a characteristic C-13,28 hemiacetal or ester bridge and oxidations on C-16, C-21 and C-22 (FIG. 14) (Foubert et al., 2010; Manguro et al., 2011). The hemiacetal or ester bridge between C-13 and C-28 is thought to occur through the reaction between a C-13 hydroxyl and C-28 aldehyde or carboxyl group, respectively (Vincken et al., 2007). The presence of these diverse oleanane maesasaponins suggests the presence of a β-amyrin-specific OSC (or β-amyrin synthase) along with specific CytP450s-catalyzing oxygenations at C-16, C-21, C-22 and C-28 in *M. lanceolata*. However, to date, not a single triterpene saponin biosynthetic gene has been identified from *Maesa*.

To identify new saponin biosynthetic genes, a transcript profiling was performed on methyl jasmonate (MeJA) treated *M. lanceolata* axenic shoot cultures. *M. lanceolata* axenic shoot cultures were generated and maintained as described (Faizal et al., 2011). For elicitation, each pot of shoot culture was sprayed with 2 ml deionized water containing 0.05% (v/v) TWEEN®-20 in combination with 500 µM MeJA (10 µl of 100 mM stock dissolved in ethanol) or an equivalent amount of ethanol as control. For transcript profiling, samples were collected 0, 0.5, 1, 2, 4, 8, 24 and 48 hours after elicitor or mock treatments. For each sample, three different plants were pooled.

Figure 15:
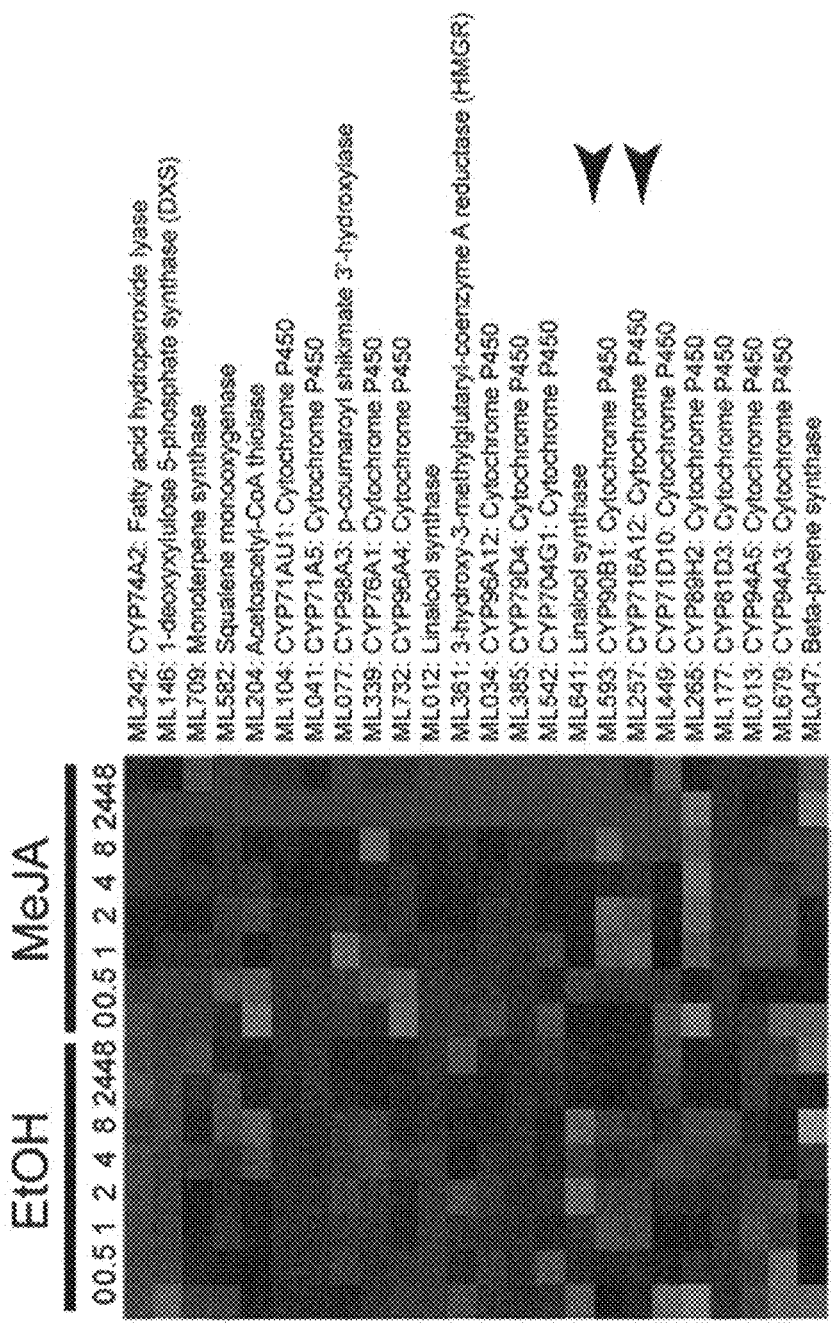
FIG. 15: Transcript profiling of jasmonate elicited *M. lanceolata* plants. Subcluster of the *M. lanceolata* transcriptome, comprising all tags corresponding to genes reported to be involved in terpene biosynthesis, or with high sequence similarity to such genes, and all gene tags corresponding to CytP450s. Treatments and time points (in hours) are indicated on top. Blue and yellow boxes reflect transcriptional activation and repression relative to the average expression level, respectively. Gray boxes correspond to missing time points.

Using the complete set of 128 BstYI+1/MseI+2 primer combinations, a genome-wide cDNA-AFLP® transcript profiling analysis (Vuylsteke et al., 2007; see also Example 8) was carried out to monitor the expression of a total of 13,558 transcript tags over time. In total, 733 MeJA-responsive transcript tags were isolated (hereafter referred to as "ML tags"). Direct sequencing of the reamplified ML tags gave good quality sequences for 545 (74.4%) of the fragments. To the remaining 188 tags (25.6%), no unique sequence could be attributed unambiguously, indicating that they might not represent unique gene tags and, hence, these were not considered for further analysis. A BLAST search with the nucleotide sequences of the 545 unique cDNA-AFLP® tags led to the annotation of 312 (57.2%) of the ML tags. Average linkage hierarchical clustering analysis of the expression profiles of the ML tags showed that, upon MeJA treatment, the genes are either transcriptionally activated or transcriptionally repressed. The activated gene tags can be divided into different subclusters, based on their MeJA response time. In one subcluster, a gene tag that reached maximum levels of expression 24-48 hours post-elicitation and corresponding to squalene epoxidase (SQE) can be found (FIG. 15). The gene tags ML257 and ML593, corresponding to CytP450s, are tightly co-regulated with this gene (FIG. 15). The gene tag ML257 shows homology to the *M. truncatula* CYP716A12 that was shown to oxidize 3-amyrin in a sequential three-step oxidation on C-28 to yield oleanolic acid through erythrodiol (Carelli et al., 2011; Fukushima et al., 2011), and the gene tag ML593 shows homology to the *A. thaliana* steroid 22α-hydroxylase gene encoding a CytP450 enzyme that catalyzes the oxidation of sterols on the C-22 position (Fujita et al., 2006). The full-length open reading frame ML593 corresponding to the respective gene tag was picked up from a *M. lanceolata* Uncut Nanoquantity cDNA library (Pollier et al., 2011), using the primer pairs P27 (CTCTTGCATTCAATC-CGAAAC (SEQ ID NO:10))+P28 (AGCAAAGAATGCCT-TGGCTA (SEQ ID NO:11)). The FL-ORF of ML593 was PCR amplified for GATEWAY™ cloning in pDONR221 using the primer pairs P39 (GGGGACAAGTTTGTA-CAAAAAAGCAGGCTTAATGTGGGTAGTGGGATTA (SEQ ID NO:12))+P40 (GGGGACCACTTTGTA-CAAGAAAGCTGGGTATCACTTGTTTTTCTTGGT (SEQ ID NO:13)). The entry clone ML593 was GATE-WAY™ recombined into the high-copy number expression vector pAG423GAL-ccdB behind the galactose inducible GAL1 promoter and having the HIS3 auxotrophic marker, resulting in pAG423[GAL1/ML593].

Example 13. In Vivo Activity of ML593 in Yeast Strain TM21

Figure 16:
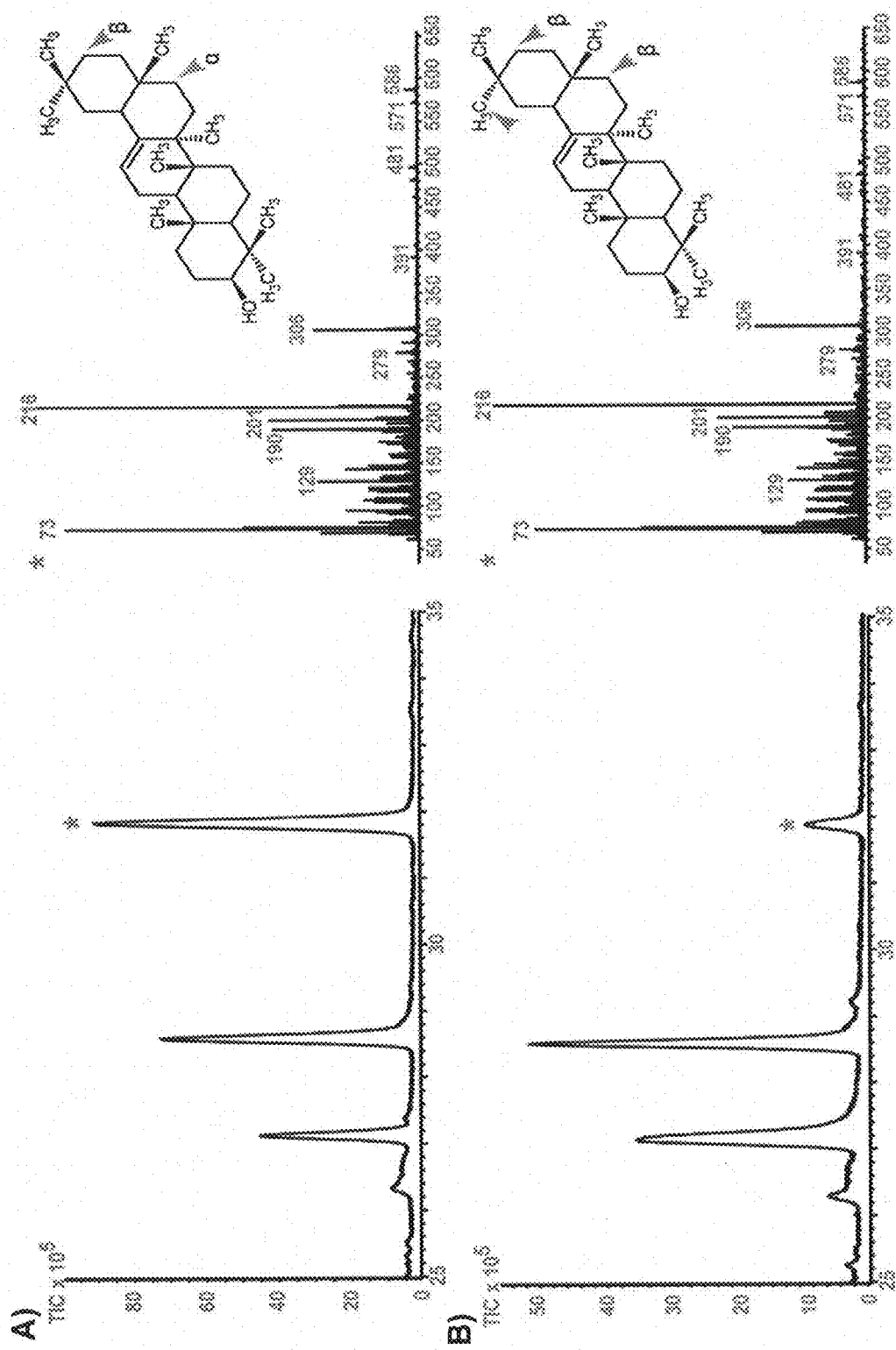
FIG. 16: GC chromatograms corresponding to: Panel A) Extraction from spent medium of strain TM21. Arrowheads indicate the positions that could be hydroxylated by ML593 and are common with predicted positions of CYP716AO21. Panel B) Extraction from spent medium of strain TM9. Panel C) Extraction from spent medium of control strain TM27. Right panel shows mass spectra extracted from the indicated (*) peaks.
Figure 16:
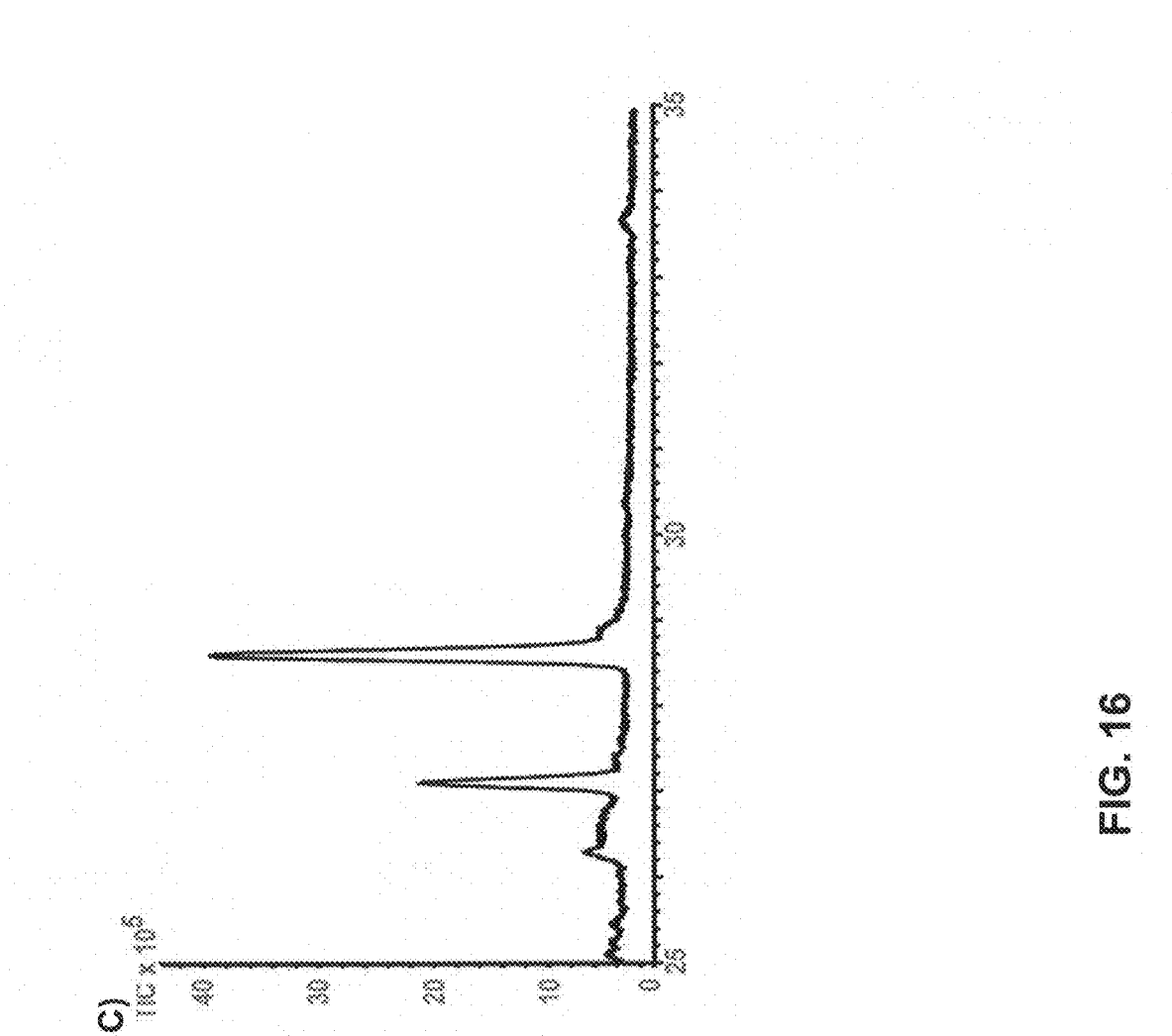

To characterize the putative CytP450, ML593 from our transcript profiling, strain TM21 was generated from the β-amyrin-producing strain TM3 (Table 4; see Example 3), by supertransforming with the plasmids pAG415[GAL1/AtATR1] and pAG423[GAL1/ML593]. The strains TM21 and TM27 (Table 4) were cultured in the presence of MβCD and the spent medium analyzed by GC-MS. A new peak eluting at 31.8 minutes corresponding to a hydroxylated β-amyrin in strain TM21 was observed (FIG. 16, Panel A), but not in the control strain TM27 (FIG. 16, Panel C). The EI pattern of this peak (FIG. 16, Panel A) corresponded to a hydroxylation on the D or E ring of the oleanane structure and was similar to that observed with strain TM9 (Table 4) expressing CYP716AO21 (FIG. 16, Panel B). The strong similarity between the elution time and EI pattern of the hydroxylated β-amyrin in strain TM21 and TM9 further supports this assumption. It was also observed that strain TM21 produced eight-fold more hydroxy β-amyrin than strain TM9, highlighting the better efficiency of ML593 for hydroxylating β-amyrin as compared to CYP716AO21.

V. Combinatorial Biosynthesis of Triterpenoid Sapogenins in Yeast

Example 14. Combinatorial Biosynthesis Using CYP716AO21 and CYP716A12

Combinatorial biosynthesis, also known as combinatorial biochemistry, involves the combination of genes from different organisms in a heterologous host to produce bioactive compounds by establishing novel enzyme-substrate combinations in vivo, which, in turn, could lead to the biosynthesis of novel natural products (Pollier et al., 2011). Although CYP716AO21 is tentatively annotated as a homolog of CYP716A12, the GC elution time and E1 pattern of the β-amyrin hydroxylation product of CYP716AO21 is different from erythrodiol (FIG. 12). It was reasoned that if the two enzymes hydroxylate β-amyrin at two different carbon positions, it should be possible to combine the enzymes in the yeast strain TM3 and produce a combinatorial compound not produced by either of the enzymes alone. Therefore, strain TM30 was generated from TM3 by overexpressing the plasmids pAG415[GAL1/AtATR1] and pAG423[GAL1/CYP716AO21-T2A-CYP716A12], where CYP716AO21 and CYP716A12 are stitched together into a self-processing polyprotein via the 2A oligopeptide (de Felipe et al., 2006), which is expressed from a single galactose inducible GAL1 promoter. The self-processing polyprotein of CYP716AO21 and CYP716A12 was generated by amplifying the FL-ORF of CYP716AO21 without a stop codon and having a 3'-overhang of the partial T2A sequence using the primer pair P19

(GGGGACAAGTTTGTACAAAAAAGCAGGCTTAATGG
AACTTTCTATCACT (SEQ ID NO: 5)) +

P23 (ACCGCAUGTTAGCAGACTTCCTCTGCCCTCA
GATGGAGATTTGTGGGGAT (SEQ ID NO: 8)).

The FL-ORF of CYP716A12 was amplified with a 5'-overhang of the partial T2A sequence using the primers P24

(ATGCGGUGACGTCGAGGAGAATCCTGGCCCAATGGAG
CCTAATTTCTATC (SEQ ID NO: 9)) +

P22 (GGGGACCACTTTGTACAAGAAAGCTGGGTATTA
AGCTTTGTGTGGATAAAGGCG (SEQ ID NO: 7))

such that there was an overlap of 7 bp between the two amplified sequences. Since the primers P23 and P24 contain an Uracil each, the CYP716AO21 and CYP716A12 were PCR amplified using the Pfu Turbo Cx polymerase (Stratagene). The purified gel fragments were used for Uracil-Specific Excision or USER™ Cloning (New England Biolabs) to generate two fragments with complementary sticky ends that were ligated in vitro using the T4 DNA ligase (Invitrogen). The ligated DNA product was once again gel purified and used as template for amplification with the primers P19+P22. This amplicon was GATEWAY™ recombined into pDONR221, sequence verified and further recombined into pAG423GAL-ccdB to generate pAG423[GAL1/CYP716AO21-T2A-CYP716A 12].

Figure 17:
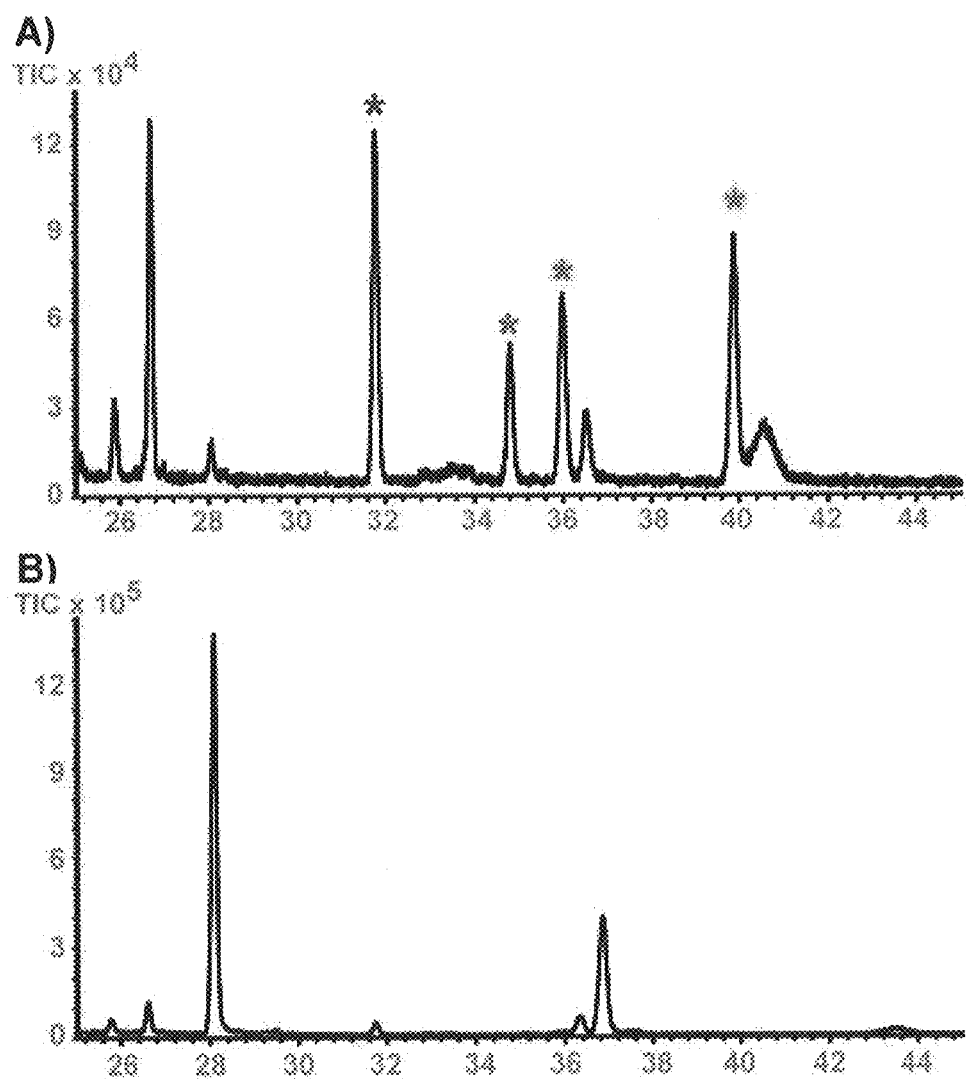
FIG. 17: GC chromatograms corresponding to: Panel A) Extraction from spent medium of strain TM30. Panel B) Extraction from spent medium of strain TM9. Panel C) Extraction from spent medium of strain TM17. Panel D) An echinocystic acid standard. Panel E) Mass spectra extracted from the peak indicated (*) at 40.5 minutes of strain TM30. Parts of the structure in blue depict the possible unknown hydroxylation position. Panel F) Mass spectra extracted from echinocystic acid standard. Panel G) Oxidation of β-amyrin by CYP716AO21 and CYP716A12.
Figure 17:
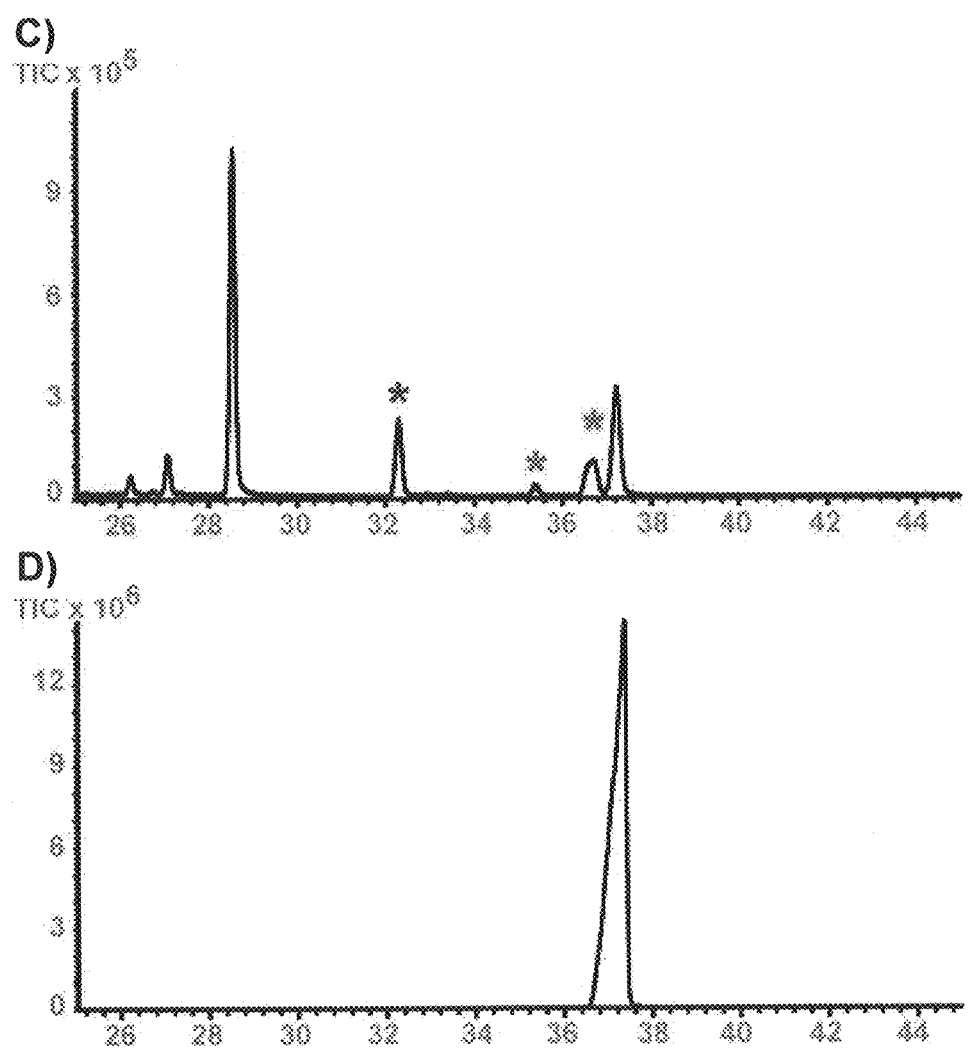
Figure 17:
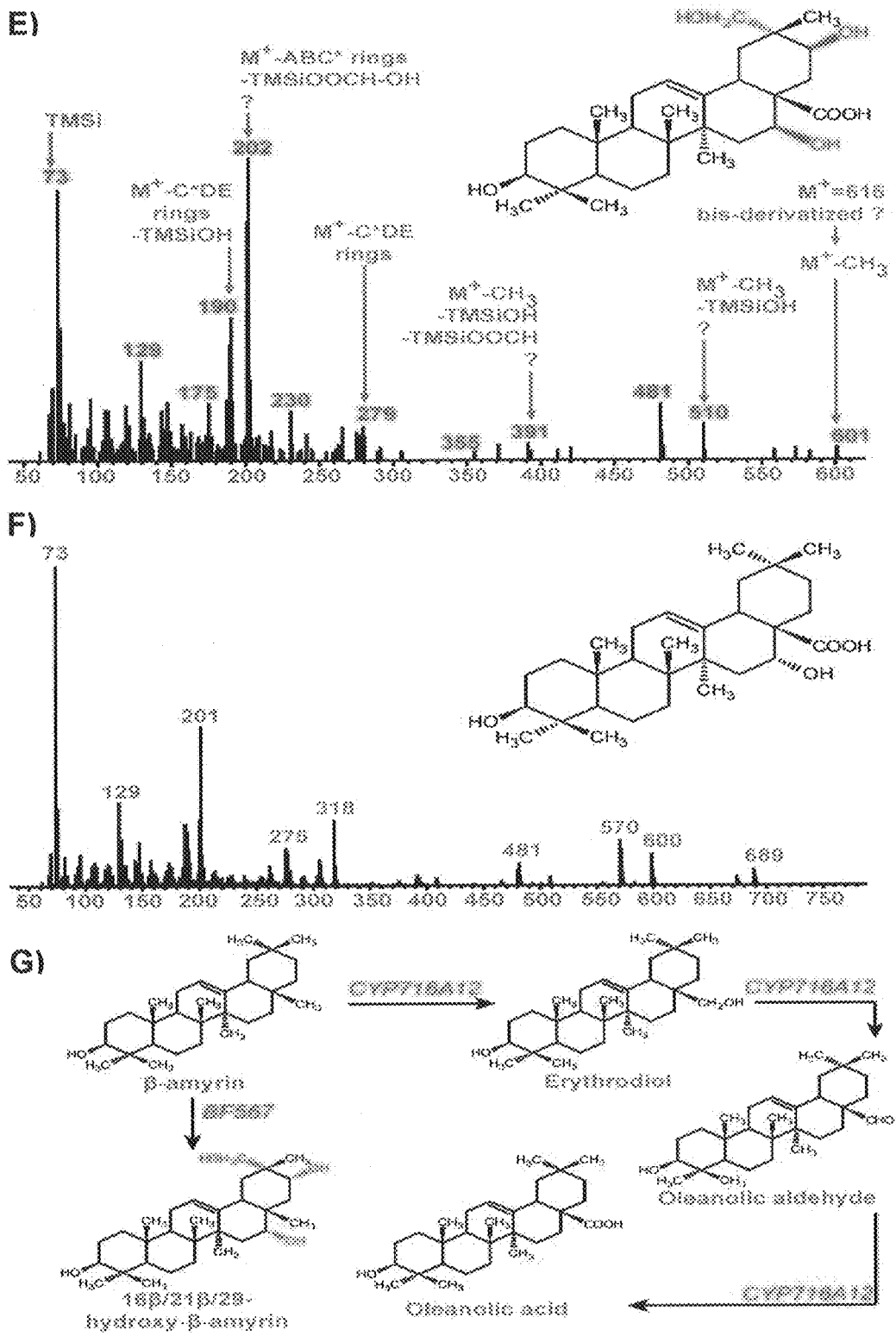

The spent medium of strain TM30 cultured in the presence of MβCD was analyzed by GC-MS and compared to the GC chromatograms of spent medium from strains TM9, and TM17 overexpressing pAG423[GAL1/CYP716A12] and pAG415[GAL1/AtATR1] in TM3. A unique peak was observed at 40.5 minutes in strain TM30 (FIG. 17, Panel A) but not TM9 (FIG. 17, Panel B) and TM17 (FIG. 17, Panel C), strongly supporting the fact that CYP716AO21 and CYP716A12 catalyze hydroxylations of two different carbons on β-amyrin. Additionally, the EI pattern of this peak suggested the presence of carboxyl and alcohol functions on β-amyrin, indicating the C-28 carboxylation by CYP716A12 and the C-16, C-21 or C-29 hydroxylation by CYP716AO21. Considering the close proximity of C-16 and C-28 on the β-amyrin molecule (FIG. 10) and the tentative annotation of CYP716AO21 as a homolog of CYP716A12, it was reasoned that CYP716AO21 might hydroxylate C-16 of β-amyrin. Therefore, the GC chromatogram and E1 pattern of an echinocystic acid standard (FIG. 17, Panel E) were compared with that of the new peak at 40.5 minutes in TM30 (FIG. 17, Panel D). However, the GC elution time and fragmentation of the new peak at 40.5 minutes did not match that of echinocystic acid (3β,16α-dihydroxyolean-28-oic acid), ruling out the possibility of a C-16 α-hydroxylation by CYP716AO21. Due to the absence of authentic 3β,16β- dihydroxyolean-28-oic acid, 3β,21β-dihydroxyolean-28-oic acid and 3β,29α-dihydroxyolean-28-oic acid standards, the identity of the combinatorial compound was unable to be confirmed.

In conclusion, using a combinatorial approach in *S. cerevisiae*, it was revealed that CYP716AO21 is not a C-28 oxygenase but a novel cytochrome P450 that encodes a β-amyrin 16β/21β/29α-hydroxylase involved in the synthesis of saikosaponins in *Bupleurum*.

Example 15. Combinatorial Biosynthesis Using ML593 and CYP716A12

Figure 18:
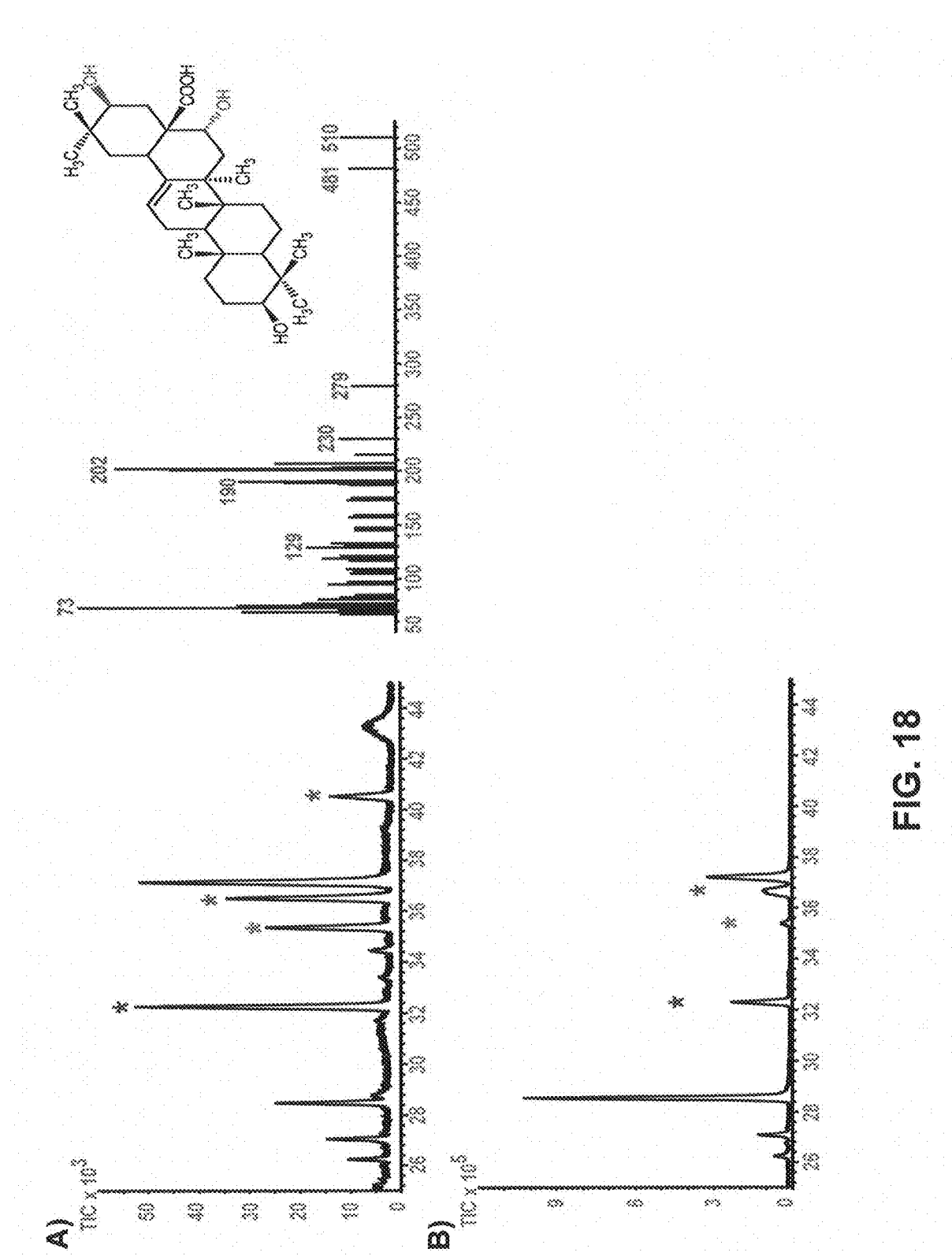
FIG. 18: GC chromatograms corresponding to: Panel A) Extraction from spent medium of strain TM31. Panel B) Extraction from spent medium of strain TM17. Panel C) Extraction from spent medium of strain TM21. Panel D) Extraction from spent medium of strain TM30. Panel E) An echinocystic acid standard. Right panel shows the mass spectra of indicated (*) peaks. Parts of structure highlighted in blue indicate probable hydroxylation positions.
Figure 18:
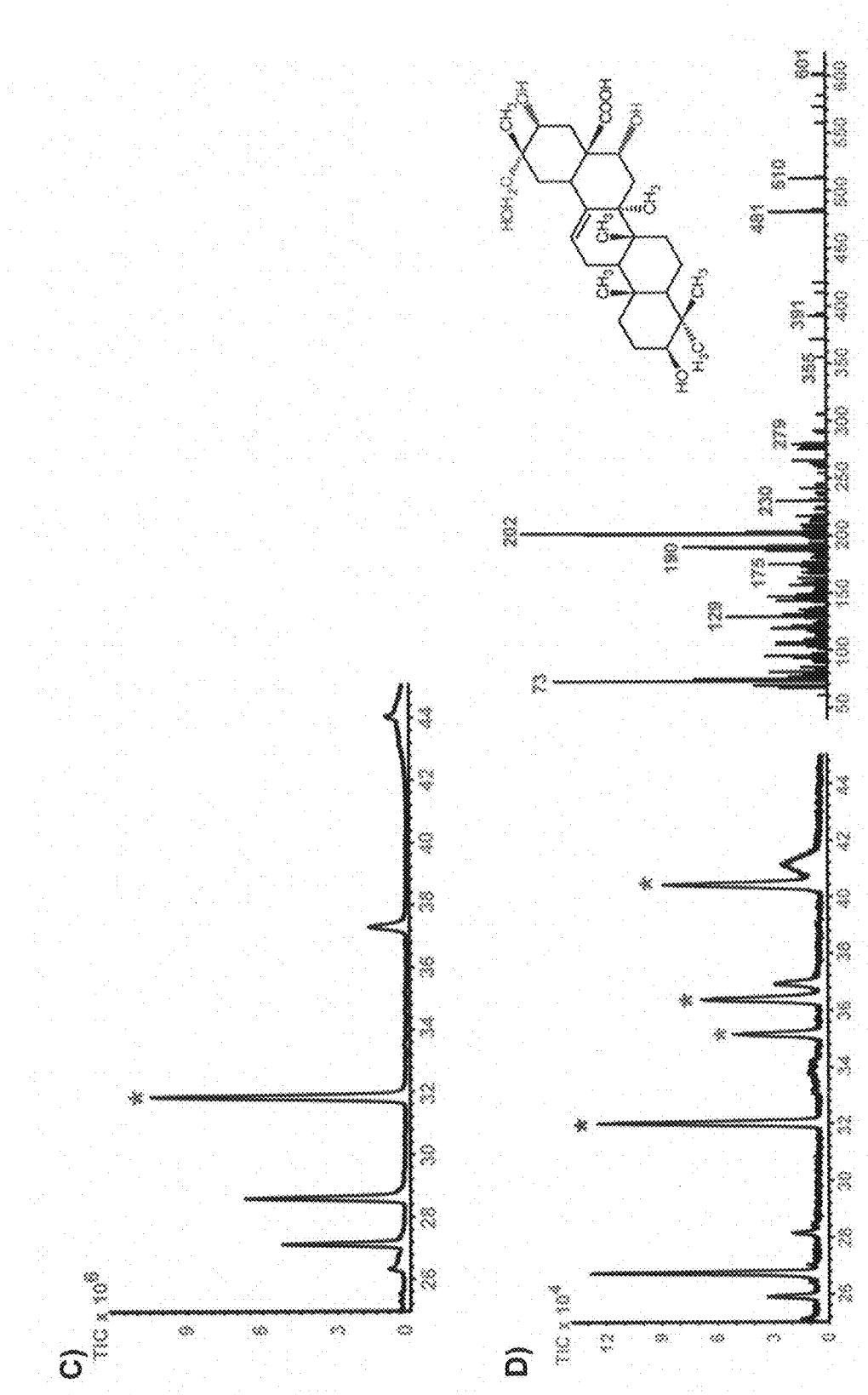
Figure 18:
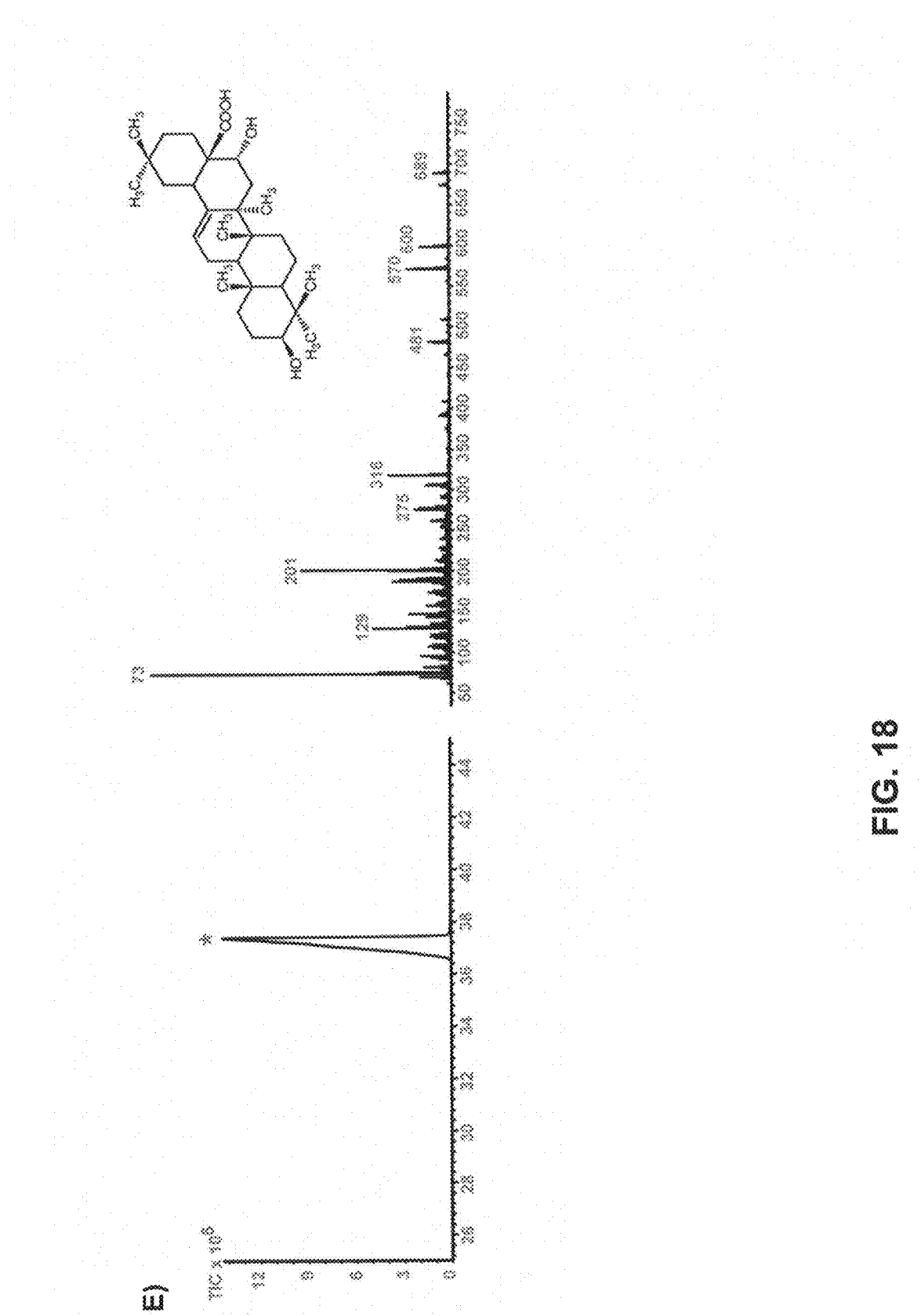

First, to confirm the identity of ML593 as a functional homolog of CYP716AO21, strain TM31 was generated, similar to strain TM30 (Table 4) (see Example 14). Strain TM31 was created by supertransforming TM3 with the plasmids pAG415[GAL1/AtATR1] and pAG423[GAL1/ML593-T2A-CYP716A12], where ML593 and CYP716A12 form a self-processing polyprotein stitched together by the 2A oligopeptide (de Felipe et al., 2006) and is expressed from a single GAL1 promoter. The strains TM31, TM17 and TM21 (Table 4) were cultured in the presence of MβCD and the spent medium was analyzed using GC-MS. Similar to strain TM30 (FIG. 18, Panel D), a new peak was observed eluting at 40.5 minutes in strain TM31 (FIG. 18, Panel A), but not the strains TM17 (FIG. 18, Panel B) and TM21 (FIG. 17, Panel C) expressing only the CytP450 CYP716A12 and ML593, respectively. From the EI pattern of this peak, its identity was confirmed as being the same as in strain TM30, which, together with the lack of homology with echinocystic acid, suggests a β-hydroxylation on C-21, the only remaining position commonly hydroxylated between CYP716AO21 and ML593. Although the CYP716AO21 and ML593 belong to different CytP450 subfamilies (CYP716A and CYP90B, respectively), in the yeast strain disclosed herein demonstrates the same catalytic activity.

Example 16. Combinatorial Biosynthesis Using ML593 and CYP88D6

Figure 19:
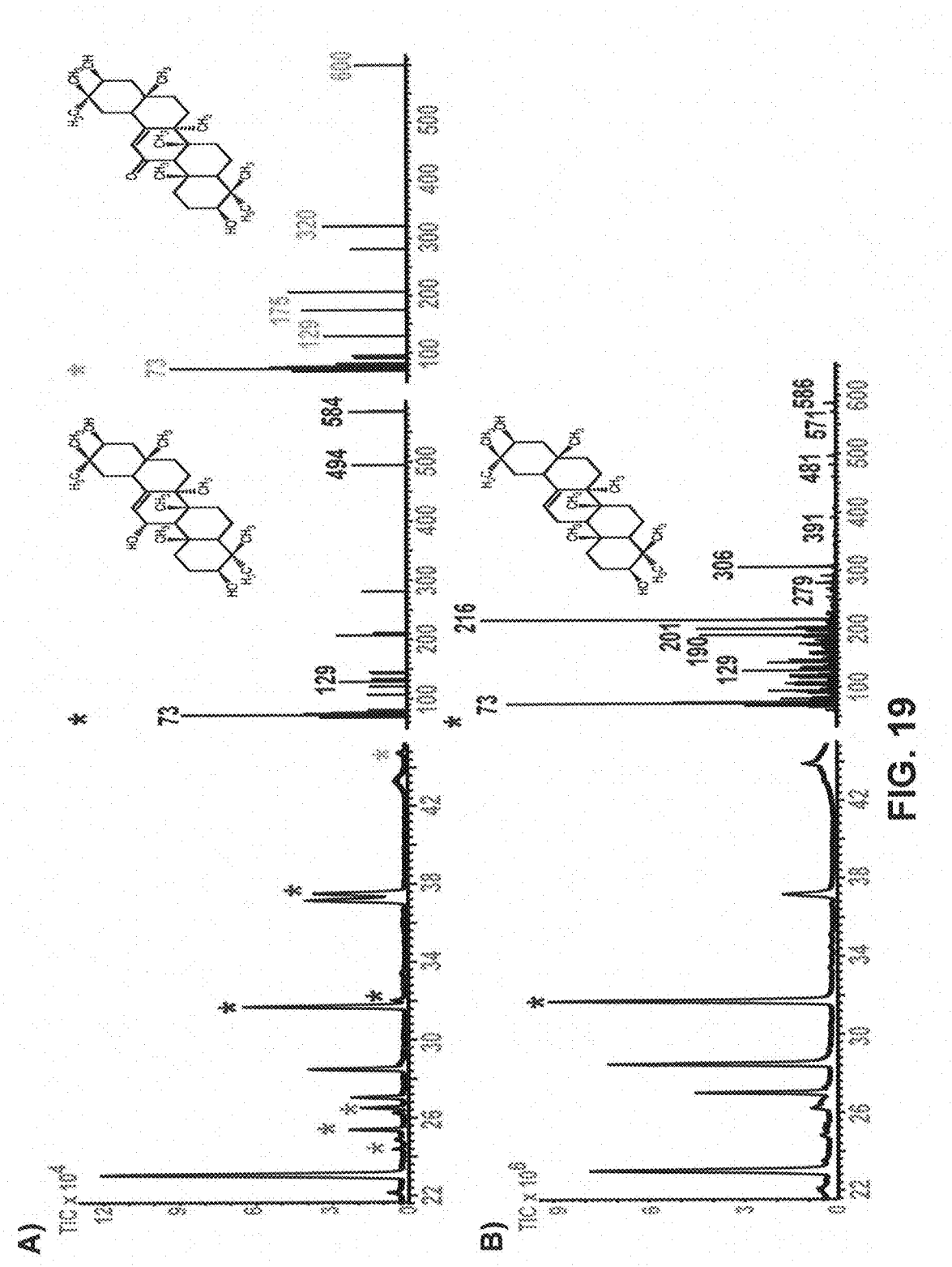
FIG. 19: GC chromatograms corresponding to: Panel A) Extraction from spent medium of strain TM32. Panel B) Extraction from spent medium of strain TM21. Panel C) Extraction from spent medium of strain TM18. Panel D) Extraction from spent medium of control strain TM27. Panel E) Mass spectra extracted from indicated (*) peaks of strain TM18 and TM32. Right panels show the mass spectra extracted from the indicated (*) peaks. Panel F) Oxidation of β-amyrin by ML593 and CYP88D6.
Figure 19:
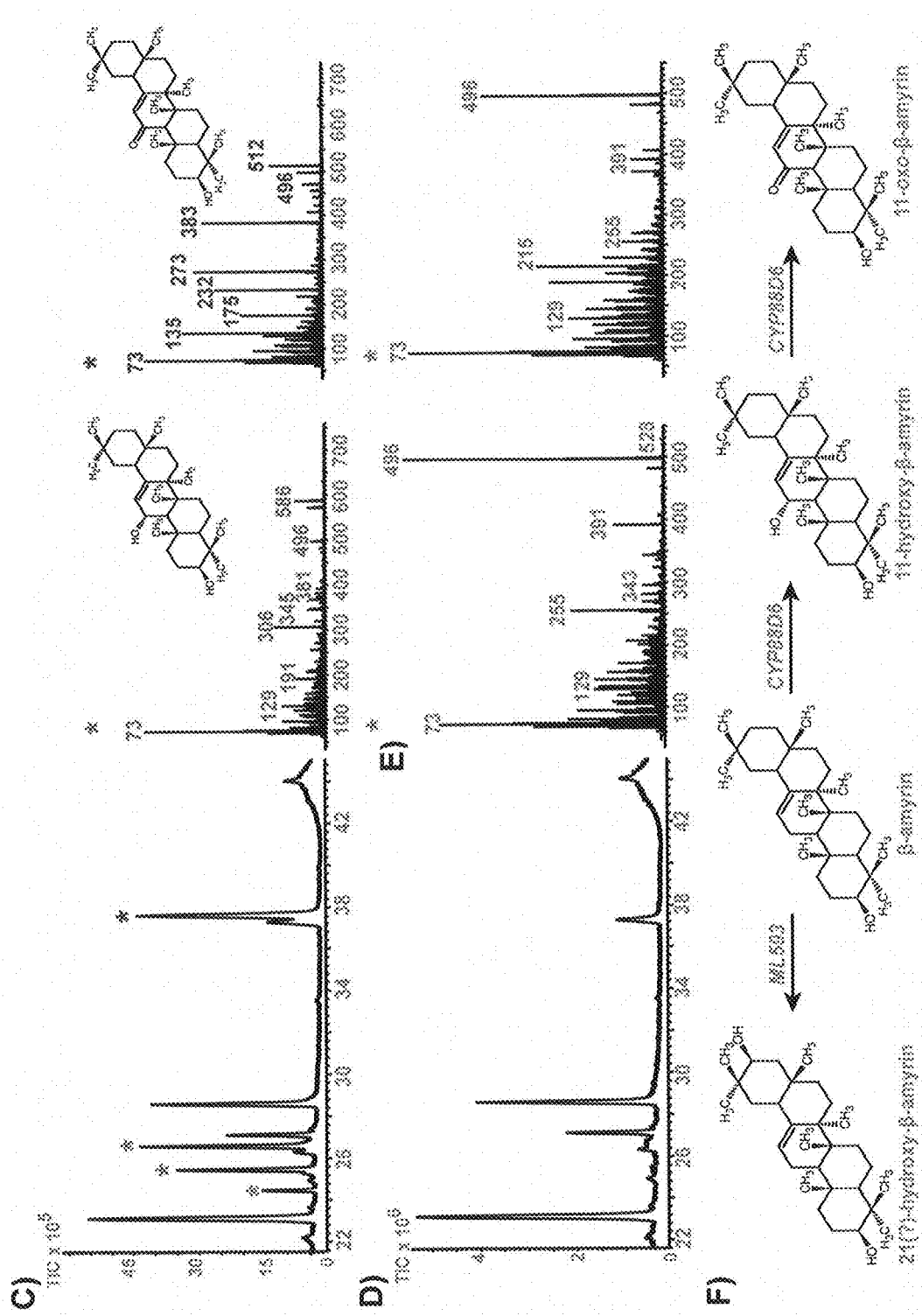

To generate a combinatorial scaffold using β-amyrin, ML593 (see Examples 12 and 13) and CYP88D6 were expressed in strain TM3. The CytP450 CYP88D6 (GenBank accession number AB433179; (Seki et al., 2008)) catalyzes a two-step oxidation of β-amyrin to 11-oxo-β-amyrin through an 11-hydroxy-β-amyrin intermediate. First, the activity of CYP88D6 was confirmed in the β-amyrin-producing strain by generating strain TM18 (Table 4) and culturing it in the presence of MβCD along with the control strain TM27. Therefore, the full-length open reading frame (FL-ORF) of CYP88D6 was PCR amplified using the primers P45 (GGGGACAAGTTTGTACAAAAAAGCAGGCT-TAATGGAAGTACATTGGGTTTG (SEQ ID NO:16))+P46 (GGGGACCACTTTGTACAAGAAAGCTGGG-TACTAAGCACATG AAACCTTTA (SEQ ID NO:17)) and cloned into pDONR221. The CytP450 CYP88D6 was then GATEWAY™ recombined into the high-copy number expression vector pAG423GAL-ccdB (Addgene plasmid 14149). GC chromatograms of the spent medium of strain TM18 showed the presence of four unique peaks (FIG. 19, Panel C) that were absent in the control strain TM27 (FIG. 19, Panel D). Two of these peaks eluting at 25.4 minutes and 37.5 minutes corresponded to 11-hydroxy β-amyrin and 11-oxo β-amyrin (Seki et al., 2008), respectively. The two remaining peaks eluting at 24.4 minutes and 26.6 minutes could not be assigned an identity despite their clear EI pattern. The highest mass observed in the mass spectra extracted from these peaks (FIG. 19, Panel E) was lower than that of trimethylsilylated β-amyrin (M+=498), indicating their possible non-triterpenoid origin. These additional peaks observed in our yeast strain were not reported when the CYP88D6 was expressed in a wild-type yeast strain expressing a β-amyrin synthase from *Lotus japonicus* (Seki et al., 2008).

Further, the strain TM32 was generated by supertransforming strain TM3 with the plasmids pAG415[GAL1/AtATR1] and pAG423[GAL1/ML593-T2A-CYP88D6], where ML593 and CYP88D6 are stitched together with the 2A oligopeptide, resulting in the generation of a self-processing polypeptide (de Felipe et al., 2006). The self-processing polyprotein of ML593 and CYP88D6 was generated by amplifying the FL-ORF of ML593 without a stop codon and having a 3'-overhang of the partial T2A sequence using the primer pair P39

(GGGGACAAGTTTGTACAAAAAAGCAGGCTTAATGTG
GGTAGTGGGATTA (SEQ ID NO: 12)) +

P47 (ACCGCAUGTTAGCAGACTTCCTCTGCCCTCCT
TGTTTTTCTTGGTGACCT (SEQ ID NO: 18)).

The FL-ORF of CYP88D6 was amplified with a 5'-overhang of the partial T2A sequence using the primers P48

(ATGCGGUGACGTCGAGGAGAATCCTGGCCCAATGGA
AGTACATTGGGTTT (SEQ ID NO: 19)) +

P46 (GGGGACCACTTTGTACAAGAAAGCTGGGTACT
AAGCACATGAAACCTTTA (SEQ ID NO: 17)), such that there was an overlap of 7 bp between the two amplified sequences. Since the primers P48 and P47 contain a Uracil each, the ML593 and CYP88D6 were PCR amplified using the Pfu Turbo Cx polymerase (Stratagene). The purified gel fragments were used for USER™ Cloning (New England Biolabs) to generate two fragments with complementary sticky ends, which were ligated in vitro using the T4 DNA ligase (Invitrogen). The ligated DNA product was used as template for amplification with the primers P39+P46. This amplicon was GATEWAY™ recombined into pDONR221, sequence verified and further recombined into pAG423GAL-ccdB to generate pAG423[GAL1/ML593-T2A-CYP88D6]. The spent medium of strain TM32 (FIG. 19, Panel A) cultured in the presence of MβCD was compared with that of strains TM21 (FIG. 1, Panel B) TM18 (FIG. 19, Panel C), and TM27 (FIG. 19, Panel D). Strain TM32 showed the presence of two unique peaks eluting at 32.1 minutes and 44.7 minutes that could correspond to 11α,21β(?)-dihydroxy β-amyrin and 11-oxo-21β(?)-hydroxy β-amyrin based on their EI pattern, respectively.

Example 17. Combinatorial Biosynthesis Using ML593 and CaDDS

In an attempt to generate a dammarenediol-producing yeast strain, the plasmid pESC-URA[GAL10/tHMG1; GAL1/CaDDS] was expressed, harboring a dammarenediol synthase gene (CaDDS) from *Centella asiatica* (GenBank accession number AY520818; (Kim et al., 2009)), in the sterol-modified yeast strain TM1, to generate strain TM33. The CaDDS was amplified with XhoI and NheI containing primers P43 (GGGGACAAGTTTGTA-CAAAAAAGCAGG CTTActcgagATGTGGAAGCT-GAAGATAGCA (SEQ ID NO:14))+P44 (GGGGAC-CACTTTGTACAAGAAAGCTGGGTTgctagcTCAATTG- GAGAGCCACAAGCG (SEQ ID NO:15)) to generate pESC-URA[GAL10/tHMG1; GAL1/CaDDS].

Figure 20:
FIG. 20: GC chromatograms corresponding to: Panel A) Extraction from spent medium of strain TM33. Panel B) Extraction from spent medium of control strain TM5. Panel C) A β-amyrin standard. Panel D) A α-amyrin standard. Right panels show the mass spectra extracted from the indicated (*) peaks. Panel E) Cyclization of 2,3-oxidosqualene by α-amyrin synthase (aAS), β-amyrin synthase (bAS), and dammarenediol synthase (DDS) to α-amyrin, β-amyrin and dammarenediol, respectively.
Figure 20:
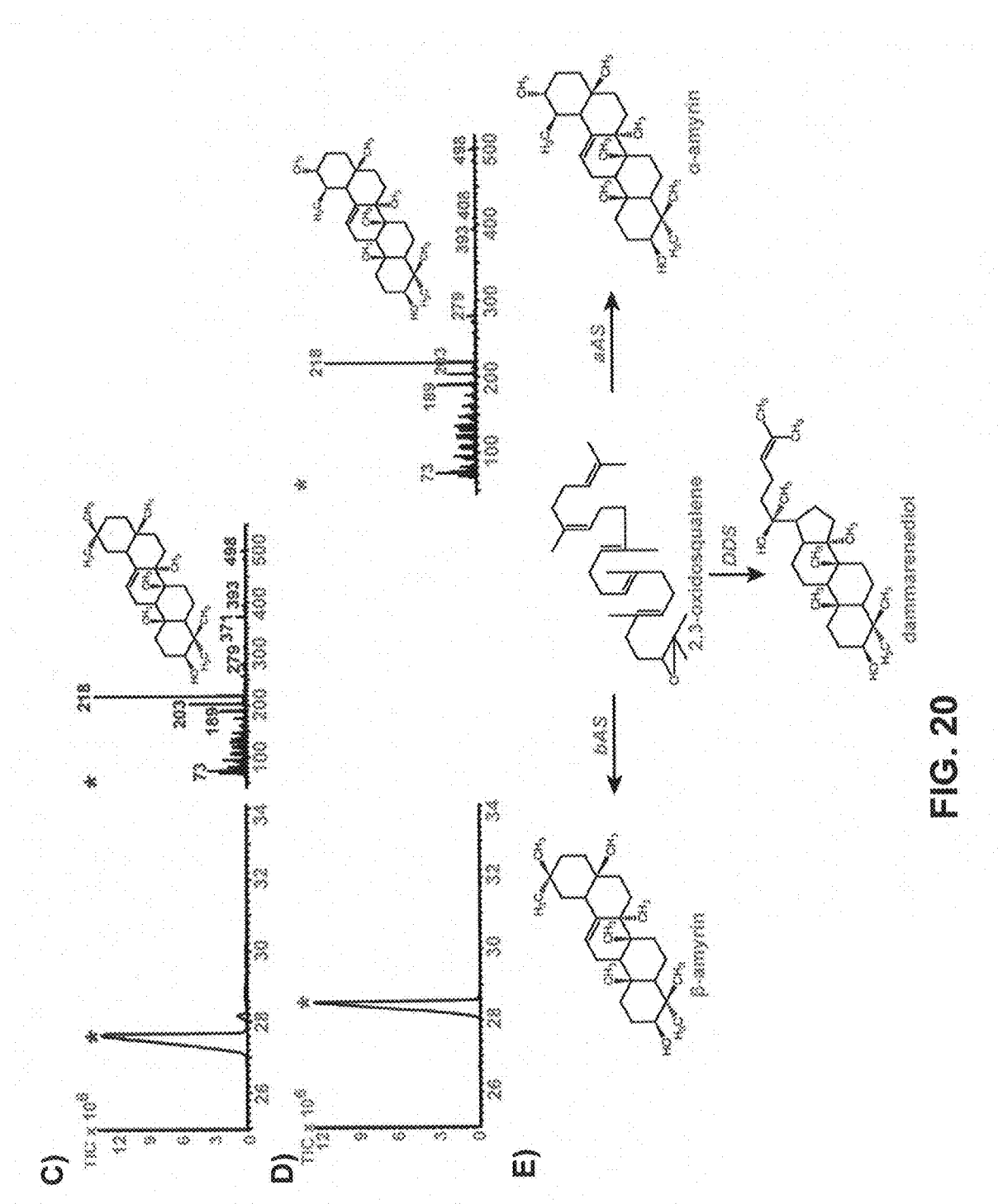

Strain TM33 and the control strain TM5 was cultured in medium containing MβCD and then analyzed the GC chromatograms obtained from the spent medium of both the strains. Unexpectedly, three new peaks were found in strain TM33 eluting at 27.2 minutes, 28.6 minutes, and 33.5 minutes (FIG. 20, Panel A) that were absent in the control strain TM5 (FIG. 20, Panel B). The identity of the peak eluting at 27.2 minutes was confirmed as β-amyrin (FIG. 20, Panel C), based on its elution time and its EI pattern. The peak at 28.6 minutes had a similar EI pattern as β-amyrin and was confirmed as α-amyrin by comparing to a standard (FIG. 20, Panel D). The E1 pattern of the peak at 33.5 minutes could be interpreted to dammarenediol-II (Spencer, 1981), but was not confirmed due to the lack of an authentic standard. Although, the CaDDS was initially reported as a putative bAS (Kim et al., 2005) and later characterized as a dammarenediol synthase (Kim et al., 2009), in the yeast strain disclosed herein, the gene was capable of cyclizing 2,3-oxidosqualene to both β-amyrin and dammarenediol in addition to a third product, α-amyrin. In the yeast strain disclosed herein, the relative amounts of α-amyrin, β-amyrin and dammarenediol-II were in the ratio of 8.8:1.1: 0.1, highlighting the very low dammarene synthase activity of CaDDS as opposed to its current characterization.

Figure 21:
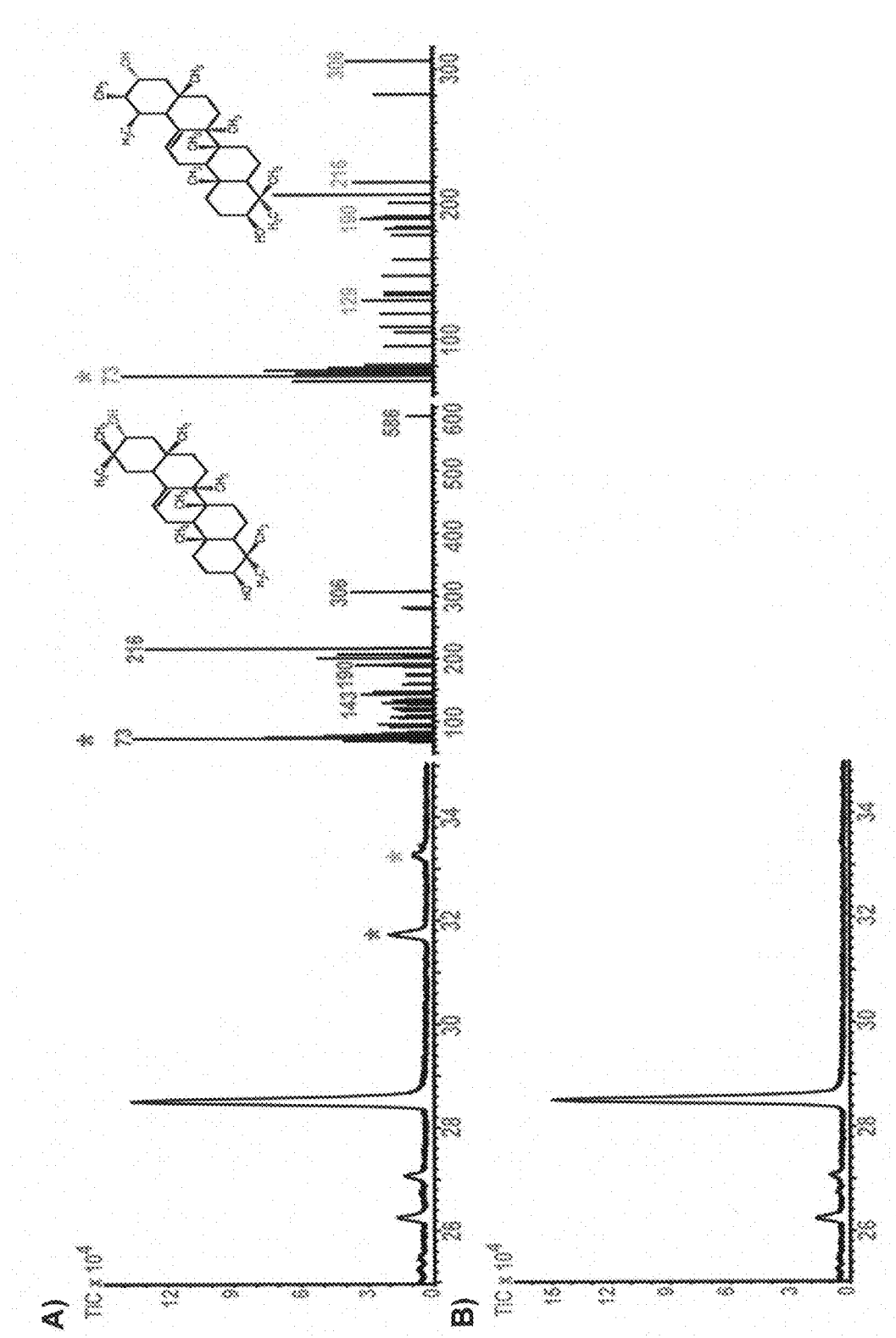
FIG. 21: GC chromatograms corresponding to: Panel A) Extraction from spent medium of strain TM37. Right panels show the mass spectra extracted from the indicated (*) peaks. Panel B) Extraction from spent medium of control strain TM38. Parts of structure in green indicate the putative hydroxylation position.

Strain TM37 was generated from strain TM33 by super-transforming with the plasmids pAG415[GAL1/AtATR1] and pAG423[GAL1/ML593] (see Table 4). The ML593 was characterized as a putative C-21 hydroxylase of β-amyrin (see Examples 12 and 13) and the substrate specificity of this CytP450 was determined by expressing it together with the multifunctional cyclase CaDDS. Strain TM37 and the control strain TM38 were cultured in the presence of MβCD and compared GC chromatograms for the presence of unique peaks. Two peaks were identified eluting at 31.8 minutes and 33.2 minutes in the spent medium of TM37 (FIG. 21, Panel A), but not the control strain TM38 (FIG. 21, Panel B). The E1 pattern of both these peaks were identical (FIG. 21, Panel A), and the peak at 31.8 minutes corresponded to (most likely) 21-hydroxy β-amyrin (see Examples 12 and 13). Therefore, the second peak at 33.2 minutes could correspond to 21-hydroxy α-amyrin, but was not confirmed due to the absence of an authentic standard.

TABLE 4

List of yeast strains generated and used in this study.

| Name | Construct |
|---|---|
| S288c BY4742 | MATa; his3Δ1; leu2Δ0; ura3Δ0; lys2Δ0 |
| TM1 | S288c BY4742; $P_{erg7}$::$P_{MET3}$-ERG7 |
| TM3 | TM1; pESC-URA[GAL10/tHMG1; GAL1/GgbAS](36.2 mg/L (β-amyrin) |
| TM5 | TM1; pESC-URA[GAL10/tHMG1] |
| TM7 | TM3; pAG423[GAL1/CYP716AO21], pAG425[GAL1/AtATR1] |
| TM8 | TM3; pAG423[GAL1/CYP716AO21], pAG305[GAL1/AtATR1] |
| TM9 | TM3; pAG423[GAL1/CYP716AO21], pAG415[GAL1/AtATR1] |
| TM10 | TM3; pAG423[GAL1/CYP716A12], pAG425[GAL1/AtATR1] |
| TM17 | TM3; pAG423[GAL1/CYP716A12], pAG415[GAL1/AtATR1] |
| TM21 | TM3; pAG423[GAL1/ML593], pAG415[GAL1/AtATR1] |
| TM26 | TM3; pAG423, pAG425[GAL1/AtATR1] |
| TM30 | TM3; pAG423[GAL1/CYP716AO21-T2A-CYP716A12], pAG415[GAL1/AtATR1] |
| TM27 | TM3; pAG423, pAG415[GAL1/AtATR1] |
| TM31 | TM3; pAG423[GAL1/ML593-T2A-CYP716A12], pAG415[GAL1/AtATR1] |
| TM18 | TM3; pAG423[GAL1/CYP88D6], pAG415[GAL1/AtATR1] |
| TM32 | TM3; pAG423[GAL1/ML593-T2A-CYP88D6], pAG415[GAL1/AtATR1] |
| TM33 | TM1; pESC-URA[GAL10/tHMG1; GAL1/CaDDS] |
| TM37 | TM33; pAG423[GAL1/ML593], pAG415[GAL1/AtATR1] |
| TM38 | TM33; pAG423, pAG415[GAL1/AtATR1] |

TABLE 5

Sequences of primers.

| Primer | Sequence (5' to 3') | SEQ ID NO |
|---|---|---|
| P19 | GGGGACAAGTTTGTACAAAAAAGCAGG CTTAATGGAACTTTCTATCACT | 5 |
| P20 | GGGGACCACTTTGTACAAGAAAGCTGG GTATTAAGATGGAGATTTGTG | 6 |
| P22 | GGGGACCACTTTGTACAAGAAAGCTGG GTATTAAGCTTTGTGTGGATAAAGGCG | 7 |
| P23 | ACCGCAUGTTAGCAGACTTCCTCTGCC CTCAGATGGAGATTTGTGGGGAT | 8 |
| P24 | ATGCGGUGACGTCGAGGAGAATCCTGG CCCAATGGAGCCTAATTTCTATC | 9 |
| P27 | CTCTTGCATTCAATCCGAAAC | 10 |
| P28 | AGCAAAGAATGCCTTGGCTA | 11 |
| P39 | GGGGACAAGTTTGTACAAAAAAGCAGG CTTAATGTGGGTAGTGGGATTA | 12 |
| P40 | GGGGACCACTTTGTACAAGAAAGCTGG GTATCACTTGTTTTTCTTGGT | 13 |
| P43 | GGGGACAAGTTTGTACAAAAAAGCAGG CTTActcgagATGTGGAAGCTGAAGAT AGCA | 14 |
| P44 | GGGGACCACTTTGTACAAGAAAGCTGG GTTgctagcTCAATTGGAGAGCCACAA GCG | 15 |
| P45 | GGGGACAAGTTTGTACAAAAAAGCAGG CTTAATGGAAGTACATTGGGTTTG | 16 |
| P46 | GGGGACCACTTTGTACAAGAAAGCTGG GTACTAAGCACATGAAACCTTTA | 17 |
| P47 | ACCGCAUGTTAGCAGACTTCCTCTGCC CTCCTTGTTTTTCTTGGTGACCT | 18 |

TABLE 5-continued

Sequences of primers.

| Primer | Sequence (5' to 3') | SEQ ID NO |
|---|---|---|
| P48 | ATGCGGUGACGTCGAGGAGAATCCTGG CCCAATGGAAGTACATTGGGTTT | 19 |

The sequences in lower case represent the restriction recognition site used for restriction enzyme-mediated cloning. The underlined sequence corresponds to T2A partial sequences.

TABLE 6

List of sequences

| | SEQ ID NO | Nucleotide sequence |
|---|---|---|
| CYP716A021 | 1 | ATGGAACTTTCTATCACTCTGATGCTTA TTTTCTCAACAACCATCTTCTTTATATT TCGTAATGTGTACAACCATCTCATCTCT AAACACAAAAACTATCCCCCTGGAAGTA TGGGCTTGCCTTACATTGGCGAAACACT TAGTTTCGCGAGATACATCACCAAAGGA GTCCCTGAAAAATTCGTAATAGAAAGAC AAAAGAAATATTCAACAACAATATTTAA GACCTCCTTGTTCGGAGAAAACATGGTG GTGTTGGGCAGTGCAGAGGGCAACAAAT TTATTTTTGGAAGCGAGGAGAAGTATTT ACGAGTGTGGTTTCCAAGTTCTGTGGAC AAAGTGTTCAAAAAATCTCATAAGAGAA CGTCGCAGGAAGAAGCTATTAGGTTGCG CAAAAACATGGTGCCATTTCTCAAAGCA GATTTGTTGAGAAGTTATGTACCAATAA TGGACACATTTATGAAACAACATGTGAA CTCGCATTGGAATTGCGAGACCTTGAAG GCTTGTCCTGTGATCAAGGATTTTACGT TTACTTTAGCTTGTAAACTTTTTTTTAG TGTAGACAATCCTTTGGAGCTAGAGAAG TTAATCAAGCTATTTGTGAATATAGTGA ATGGCCTCCTTACGGTCCCTATTGATCT CCCGGGGACAAAATTTAGAGGAGTTATA AAGAGTGTCAAGACTATTCGCCATGCGC TTAAAGTGTTGATCAGGCAACGAAAGGT GGATATTAGAGAGAAAAGAGCCACACCT ACGCAAGATATATTGTCGATAATGCTGG CACAGGCTGAGGACGAGAACTATGAAAT GAATGATGAAGATGTGGCCAATGACTTT CTTGCAGTTTTGCTTGCTAGTTATGATT CTGCCAATACTACACTCACCATGATTAT GAAATATCTTGCTGAATATCCCGAAATG TATGATCGAGTTTTCAGAGAACAAATGG AGGTGGCAAAGACGAAAGGAAAAAGATGA ATTACTCAACTTGGACGACTTGCAAAAG ATGAATTATACTTGGAATGTAGCTTGTG AAGTACTGAGAATTGCAACACCAACGTT CGGAGCATTCAGAGAGGTTATTGCAGAT TGTACATACGAAGGGTACACCATACCAA AAGGCTGGAAGCTATATTATGCCCCGCG TTTTACCCATGGAAGTGCAAAATACTTT CAAGATCCAGAGAAATTTGATCCATCGC GATTTGAAGGTGATGGTGCGCCTCCTTA TACATTCGTTCCATTCGGAGGAGGGCTC CGGATGTGCCCTGGATACAAGTATGCAA AGATTATAGTACTAGTGTTCATGCACAA TATAGTTACAAAGTTCAAATGGGAGAAA GTTAACCCTAATGAGAAAATGACAGTAG GAATCGTATCAGCGCCAAGTCAAGGACT TCCACTGCGTCTCCATCCCCACAAATCT CCATCTTAA |
| ML593 | 2 | ATGTGGGTAGTGGGATTAATTGGTGTGG CTGTGGTAACAATATTGATAACTCAGTA TGTATACAAATGGAGAAATCCAAAGACT |

TABLE 6-continued

List of sequences

| | SEQ ID NO | |
|---|---|---|
| | | GTGGGTGTTCTGCCACCTGGTTCAATGG GTCTGCCTTTGATCGGGGAGACTCTTCA ACTTCTCAGCCGTAATCCATCCTTGGAT CTTCATCCTTTCATCAAGAGCAGAATCC AAAGATATGGGCAGATATTCGCGACCAA TATCGTAGGTCGACCCATAATAGTAACC GCTGATCCGCAGCTCAATAATTACCTTT TCCAACAAGAAGGAAGAGCAGTAGAACT GTGGTACTTGGACAGCTTTCAAAAGCTA TTTAACTTAGAAGGTGCAAACAGGCCGA ACGCAGTTGGTCACATTCACAAGTACGT TAGAAGTGTATACTTGAGTCTCTTTGGC GTCGAGAGCCTTAAAACAAAGTTGCTTG CCGATATTGAGAAAACAGTCCGCAAAAA TCTTATTGGTGGGACAACCAAAGGCACC TTTGATGCAAAACATGCTTCTGCCAATA TGGTTGCTGTTTTTGCTGCAAAATACTT GTTCGGACATGATTACGAGAAATCGAAA GAAGATGTAGGCAGCATAATCGACAACT TCGTACAAGGTCTTCTCGCATTCCCATT GAATGTTCCCGGTACAAAGTTCCACAAA TGTATGAAGGACAAGAAAAGGCTGGAAT CAATGATCACTAACAAGCTAAAGGAGAG AATAGCTGATCCGAACAGCGGACAAGGG GATTTCCTTGATCAAGCAGTGAAAGACT TGAATAGCGAATTCTTCATAACAGAGAC TTTTATCGTTTCGGTGACGATGGGAGCT TTATTTGCGACGGTTGAATCGGTTTCGA CAGCAATTGGACTAGCTTTCAAGTTTTT TGCAGAGCACCCCTGGGTTTTGGATGAC CTCAAGGCTGAGCATGAGGCTGTCCTTA GCAAAAGAGAGGATAGAAATTCACCTCT CACGTGGGACGAATATAGATCGATGACA CACACGATGCACTTTATCAATGAAGTCG TCCGTTTGGGAAATGTTTTTCCTGGAAT TTTGAGGAAAGCACTGAAAGATATTCCA TATAATGGTTATACAATTCCGTCCGGTT GGACCATTATGATTGTGACCTCTACCCT TGCGATGAACCCTGAGATATTCAAGGAT CCTCTTGCATTCAATCCGAAACGTTGGC GGGATATTGATCCCGAAACTCAAACTAA AAACTTTATGCCTTTCGGTGGTGGGACG AGACAATGCGCAGGTGCAGAGCTAGCCA AGGCATTCTTTGCTACCTTCCTCCATGT TTTAATCAGCGAATATAGCTGGAAGAAA GTGAAGGGAGGAAGCGTTGCTCGGACAC CTATGTTAAGTTTTGAAGATGGCATATT TATTGAGGTCACCAAGAAAAACAAGTGA |

Amino acid sequence

| CYP716A021 | 3 | MELSITLMLIFSTTIFFIFRNVYNHLIS KHKNYPPGSMGLPYIGETLSFARYITKG VPEKFVIERQKKYSTTIFKTSLFGENMV VLGSAEGNKFIFGSEEKYLRVWFPSSVD KVFKKSHKRTSQEEAIRLRKNMVPFLKA DLLRSYVPIMDTFMKQHVNSHWNCETLK ACPVIKDFTFTLACKLFFSVDNPLELEK LIKLFVNIVNGLLTVPIDLPGTKFRGVI KSVKTIRHALKVLIRQRKVDIREKRATP TQDILSIMLAQAEDENYEMNDEDVANDF LAVLLASYDSANTTLTMIMKYLAEYPEM YDRVFREQMEVAKTKGKDELLNLDDLQK MNYTWNVACEVLRIATPTFGAFREVIAD CTYEGYTIPKGWKLYYAPRFTHGSAKYF QDPEKFDPSRFEGDGAPPYTFVPFGGGL RMCPGYKYAKIIVLVFMHNIVTKFKWEK VNPNEKMTVGIVSAPSQGLPLRLHPHKS PS |
| ML593 | 4 | MWVVGLIGVAVVTILITQYVYKWRNPKT VGVLPPGSMGLPLIGETLQLLSRNPSLD LIAPFIKSRIQRYGQIFATNIVGRPIIV TADPQLNNYLFQQEGRAVELWYLDSFQK LFNLEGANRPNAVGHIHKYVRSVYLSLF |

TABLE 6-continued

List of sequences

| SEQ ID NO | |
|---|---|
| | GVESLKTKLLADIEKTVRKNLIGGTTKG<br>TFDAKHASANMVAVFAAKYLFGHDYEKS<br>KEDVGSIIDNFVQGLLAFPLNVPGTKFH<br>KCMKDKKRLESMITNKLKERIADPNSGQ<br>GDFLDQAVKDLNSEFFITETFIVSVTMG<br>ALFATVESVSTAIGLAFKFFAEHPWVLD<br>DLKAEHEAVLSKREDRNSPLTWDEYRSM<br>THTMHFINEVVRLGNVFPGILRKALKDI<br>PYNGYTIPSGWTIMIVTSTLAMNPEIFK<br>DPLAFNPKRWRDIDPETQTKNFMPFGGG<br>TRQCAGAELAKAFFATFLHVLISEYSWK<br>KVKGGSVARTPMLSFEDGIFIEVTKKNK |

REFERENCES

Arthington-Skaggs B. A., H. Jradi, T. Desai, and C. J. Morrison (1999). Quantitation of ergosterol content: novel method for determination of fluconazole susceptibility of *Candida albicans*. *Journal of Clinical Microbiology* 37:3332-3337.

Asadollahi M. A., J. Maury, K. Møller, K. F. Nielsen, M. Schalk, A. Clark, and J. Nielsen (2008). Production of plant sesquiterpenes in *Saccharomyces cerevisiae*: effect of ERG9 repression on sesquiterpene biosynthesis. *Biotechnology and Bioengineering* 99:666-677.

Ashour M. L., and M. Wink (2011). Genus *Bupleurum*: a review of its phytochemistry, pharmacology and modes of action. *Journal of Pharmacy and Pharmacology* 63:305-321.

Augustin J. M., V. Kuzina, S. B. Andersen, S. Bak. Molecular activities, biosynthesis and evolution of triterpenoid saponins. *Phytochemistry*. 2011 April; 72(6):435-57. Epub 2011 Feb. 16.

Burnouf-Radosevich M., N. E. Delfel, and R. England (1985). Gas chromatography-mass sepctrometry of oleanane- and ursane-type triterpones-application to *Chenopodium Quinoa* triterpenes. *Phytochemistry* 24:2063-2066.

Carelli M., E. Biazzi, F. Panara, A. Tava, L. Scaramelli, A. Porceddu, N. Graham, M. Odoardi, E. Piano, S. Arcioni, S. May, C. Scotti, and O. Calderini (2011). *Medicago truncatula* CYP716A12 is a multifunctional oxidase involved in the biosynthesis of hemolytic saponins. *The Plant Cell* 23:3070-3081.

de Felipe P., G. A. Luke, L. E. Hughes, D. Gani, C. Halpin, and M. D. Ryan (2006). E unum pluribus: multiple proteins from a self-processing polyprotein. *Trends in Biotechnology* 24:68-75.

Faizal A., E. Lambert, K. Foubert, S. Apers, and D. Geelen (2011). In vitro propagation of four saponin-producing *Maesa* species. *Plant Cell Tissue and Organ Culture* 106:215-223.

Foubert K., F. Cuyckens, K. Vleeschouwer, M. Theunis, A. Vlietinck, L. Pieters, and S. Apers (2010). Rapid quantification of 14 saponins of *Maesa lanceolata* by UPLC-MS/MS. *Talanta* 81:1258-1263.

Fujita S., T. Ohnishi, B. Watanabe, T. Yokota, S. Takatsuto, S. Fujioka, S. Yoshida, K. Sakata, and M. Mizutani (2006). *Arabidopsis* CYP90B1 catalyzes the early C-22 hydroxylation of C27, C28 and C29 sterols. *The Plant Journal* 45:765-774.

Guo S. J., L. Kenne, L. N. Lundgren, B. Ronnberg, and B. G. Sundquist (1998). Triterpenoid saponins from *Quillaja saponaria*. *Phytochemistry* 48:175-180.

Fukushima E. O., H. Seki, K. Ohyama, E. Ono, N. Umemoto, M. Mizutani, K. Saito, and T. Muranaka (2011). CYP716A subfamily members are multifunctional oxidases in triterpenoid biosynthesis. *Plant and Cell Physiology* 52:2050-2061.

Fukushima E. O., H. Seki, S. Sawai, M. Suzuki, K. Ohyama, K. Saito, and T. Muranaka (2013). Combinatorial biosynthesis of legume natural and rare triterpenoids in engineered yeast. *Plant and Cell Physiology* (doi:10.1093/pcp/pct015).

Han J. Y., H. J. Kim, Y. S. Kwon, and Y. E. Choi (2011). The Cyt P450 enzyme CYP716A47 catalyzes the formation of protopanaxadiol from dammarenediol-II during ginsenoside biosynthesis in *Panax ginseng*. *Plant and Cell Physiology* 52:2062-2073.

Han J. Y., H. S. Hwang, S. W. Choi, H. J. Kim, and Y. E. Choi (2012). Cytochrome P450 CYP716A53v2 catalyzes the formation of protopanaxatriol from protopanaxadiol during ginsenoside biosynthesis in *Panax ginseng*. *Plant and Cell Physiology*.

Hayashi H., P. Huang, A. Kirakosyan, K. Inoue, N. Hiraoka, Y. Ikeshiro, T. Kushiro, M. Shibuya, and Y. Ebizuka (2001). Cloning and characterization of a cDNA encoding beta-amyrin synthase involved in glycyrrhizin and soyasaponin biosyntheses in licorice. *Biological and Pharmaceutical Bulletin* 24:912-916.

Herrera J. B., B. Bartel, W. K. Wilson, and S. P. Matsuda (1998). Cloning and characterization of the *Arabidopsis thaliana* lupeol synthase gene. *Phytochemistry* 49:1905-1911.

Huang L., J. Li, H. Ye, C. Li, H. Wang, B. Liu, and Y. Zhang (2012). Molecular characterization of the pentacyclic triterpenoid biosynthetic pathway in *Catharanthus roseus*. *Planta*.

Huhman D. V., L. W. Sumner (2002). Metabolic profiling of saponins in *Medicago sativa* and *Medicago truncatula* using HPLC coupled to an electrospray ion-trap mass spectrometer. *Phytochemistry*. 2002 February; 59(3):347-60.

Huhman D. V., M. A. Berhow, and L. W. Sumner (2005). Quantification of saponins in aerial and subterranean tissues of *Medicago truncatula*. *J. Agric. Food Chem.* 2005 Mar. 23; 53(6):1914-20.

Iturbe-Ormaetxe I., K. Haralampidis, K. Papadopoulou, and A. E. Osbourn (2003). Molecular cloning and characterization of triterpene synthases from *Medicago truncatula* and *Lotus japonicus*. *Plant Mol. Biol.* 2003 March; 51(5):731-43.

Kim O. T., M. Y. Kim, S. M. Huh, D. G. Bai, J. C. Ahn, and B. Hwang (2005). Cloning of a cDNA probably encoding oxidosqualene cyclase associated with asiaticoside biosynthesis from *Centella asiatica* (L.) Urban. *Plant Cell Reports* 24:304-311.

Kim O. T., J. W. Lee, K. H. Bang, Y. C. Kim, D. Y. Hyun, S. W. Cha, Y. E. Choi, M. L. Jin, and B. Hwang (2009). Characterization of a dammarenediol synthase in *Centella asiatica* (L.) Urban. *Plant Physiology and Biochemistry* 47:998-1002.

Kirby J., D. W. Romanini, E. M. Paradise, and J. D. Keasling (2008). Engineering triterpene production in *Saccharomyces cerevisiae*-β-amyrin synthase from *Artemisia annua*. *The FEBS Journal* 275:1852-1859.

Kunii M., Y. Kitahama, E. O. Fukushima, H. Seki, T. Muranaka, Y. Yoshida, and Y. Aoyama (2012). β-Amyrin oxidation by oat CYP51H10 expressed heterologously in yeast cells: the first example of CYP51-dependent metabolism other than the 14-demethylation of sterol precursors. *Biological and Pharmaceutical Bulletin* 35:801-804.

Kushiro T., M. Shibuya, and Y. Ebizuka (1998). Beta-amyrin synthase—cloning of oxidosqualene cyclase that catalyzes the formation of the most popular triterpene among higher plants. *Eur. J. Biochem.* 1998 Aug. 15; 256 (1):238-44.

Li L., H. Cheng, J. Gai, and D. Yu (2007). Genome-wide identification and characterization of putative cytochrome P450 genes in the model legume *Medicago truncatula. Planta* 226:109-123.

Manguro L. O. A., J. O. Midiwo, L. F. Tietze, and P. Hao (2011). Triterpene saponins of *Maesa lanceolata* leaves. *Arkivoc*, 172-198.

Morita M., M. Shibuya, T. Kushiro, K. Masuda, and Y. Ebizuka (2000). Molecular cloning and functional expression of triterpene synthases from pea (*Pisum sativum*) new alpha-amyrin-producing enzyme is a multifunctional triterpene synthase. *Eur. J. Biochem.* 2000 June; 267(12): 3453-60.

Polakowski T., U. Stahl, and C. Lang (1998). Overexpression of a cytosolic hydroxymethylglutaryl-CoA reductase leads to squalene accumulation in yeast. *Applied Microbiology and Biotechnology* 49:66-71.

Pollier J., K. Morreel, D. Geelen, and A. Goossens (2011). Metabolite profiling of triterpene saponins in *Medicago truncatula* hairy roots by liquid chromatography Fourier transform ion cyclotron resonance mass spectrometry. *Journal of Natural Products* 74:1462-1476.

Pollier J., and A. Goossens (2012). Oleanolic acid. *Phytochemistry* 77:10-15.

Pollier J., M. González-Guzmán, W. Ardiles-Diaz, D. Geelen, and A. Goossens (2011b). An integrated PCR colony hybridization approach to screen cDNA libraries for full-length coding sequences. *PLoS ONE* 6:e24978.

Reed J. R., and W. L. Backes (2012). Formation of P450 P450 complexes and their effect on P450 function. *Pharmacology & Therapeutics* 133:299-310.

Rickling B., and K. W. Glombitza (1993). Saponins in the leaves of birch? Hemolytic dammarane triterpenoid esters of *Betula pendula. Planta medica* 59:76-79.

Rischer H., M. Oršič, T. Seppänen-Laakso, M. Katajamaa, F. Lammertyn, W. Ardiles-Diaz, M. C. Van Montagu, D. Inzé, K. M. Oksman-Caldentey, and A. Goossens (2006). Gene-to-metabolite networks for terpenoid indole alkaloid biosynthesis in *Catharanthus roseus* cells. *Proc. Natl. Acad. Sci. U.S.A.* 103:5614-5619.

Seki H., K. Ohyama, S. Sawai, M. Mizutani, T. Ohnishi, H. Sudo, T. Akashi, T. Aoki, K. Saito, and T. Muranaka (2008). Licorice beta-amyrin 11-oxidase, a cytochrome P450 with a key role in the biosynthesis of the triterpene sweetener glycyrrhizin. *Proc. Natl. Acad. Sci. U.S.A.* 105:14204-14209.

Seki H., S. Sawai, K. Ohyama, M. Mizutani, T. Ohnishi, H. Sudo, E. O. Fukushima, T. Akashi, T. Aoki, K. Saito, and T. Muranaka (2011). Triterpene functional genomics in licorice for identification of CYP72A154 involved in the biosynthesis of glycyrrhizin. *Plant Cell* 23:4112-4123.

Sabater-Jara Sabater-Jara A. B., L. Almagro, S. Belchí-Navarro, M. A. Ferrer, A. R. Barceló, and M. A. Pedreño (2010). Induction of sesquiterpenes, phytoesterols and extracellular pathogenesis-related proteins in elicited cell cultures of *Capsicum annuum. J. Plant Physiol.* 167: 1273-81.

Sindambiwe J. B., M. Calomme, S. Geerts, L. Pieters, A. J. Vlietinck, and D. A. VandenBerghe (1998). Evaluation of biological activities of triterpenoid saponins from *Maesa lanceolata. Journal of Natural Products* 61:585-590.

Sparg S. G., M. E. Light, and J. van Staden (2004). Biological activities and distribution of plant saponins. *J. Ethnopharmacol.* 2004 October; 94(2-3):219-43.

Spencer G. F. (1981). Dammarenediol II esters from *Cacalia atriplicifolia* L. seed oil. *Journal of Natural Products* 44:166-168.

Stiti N., S. Triki, and M. A. Hartmann (2007). Formation of triterpenoids throughout *Olea europaea* fruit ontogeny. *Lipids* 42:55-67.

Sun H. X., Y. Xie, Y. P. Ye (2009). Advances in saponin-based adjuvants. *Vaccine.* 2009 Mar. 13; 27(12):1787-96. Epub 2009 Feb. 7.

Suzuki H., L. Achnine, R. Xu, S. P. Matsuda, and R. A. Dixon (2002). A genomics approach to the early stages of triterpene saponin biosynthesis in *Medicago truncatula. Plant J.* 2002 December; 32(6):1033-48.

Tava A., C. Scotti, and P. Avato (2011). Biosynthesis of saponins in the genus *Medicago. Phytochemistry Reviews* 10:459-469.

Toivounen L. (1993). *Biotechnol. Prog.* 9:12.

Turpen T. H. (1999). Tobacco mosaic virus and the virescence of biotechnology. *Philos. Trans. R. Soc. Lond. B. Biol. Sci.* 1999 Mar. 29; 354(1383):665-73.

Vanhala L. et al. (1995). *Plant Cell Rep.* 14:236.

Verpoorte R. et al. (1999). *Biotechnol. Lett.* 21:467.

Vincken J. P., L. Heng, A. de Groot, H. Gruppen (2007). Saponins, classification and occurrence in the plant kingdom. *Phytochemistry.* 2007 February; 68(3):275-97.

Vuylsteke M., J. D. Peleman, and M. J. van Eijk (2007). AFLP®-based transcript profiling (cDNA-AFLP®) for genome-wide expression analysis. *Nat. Protoc.* 2:1399-1413.

Zou K., S. Zhu, C. Tohda, S. Cai, and K. Komatsu. (2002). Dammarane-type triterpene saponins from *Panax japonicus. Journal of Natural Products* 65:346-351.

The invention claimed is:

1. A method for the intracellular production and extracellular secretion of triterpenoid sapogenins in a genetically engineered yeast culture, the method comprising:
incubating genetically engineered yeast cells that express an exogenous regulatory or biosynthetic enzyme of the sapogenin biosynthesis pathway in a culture medium comprising randomly methylated cyclodextrins, hydroxypropylated cyclodextrins, and/or beta-cyclodextrins at a concentration such that the cyclodextrins increase the amount of the produced triterpenoid sapogenin secreted from the eukaryotic genetically engineered yeast cells into the culture medium in comparison to a culture medium lacking said cyclodextrins where the biosynthetic enzyme is an oxidosqualane cyclase and/or a cytochrome P450.

2. The method according to claim 1, wherein the yeast cells are *Saccharomyces* cells, *Schizosaccharomyces* cells, *Pichia* cells, *Yarrowia* cells, *Hansenula* cells, *Kluyveromyces* cells, or *Candida* cells.

3. The method according to claim 1, wherein the genetically engineered yeast cells are deficient in expression and/or activity of an enzyme involved in endogenous sterol synthesis.

4. The method according to claim 1, wherein the culture medium comprises cyclodextrins selected from the group consisting of randomly methylated cyclodextrins and hydroxypropylated cyclodextrins.

5. The method according to claim 1, wherein the culture medium comprises β-cyclodextrin.

6. The method according to claim 1, wherein the cyclodextrin concentration in the culture medium is less than 25 mM.

7. The method according to claim 1, wherein cyclodextrins are added to the culture medium at different consecutive time points.

8. The method according to claim 1, further comprising: extracting sapogenins from the culture medium.

9. The method according to claim 1, wherein the yeast cells are genetically engineered to overexpress an oxidosqualene cyclase and/or a cytochrome P450.

10. The method according to claim 6, wherein the cyclodextrin concentration is less than 10 mM.

11. The method according to claim 10, wherein the cyclodextrin concentration is between 2 mM and 7 mM.

* * * * *